US012576130B2

(12) United States Patent
DiAntonio et al.

(10) Patent No.: US 12,576,130 B2
(45) Date of Patent: Mar. 17, 2026

(54) DOMINANT NEGATIVE SARM1 MOLECULES COMPRISING A SUBSTITUTION AT POSITION 189, 190, 193, 194, 570 AND/OR 685 OF SARM1

(71) Applicant: Washington University, St. Louis, MO (US)

(72) Inventors: Aaron DiAntonio, St. Louis, MO (US); Jeffrey D. Milbrandt, St. Louis, MO (US); Daniel Summers, St. Louis, MO (US); Stefanie Geisler, St. Louis, MO (US); Xianrong Mao, St. Louis, MO (US)

(73) Assignee: Washington University, St. Louis, MO (US)

( * ) Notice: Subject to any disclaimer, the term of this patent is extended or adjusted under 35 U.S.C. 154(b) by 1183 days.

(21) Appl. No.: 16/757,254

(22) PCT Filed: Oct. 18, 2018

(86) PCT No.: PCT/US2018/056475
§ 371 (c)(1),
(2) Date: Apr. 17, 2020

(87) PCT Pub. No.: WO2019/079572
PCT Pub. Date: Apr. 25, 2019

(65) Prior Publication Data
US 2021/0187069 A1     Jun. 24, 2021

Related U.S. Application Data

(60) Provisional application No. 62/644,090, filed on Mar. 16, 2018, provisional application No. 62/573,967, filed on Oct. 18, 2017.

(51) Int. Cl.

| | |
|---|---|
| A61K 38/00 | (2006.01) |
| A61K 35/76 | (2015.01) |
| A61K 38/17 | (2006.01) |
| A61K 38/18 | (2006.01) |
| A61P 25/00 | (2006.01) |
| C07K 14/00 | (2006.01) |
| C07K 14/435 | (2006.01) |
| C07K 14/47 | (2006.01) |
| C07K 14/475 | (2006.01) |
| C07K 14/48 | (2006.01) |
| C07K 14/71 | (2006.01) |
| C12N 15/00 | (2006.01) |
| C12N 15/86 | (2006.01) |

(52) U.S. Cl.
CPC .......... *A61K 38/1709* (2013.01); *A61K 35/76* (2013.01); *A61K 38/1761* (2013.01); *A61K 38/18* (2013.01); *A61P 25/00* (2018.01); *C07K 14/435* (2013.01); *C07K 14/47* (2013.01); *C07K 14/475* (2013.01); *C07K 14/71*

(2013.01); *C12N 15/00* (2013.01); *C12N 15/86* (2013.01); *A61K 38/00* (2013.01)

(58) Field of Classification Search
CPC ................ A61K 38/00; A61K 38/1709; A61K 38/1761; A61K 38/16; A61K 47/6815; C07K 14/47; C07K 14/00; C07K 14/4702; C07K 14/4747; A61P 25/00; A61P 25/28; A61P 21/00
See application file for complete search history.

(56) References Cited

U.S. PATENT DOCUMENTS

| | | | | |
|---|---|---|---|---|
| 4,797,368 | A | 1/1989 | Carter et al. | |
| 4,863,457 | A | 9/1989 | Lee | |
| 4,868,116 | A | 9/1989 | Morgan et al. | |
| 4,897,355 | A | 1/1990 | Eppstein et al. | |
| 4,980,286 | A | 12/1990 | Morgan et al. | |
| 5,378,475 | A | 1/1995 | Smith et al. | |
| 5,443,505 | A | 8/1995 | Wong et al. | |
| 6,261,834 | B1 | 7/2001 | Srivastava | |
| 6,342,390 | B1 | 1/2002 | Wiener et al. | |
| 6,723,551 | B2 | 4/2004 | Kotin et al. | |
| 6,821,511 | B2 | 11/2004 | Kotin et al. | |
| 9,254,311 | B2 * | 2/2016 | Bancel | C07K 16/2887 |
| 9,486,521 | B2 * | 11/2016 | Freeman | A61P 25/28 |
| 11,253,503 | B2 * | 2/2022 | Milbrandt | A61K 31/4535 |
| 2012/0328629 | A1 * | 12/2012 | Freeman | G01N 33/6896 435/7.1 |
| 2014/0079712 | A1 * | 3/2014 | Freeman | A61K 39/3955 435/7.1 |

(Continued)

FOREIGN PATENT DOCUMENTS

| | | |
|---|---|---|
| WO | 8907136 A2 | 8/1989 |
| WO | 9002806 A1 | 3/1990 |

(Continued)

OTHER PUBLICATIONS

Gerdts et al., J. Neurosci. 2013; 33:13569-13580.*

(Continued)

*Primary Examiner* — Chang-Yu Wang

(74) *Attorney, Agent, or Firm* — Polsinelli PC

(57) ABSTRACT

The present invention provides compositions useful as inhibitors of SARM1 activity, pharmaceutical compositions thereof, and methods of using the same. The present invention provides dominant negative SARM1 molecules useful for treating a neurodegenerative or neurological disease or disorder, pharmaceutical compositions thereof, and methods of using the same.

9 Claims, 30 Drawing Sheets
(22 of 30 Drawing Sheet(s) Filed in Color)
Specification includes a Sequence Listing.

(56) References Cited

U.S. PATENT DOCUMENTS

2016/0151516 A1    6/2016  Bancel et al.
2021/0187069 A1 *  6/2021  DiAntonio ............. C12N 15/00

FOREIGN PATENT DOCUMENTS

WO         2007096854 A1     8/2007
WO      WO-2013151664 A1 * 10/2013    ......... A61K 31/7088
WO      WO-2018057989 A1 *  3/2018   ........... A61K 31/047

OTHER PUBLICATIONS

Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Gerdts et al.,J. Neurosci. 2013; 33:13560-13580.*
Summers et al., PNAS, 2016; E6271-E6280. www.pnas.org/cgi/doi/10.1073/pnas.1601506113.*
Extended European Search Report for European Application No. 18867429.5, mailed Oct. 27, 2021, 32 Pages.
First Office Action and Search Report for Chinese Patent Application No. 201880080877.2, dated Nov. 22, 2022, 26 pages.
Geisler S., et al., "S268. SARM1 Dominant-Negative—A New Therapeutic Approach to the Treatment of Axonal Degeneration," Annals of Neurology, vol. 84, No. S22, Oct. 2018, p. S113.
International Preliminary Report on Patentability for International Application No. PCT/US2018/056475, mailed Apr. 30, 2020, 09 Pages.
International Search Report and Written Opinion for International Application No. PCT/US2018/056475, mailed Feb. 22, 2019, 14 Pages.
Jiang Y., et al., "The NAD+-Mediated Self-Inhibition Mechanism of Pro-Neurodegenerative SARM1," Nature, Oct. 14, 2020, vol. 588, No. 7839, pp. 1-6.
Office Action for European Patent Application No. 18867429.5, mailed Jun. 20, 2023, 12 Pages.
Office Action for Japanese Patent Application No. 2020-521980, mailed on Dec. 6, 2022, 10 Pages.
Office Action for Japanese Patent Application No. 2020-521980, mailed on May 9, 2023, 4 Pages.
Partial Supplementary European Search Report for European Application No. 18867429.5, mailed Jun. 18, 2021, 28 Pages.
Second Office Action for Chinese Patent Application No. 201880080877.2, dated May 26, 2023, 13 pages.
Summers D.W., et al., "Supporting Information," Proceedings of the National Academy of Sciences (PNAS), 2016, pp. 1-6, Retrieved from the Internet: URL: https://www.pnas.org/doi/10.1073/pnas.1601506113.
Acsadi G., et al., "Human Dystrophin Expression in mdx Mice after Intramuscular Injection of DNA Constructs," Nature, Aug. 29, 1991, vol. 352, pp. 815-818.
Araki T., et al., "Increased Nuclear NAD Biosynthesis and SIRT1 Activation Prevent Axonal Degeneration," Science, Aug. 13, 2004, vol. 305, pp. 1010-1013.
Ausubel., et al., "Short Protocols in Molecular Biology," 5th ed., Current Protocols, 2002, ISBN-10: 0471250929.
Baneyx, "Protein Expression Technologies," Taylor & Francis, 2004, ISBN-10: 0954523253.
Bantel-Schaal U., et al., "Human Adeno-Associated Virus Type 5 is Only Distantly Related to Other Known Primate Helper-Dependent Parvoviruses," Journal of Virology, Feb. 1999, vol. 73, No. 2, pp. 939-947.
Bellucci A., et al., "The End Is the Beginning: Parkinson's Disease in the Light of Brain Imaging," Frontiers in Aging Neuroscience, Oct. 2017, vol. 9, No. 330, pp. 1-5.

Brigham K.L., et al., "Expression of a Prokaiyotic Gene in Cultured Lung Endothelial Cells after Lipofection with a Plasmid Vector," American Journal of Respiratory Cell and Molecular Biology, 1989, vol. 1, pp. 95-100.
Burke R.E., et al., "Axon Degeneration in Parkinson's Disease," Experimental Neurology, 2013, vol. 246, pp. 72-83.
Caminiti P.S., et al., "Axonal damage and loss of connectivity in nigrostriatal and mesolimbic dopamine pathways in early Parkinson's disease," NeuroImage Clinical, Mar. 2017, pp. 734-740.
Carter B.J., "Adeno-Associated Virus Vectors in Clinical Trials," Human Gene Therapy, May 2005, vol. 16, pp. 541-550.
Cashman C.R., et al., "Mechanisms of Distal Axonal Degeneration in Peripheral Neuropathies," Neuroscience Letters, 2015, vol. 596, pp. 1-18.
Cearley C.N., et al., "Transduction Characteristics of Adeno-associated Virus Vectors Expressing Cap Serotypes 7, 8, 3, and Rh10 in the Mouse Brain," Molecular Therapy, Mar. 2006, vol. 13, No. 3, pp. 528-537.
Chiorini J.A., et al., "Cloning and Characterization of Adeno-Associated Virus Type 5," Journal of Virology, Feb. 1999, vol. 73, No. 2, pp. 1309-1319.
Chiorini J.A., et al., "Cloning of Adeno-Associated Virus Type 4 (AAV4) and Generation of Recombinant AAV4 Particles," Journal of Virology, Sep. 1997, vol. 71, No. 9, pp. 6823-6833.
Conforti L., et al., "Wallerian Degeneration: An Emerging Axon Death Pathway Linking Injury and Disease," Nature Reviews Neuroscience, Jun. 2014, vol. 15, pp. 394-409.
De B.P., et al., "High Levels of Persistent Expression of alpha 1-Antityrpsin Mediated by the Nonhuman Primate Serotype rh. 10 Adeno-associated Virus Despite Preexisting Immunity to Common Human Adeno-associated Viruses," Molecular Therapy, Jan. 2006, vol. 13, No. 1, pp. 67-76.
Deverman B.E., et al., "Gene Therapy for Neurological Disorders: Progress and Prospects," Nature Reviews Drug Discovery, Aug. 10, 2018, vol. 17, pp. 1-19.
Elhai J., et al., "Conjugal Transfer of DNA to Cyanobacteria," Methods in Enzymology, Academic Press, Inc, 1988, vol. 167, pp. 747-754.
Essuman K., et al., "The SARM1 Toll/Interleukin-1 Receptor Domain Possesses Intrinsic NAD+ Cleavage Activity that Promotes Pathological Axonal Degeneration," Neuron, Mar. 22, 2017, vol. 93, pp. 1334-1343, 16 Pages.
Fazio P., et al., "Nigrostriatal Dopamine Transporter Availability in Early Parkinson's Disease," Movement Disorders, 2018, vol. 33, pp. 1-8.
Felgner P.L., et al., "Lipofection: A Highly Efficient, lipid-Mediated DNA-Transfection Procedure," Proceedings of the National Academy of Sciences, Nov. 1987, vol. 84, No. 21, pp. 7413-7417.
Fernandes K.A., et al., "Role of SARM1 and DR6 in Retinal Ganglion Cell Axonal and Somal Degeneration Following Axonal Injury," Experimental Eye Research, 2018, vol. 171, pp. 28 pages.
Fischer L.R., et al., "Axonal Degeneration in Motor Neuron Disease," Neurodegenerative Diseases, 2007, vol. 4, pp. 431-442.
Gao., et al., "Novel Adeno-Associated Viruses From Rhesus Monkeys as Vectors for Human Gene Therapy", Proceedings of the National Academy of Sciences, USA, Sep. 2002, vol. 99, No. 18, 11854-11859.
Gao G., et al, "Biology of AAV Serotype Vectors in Liver-Directed Gene Transfer to Nonhuman Primates", Molecular Therapy, Jan. 2006, vol. 13(1), pp. 77-87.
Gao G., et al., "Clades of Adeno-Associated Viruses Are Widely Disseminated in Human Tissues," Journal of Virology, Jun. 2004, vol. 78, No. 12, pp. 6381-6388.
Geisler S., et al., "Prevention of Vincristine-Induced Peripheral Neuropathy by Genetic Deletion of SARM1 in Mice," Brain, 2016, vol. 139, pp. 1-17.
Gellissen G., "Production of Recombinant Proteins: Novel Microbial and Eukaryotic Expression Systems," Wiley-VCH, Edition 2005, ISBN-10: 3527310363, 419 pages.
Gennaro A.R., et al., "Remington: The Science and Practice of Pharmacy," 18th Edition, Mack Publishing Company, Easton, 1995.

(56) References Cited

OTHER PUBLICATIONS

Gerdts J., et al., "SARM1 Activation Triggers Axon Degeneration Locally via NAD+ Destruction," Science, Apr. 24, 2015, vol. 348, No. 6233, pp. 453-457.

Gerdts J., et al., "Axon Self-Destruction: New Links among SARM1, MAPKs, and NAD+ Metabolism," Neuron, Feb. 3, 2016, vol. 89, pp. 449-460.

Gilley, J., et al., 2015. Absence of SARM1 rescues development and survival of NMNAT2-deficient axons. Cell Rep. 10:1974-1981. doi:10.1016/j.celrep.2015.02.060.

Gilley J., et al., "Sarm1 Deletion, but Not WldS, Confers Lifelong Rescue in a Mouse Model of Severe Axonopathy," Cell Reports, Oct. 3, 2017, vol. 21, pp. 10-16.

Gilley J., et al., "Endogenous Nmnat2 Is an Essential Survival Factor for Maintenance of Healthy Axons," PLoS Biology, Jan. 2010, vol. 8, No. 1, pp. 1-18.

Henninger N., et al., "Attenuated Traumatic Axonal Injury and Improved Functional Outcome After Traumatic Brain Injury in Mice Lacking Sarm1," Brain, 2016, vol. 139, pp. 1-12.

Howell G.R., et al., "Axons of Retinal Ganglion Cells are Insulted in the Optic Nerve Early in DBA/2J Glaucoma," Journal of Cell Biology, Dec. 31, 2007, vol. 179, No. 7, pp. 1523-1537.

Howell G.R., et al., "Intrinsic Axonal Degeneration Pathways are Critical for Glaucomatous Damage," Experimental Neurology, 2013, vol. 246, pp. 54-61.

Hunter D.A., et al., "Binary Imaging Analysis for Comprehensive Quantitative Histomorphometry of Peripheral Nerve," Journal of Neuroscience Methods, 2007, vol. 166, pp. 116-124.

Hwu W-L., et al., "Gene Therapy for Aromatic L-Amino Acid Decarboxylase Deficiency," Science Translational Medicine, May 16, 2012, vol. 4, No. 134, pp. 1-7.

Im D-S., et al., "The AAV Origin Binding Protein Rep68 is an ATP-Dependent Site-Specific Endonuclease with DNA Helicase Activity," Cell, May 4, 1990, vol. 61, No. 3, pp. 447-457.

Johnson V.E., et al., "Axonal Pathology in Traumatic Brain Injury," Experimental Neurology, 2013, vol. 246, pp. 1-9.

Koda-Kimble et al., "Applied Therapeutics: The Clinical Use of Drugs," Lippincott Williams & Wilkins, 2004, ISBN 0781748453.

Kugler S., et al., "Neuron-Specific Expression of Therapeutic Proteins: Evaluation of Different Cellular Promoters in Recombinant Adenoviral Vectors," Molecular and Cellular Neuroscience, 2001, vol. 17, No. 1, pp. 78-96.

Liberman, H. A. and Lachman, L., Eds., "Pharmaceutical Dosage Forms," Marcel Dekker Inc., New York, N.Y., 1980.

Lunn E.R., et al., "Absence of Wallerian Degeneration does not Hinder Regeneration in Peripheral Nerve," European Journal of Neuroscience, 1989, vol. 1, No. 1, pp. 27-33.

Mao Y., et al., "Persistent Suppression of Ocular Neovascularization with Intravitreal Administration of AAVrh.10 Coding for Bevacizumab," Human Gene Therapy, Dec. 2011, vol. 22, pp. 1525-1535.

Mendell J.R., et al., "Single-Dose Gene-Replacement Therapy for Spinal Muscular Atrophy," The New England Journal of Medicine, Nov. 2, 2017, vol. 377, No. 18, pp. 1713-1722.

Mittermeyer G., et al., "Long-Term Evaluation of a Phase 1 Study of AADC Gene Therapy for Parkinson's Disease," Human Gene Therapy, Apr. 2012, vol. 23, pp. 377-381.

Mulligan R.C., "The Basic Science of Gene Therapy," Science, May 14, 1993, vol. 260, No. 5110, pp. 926-932.

Narayanan K.B., et al., "Toll/Interleukin-1 Receptor (TIR) Domain-Mediated Cellular Signaling Pathways," Apoptosis, Jan. 7, 2015, vol. 20, pp. 14 pages.

O'Keeffe G.W., et al., "Evidence for Dopaminergic Axonal Degeneration as an Early Pathological Process in Parkinson's Disease," Parkinsonism Related Disorders, 2018, pp. 1-7.

Osterloh J.M., et al., "dSarm/Sarm1 Is Required for Activation of an Injury-Induced Axon Death Pathway," Science, Jul. 27, 2012, vol. 337, pp. 481-484.

Pereira D.J., et al., "The Adeno-Associated Virus (AAV) Rep Protein Acts as both a Repressor and an Activator to Regulate AAV Transcription during a Productive Infection," Journal of Virology, Feb. 1997, vol. 71, No. 2, pp. 1079-1088.

Remington J.P., "Remington's Pharmaceutical Sciences" 2005, A.R. Gennaro, Ed., 21st edition, ISBN: 0781746736.

Remington J.P., "Remington: The Science and Practice of Pharmacy," Lippincott Williams & Wilkins, 2001, 21st Edition.

Rutledge E.A., et al., "Infectious Clones and Vectors Derived from Adeno-Associated Virus (AAV) Serotypes Other Than AAV Type 2," Journal of Virology, Jan. 1998, vol. 72, No. 1, pp. 309-319.

Sajadi A., et al., "Wlds-Mediated Protection of Dopaminergic Fibers in an Animal Model of Parkinson Disease," Current Biology, Feb. 17, 2004, vol. 14, pp. 326-330.

Sambrook and Russel, "Condensed Protocols from Molecular Cloning: A Laboratory Manual," Cold Spring Harbor Laboratory Press, 2006, ISBN-10: 0879697717.

Sambrook and Russel, "Molecular Cloning: A Laboratory Manual," 3d ed., Cold Spring Harbor Laboratory Press, 2001, ISBN-10: 0879695773.

Sasaki Y., et al., "Nicotinamide Mononucleotide Adenylyl Transferase-Mediated Axonal Protection Requires Enzymatic Activity But Not Increased Levels of Neuronal Nicotinamide Adenine Dinucleotide," Journal of Neuroscience Research, Apr. 29, 2009, vol. 29, No. 17, pp. 5525-5535.

Sasaki Y., et al., "NMNAT1 Inhibits Axon Degeneration via Blockade of SARM1-Mediated NAD+ Depletion," eLife, 2016, vol. 5, pp. 1-15.

Sharqel, "Applied Biopharmaceutics & Pharmacokinetics," McGraw-Hill/Appleton & Lange, 2004, ISBN 0071375503.

Srivastava A., et al., "Nucleotide Sequence and Organization of the Adeno-Associated Virus 2 Genome," Journal of Virology, Feb. 1983, vol. 45, No. 2, pp. 555-564.

Studier F.W., "Protein Production by Auto-Induction in High-Density Shaking Cultures," Protein Expression and Purification, May 2005, vol. 41, No. 1, pp. 207-234.

Sumner C.J., et al., "Two Breakthrough Gene-Targeted Treatments for Spinal Muscular Atrophy: Challenges Remain," Journal of Clinical Investigation, Aug. 2018, vol. 128, No. 8, pp. 3219-3227.

Szretter K.J., et al., "The Immune Adaptor Molecule SARM Modulates Tumor Necrosis Factor Alpha Production and Microglia Activation in the Brainstem and Restricts West Nile Virus Pathogenesis," Journal of Virology, Sep. 2009, vol. 83, No. 18, pp. 9329-9338.

Tagliaferro P., et al., "Retrograde Axonal Degeneration in Parkinson Disease," Journal of Parkinson's Disease, 2016, vol. 6, pp. 1-15.

Turkiew, E., et al., 2017. Deletion of Sarm1 gene is neuroprotective in two models of peripheral neuropathy. J. Peripher. Nerv. Syst. 22:162-171. doi:10.1111/jns.12219.

"United States Pharmacopeia (USP 29) and National Formulary (NF 24)," United States Pharmacopeial Convention, Inc, Rockville, Maryland, 2005 ("USP/NF").

Verma I.M., "Retroviral Vectors for Gene Transfer, in Microbiology," American Society for Microbiology, 1985, pp. 229-232.

Wang M.S., et al., "The WldS Protein Protects Against Axonal Degeneration: A Model of Gene Therapy for Peripheral Neuropathy," Annals of Neurology, Dec. 2001, vol. 50, No. 6, pp. 773-779.

Wang M.S., et al., "Wlds Mice are Resistant to Paclitaxel (Taxol) Neuropathy," Annals of Neurology, Oct. 2002, vol. 52, No. 4, pp. 442-447.

Watanabe M., et al., "AAVrh. 10-Mediated Genetic Delivery of Bevacizumab to the Pleura to Provide Local Anti-VEGF to Suppress Growth of Metastatic Lung Tumors," Gene Therapy, Aug. 2010, vol. 17, No. 8, pp. 1042-1051.

Winter, "Basic Clinical Pharmacokinetics," 4th ed., Lippincott Williams & Wilkins, 2003, ISBN 0781741475.

Wolff J.A., et al., "Direct Gene Transfer into Mouse Muscle In vivo," Science, Mar. 1990, vol. 247(4949 Pt 1), pp. 1465-1468.

Wright J.F., et al., "Identification of Factors that Contribute to Recombinant AAV2 Particle Aggregation and Methods to Prevent its Occurrence During Vector Purification and Formulation," Molecular Therapy, Jul. 2005, vol. 12, No. 1, pp. 171-178.

(56)  References Cited

OTHER PUBLICATIONS

Wright J.F., et al., "Recombinant adeno-associated virus: formulation challenges and strategies for a gene therapy vector," Current opinion in drug discovery & development, 2003, vol. 6, No. 2, pp. 174-178.

Wu P., et al., "Mutational Analysis of the Adeno-Associated Virus Type 2 (AAV2) Capsid Gene and Construction of AAV2 Vectors with Altered Tropism," Journal of Virology, Sep. 2000, vol. 74, No. 18, pp. 8635-8647.

Wu Z., et al., "Adeno-Associated Virus Serotypes: Vector Toolkit for Human Gene Therapy," Molecular Therapy, Sep. 2006, vol. 14, No. 3, pp. 316-327.

Yang J., et al., "Pathological Axonal Death through a MAPK Cascade that Triggers a Local Energy Deficit," Cell, Jan. 15, 2015, vol. 160, pp. 161-176.

Yin T.C., et al., "Acute Axonal Degeneration Drives Development of Cognitive, Motor, and Visual Deficits after Blast-Mediated Traumatic Brain Injury in Mice," eNeuro, 2016, vol. 3, No. 5, pp. 1-11.

Ziogas N.K., et al., "Primary Traumatic Axonopathy in Mice Subjected to Impact Acceleration: A Reappraisal of Pathology and Mechanisms with High-Resolution Anatomical Methods," The Journal of Neuroscience, 2018, vol. 38, pp. 62 pages.

Zu Horste G.M., et al., "The WIds Transgene Reduces Axon Loss in a Charcot-Marie-Tooth Disease 1A Rat Model and Nicotinamide Delays Post-Traumatic Axonal Degeneration," Neurobiology of Disease, 2011, vol. 42, pp. 1-8.

Office Action for Canadian Application No. 3,079,409, dated Dec. 12, 2024, 12 pages.

Office Action for Japanese Application No. 2023-172739, dated Nov. 26, 2024, 5 pages.

Gerdts, et al., "Sarm1-Mediated Axon Degeneration Requires Both SAM and TIR Interactions," The Journal of Neuroscience, Aug. 14, 2013, vol. 33(33)13569-13580 (13 pages).

Summers, D.W., et al., "SARM1-specific motifs in the TIR domain enable NAD+ loss and regulate injury-induced SARM1 activation," PNAS, 113(41), Sep. 26, 2016, pp. E6271-E6280 (17 pages), [retrieved: www.pnas.org/cgl/doi/10.1073/pnas.160150611].

* cited by examiner

AAV8-Syn-SARM1-CDN-EGFP

5 days after cut

5 days after cut

5 days after cut

AAV-Syn-EGFP

AAV-Syn-SARM1-CDN-EGFP

AAV-Syn-EGFP

AAV-Syn-SARM1-CDN-EGFP

WT vector
K193R/E642A
H685A/E642A
K193R/E642A/H685A
K193R/H194A/H685A
SARM1 KO vector

DOMINANT NEGATIVE SARM1 MOLECULES COMPRISING A SUBSTITUTION AT POSITION 189, 190, 193, 194, 570 AND/OR 685 OF SARM1

CROSS REFERENCE TO RELATED APPLICATIONS

This application claims the benefit of International Application No. PCT/US2018/056475, filed Oct. 18, 2018 which claims the benefit of U.S. Provisional Application No. 62/573,967, filed Oct. 18, 2017, and U.S. Provisional Application No. 62/644,090, filed Mar. 16, 2018, the disclosures of which are hereby incorporated by reference in their entirety.

GOVERNMENTAL RIGHTS

This invention was made with government support under NS087632 and NS091448 awarded by the National Institutes of Health. The government has certain rights in the invention.

FIELD OF THE INVENTION

The present disclosure generally relates to various compositions, and methods, useful for inhibition of SARM1 activity and/or treating a neurodegenerative or neurological disease or disorder. In particular, the present disclosure provides nucleic acids encoding dominant negative SARM1 polypeptides for use in gene therapy.

BACKGROUND

Axonal degeneration is a hallmark of several neurological disorders including peripheral neuropathy, traumatic brain injury, and neurodegenerative diseases (Gerdts et al., SARM1 activation triggers axon degeneration locally via NAD(+) destruction. *Science* 348 2016, pp. 453-457, hereby incorporated by reference in its entirety). In Parkinson's disease and Amyotrophic Lateral Sclerosis, for example, axonal degeneration is an early event, preceding symptom onset and widespread neuronal loss (Kurowska et al., 2017; Fischer et al., Axonal degeneration in motor neuron disease *Neurodegener*. Dis. 4 2007 pp. 431-442; both of which are hereby incorporated by reference in their entireties).

Accordingly, a need exists for the development of novel therapeutic options for neurodegenerative disorders which target the molecular underpinnings of the axon degeneration program.

SUMMARY

Among the various aspects of the present disclosure provide dominant negative SARM1 molecules for use as a therapeutic intervention for many neurological disorders that involve axon degeneration or axonopathy.

In some embodiments, the present invention provides nucleic acids encoding dominant negative SARM1 polypeptides to prevent or ameliorate axonal degeneration, axonopathies and neurological diseases and disorders that involve axonal degeneration. In some embodiments, nucleic acids encoding a dominant negative SARM1 polypeptide are provided in a gene therapy vector. In some embodiments, the present disclosure provides an adeno-associated virus (AAV) vector comprising a nucleic acid sequence encoding a dominant negative SARM1 polypeptide. In some embodiments, the present disclosure also provides a composition comprising the AAV vectors and methods of using the AAV vector to inhibit axonal degeneration, including axonal degeneration that results from reduction or depletion of $NAD^+$.

In some embodiments, the present invention provides methods of treating a neuropathy or axonopathy associated with axonal degradation. In some such embodiments, a neuropathy or axonopathy associated with axonal degradation is selected from hereditary or congenital neuropathies or axonopathies. In some embodiments, a neuropathy or axonopathy associated with axonal degradation is selected from or associated with peripheral neuropathy, glaucoma, traumatic brain injury, Parkinson's disease, Alzheimer's disease, Herpes infection, diabetes, amyotrophic lateral sclerosis, a demyelinating disease, ischemia or stroke, chemical injury, thermal injury, and AIDS. In some embodiments, a neuropathy or axonopathy associated with axonal degradation is selected from Parkinson's disease or non-Parkinson's diseases, and Alzheimer's disease.

It has now been found that compositions of the present disclosure, and pharmaceutically acceptable compositions comprising the same, are effective as potent inhibitors of endogenous SARM1 activity through interactions with the dominant negative SARM1 molecules of the invention. In some embodiments, the dominant negative SARM1 molecule comprises at least one mutation in the region corresponding to amino acids 175 to 200. In some embodiments, the dominant negative SARM1 molecule comprises at least one mutation in the region corresponding to amino acids 650 to 675. In some embodiments, the dominant negative SARM1 molecule comprises at least one mutation in the region corresponding to amino acids 675 to 700. In some embodiments, the dominant negative SARM1 molecule comprises at least one mutation in the region corresponding to amino acids 175 to 200 and at least one mutation in the region corresponding to amino acids 675 to 700. In some embodiments, the dominant negative SARM1 molecule comprises at least one mutation in the region corresponding to amino acids 175 to 200, at least one mutation in the region corresponding to amino acids 650 to 675, and at least one mutation in the region corresponding to amino acids 675 to 700. In some embodiments, the dominant negative SARM1 molecule comprises an amino acid substitution at the residue corresponding to 193. In some embodiments, the dominant negative SARM1 molecule comprises an amino acid substitution at the residue corresponding to 685. In some embodiments, the dominant negative SARM1 molecule comprises an amino acid substitution at the residue corresponding to 193 and an amino acid substitution at the residue corresponding to 685. In some embodiments, the dominant negative SARM1 molecule leading to a degeneration index of about 0.4 or below at 36 hours, at 48 hours, at 72 hours, at 96 hours, at 120 hours or longer after axotomy.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE FIGURES

The application file contains at least one drawing executed in color. Copies of this patent application publication with color drawing(s) will be provided by the Office upon request and payment of the necessary fee.

FIG. 1A is a schematic representation of the domain structure of human SARM1. Individual point mutations are indicated in red. Dotted segments indicate deleted regions. Abbreviations: deltaTIR—amino acids (aa) 1-27 and 560-724 deleted; mt-mitochondrial binding sequence; ARM—HEAT/Armadillo motif; SAM-sterile alpha motif; TIR—Toll-like Interleukin receptor domain. FIG. 1B shows axons of wildtype dorsal root ganglion (DRG) neurons expressing the indicated constructs or axons of SARM1-KO DRG neurons expressing EGFP-vector were transected and imaged using high-throughput automated imaging at indicated time points. AxD was quantified using a degeneration index (DI), which ranges from 0 (perfectly intact) to 1 (perfectly fragmented). Shown are means±standard error (SEM) of 3 independent experiments, each reflecting averages of 5 wells per condition and experiment. The DI of 10-15 images was averaged per well. Data were tested with a two-way ANOVA showing significant main effects of groups $F_{(6,14)}=25.57$; $P<0.0001$; time: $F_{(7,98)}=138$, $P<0.0001$; and interaction $F_{(42, 98)}=8.809$; $P<0.0001$; and post-hoc Dunnett's multiple comparison test **$P=0.0001$; Vector versus deltaTIR: $P=0.0013$*$P=0.0122$; Vector versus K597E $P=0.0015$) FIG. 1C Upper row: Representative bright-field micrographs of wildtype axons expressing indicated constructs or SARM1-KO axons taken 24 hours after axon transection. Lower row: The mitochondrial potential was monitored with red fluorescent tetramethylrhodamine methyl ester (TMRM) in the same axons as shown in the row above. Upon loss of mitochondrial membrane potential, the red fluorescent signal disappears. FIG. 1D shows axons of SARM1-KO neurons expressing either enzymatically active, wildtype (WT) SARM1 or indicated constructs were transected and AxD determined over time. Data are presented as mean±SEM. Two-way ANOVA shows significant main effect of groups $F_{(5,12)}=122.5$ $P<0.0001$; time ($F4$, 48)=124, $P<0.001$ and interaction $F_{(20,48)}=38.94$, $P<0.0001$; Dunnett's multiple comparison; **$P=0.0001$; n=3 independent experiments; 4 wells averaged per experiment. FIG. 1E is representative bright-field images of SARM1-KO axons expressing constructs indicated in (D), at 72 hours after cut. (C,E) Scale bars 50 μm.

FIG. 2A shows degeneration of wildtype DRG neurons expressing EGFP-vector or the SARM1-compound dominant negative (SARM1-CDN) and of SARM1 KO neurons expressing EGFP-vector after transection. Degeneration index ranges from 0 (completely intact) to 1 (completely fragmented). Data are presented as mean±SEM, tested with a two-way ANOVA, which shows significant main effects of group $F_{(2,9)}=2710$, $P<0.0001$; time ($F8,72)=298.7$, $P<0.0001$ and interaction $F_{(16,72)}=154$, $P<0.0001$. Dunnett's multiple comparison test vector versus SARM1-CDN and SARM1-KO **$P=0.0001$. FIG. 2B and FIG. 2C show representative bright-field (FIG. 2B) and TMRM (FIG. 2C) images of axons expressing constructs indicated in (FIG. 2A), at 96 hours after axotomy. (FIG. 2D) HPLC was used to measure NAD+ levels in wildtype and SARM1-KO neurons expressing EGFP-vector or SARM1-CDN from axon extracts 4 hours after transection and normalized to baseline (=immediately after cut). A one way ANOVA shows a significant main effect $F_{(2,6)}=20.01$, $P=0.0022$; post-hoc Tukey's multiple comparison test shows vector vs SARM1-CDN $P=0.0036$, vector vs SARM1-KO $P=0.0039$, SARM1-KO vs SARM1-CDN $P=0.9969$. n=3 independent experiments, comprising results from 4 wells averaged per condition and experiment. FIG. 2E is wildtype DRG neurons expressing EGFP-vector or SARM1-CDN and SARM1-KO neurons were treated with 40 nM Vincristine or vehicle and AxD determined using the degeneration index. Data are represented as means±SEM; two way ANOVA shows significant main effect of groups $F_{(3,8)}$ =259.6; $P<0.0001$; time $F_{(5,40)}=89.28$, $P<0.0001$; and interaction $F_{(15,40)}=38.59$; $P<0.0001$; post-hoc Dunnett's multiple comparison test shows wildtype vector vincristine versus SARM1-CDN vincristine, SARM1-KO vincristine and SARM1-KO vehicle **$P=0.0001$; n=3 independent experiments, comprising 2-4 wells per condition in each experiment. FIG. 2F shows representative bright field (upper row) and TMRM (lower row) images of the constructs indicated in (FIG. 2D), at 96 hours after vincristine administration. Scale bars: 50 μm.

FIG. 3A Upper row: Schematic of the AAV vector expressing human SARM1 mutated at K193 and H685 under control of the neuron-specific human synapsin promoter (Syn-SARM1-CDN-EGFP). Lower row: Schematic of the EGFP-vector (Syn-EGFP) used for control experiments. FIG. 3B AAV8-Syn-SARM1-CDN-EGFP or EGFP-vector (AAV8-Syn-EGFP) were injected intrathecally (6×1011 vg) into mice at postnatal day 11 or 12 (P11/12). Five weeks later, the right sciatic nerve was transected and 5 days later tissue collected for analysis. FIG. 3C is representative micrographs taken in situ of (from left to right) dorsal root ganglia (asterisk) attached to the spinal cord (SC), the left (uninjured) sciatic nerve (arrow) with its branches (arrowheads), and intercostal nerves (white arrowhead) expressing green fluorescent protein 5.5 weeks after injection with AAV8-Syn-SARM1-CDN-EGFP; m—muscle; Scale bars: 2 mm. FIG. 3D shows representative confocal image of a 6 μm thick section of a dorsal root ganglion after injecting EGFP-vector (left column; Syn-EGFP) or SARM1-CDN (right column; Syn-SARM1-DN-EGFP). Sections were stained with PGP 9.5 (red; dorsal root ganglion neurons) and anti-GFP (green; construct expression) and coverslipped with Vectamount containing DAPI (blue; nuclear marker). FIG. 3E is representative confocal image of a 6 μm thick section of the right (transected) sciatic nerve taken 5 days after cut in mice injected with the EGFP-vector (Syn-EGFP; left column) or SARM1-CDN (Syn-SARM1-CDN-EGFP; right column). Sections were stained with antibodies to Neurofilament 200 and peripherin (red; axonal markers) and green fluorescent protein (green; construct expression) and mounted with Vectashield containing DAPI (blue; nuclear marker). (FIG. 3D, FIG. 3E) Scale bars: 50 μm.

(FIG. 4A, FIG. 4B) Representative photomicrographs of toluidine blue stained semithin cross sections of the right sural nerve five days after transection of the sciatic nerve in mice injected with vector (A; n=4) or SARM1-CDN (SARM1-CDN) (B; n=5). (A'B') Enlargements of areas indicated by rectangles in (FIG. 4A) and (FIG. 4B). The arrow and arrowhead indicate lipid laden histiocytes and myelin debris, respectively. (FIG. 4C, FIG. 4D) Representative electron micrographs of the right sural nerve of a mouse injected with EGFP-vector showing complete loss of internal nerve architecture (FIG. 4C) whereas unmyelinated (asterisks) and myelinated axons are preserved after SARM1-CDN injection (FIG. 4D). (C',D') Enlargements of areas indicated by rectangles in (FIG. 4C) and (FIG. 4D). (FIG. 4E, FIG. 4F) All axons in cross sections of the entire sural nerve were counted in wildtype mice injected with vector (n=4 in E; n=3 in F) or SARM1-CDN (n=5 in E, n=3 in F) or in SARM1-KO mice (n=5 in E and F) and expressed as % of axon numbers of the respective intact contralateral sides at 5 (FIG. 4E) and 10 (FIG. 4F) days after transection. A one way ANOVA shows significant main effects in (FIG. 4E) [F(2,11)=97.13, P<0.0001; post-hoc Tukey's multiple comparison test shows vector versus SARM1-SARM1-CDN **P<0.0001; Vector versus SARM1-KO P<0.0001; SARM1-CDN versus SARM1-KO P=0.5953] and (FIG. 4F) [F(2,8)=20.73; P=0.0007; Tukey's multiple comparison test shows vector versus SARM1-CDNP=0.0077; vector versus SARM1-KO ***P=0.0005; SARM1-CDN vs SARM1-KO P=0.2543]. (FIG. 4G) Representative micrographs of toluidine blue stained sections of the sural nerve 10 days after cut. Lower row displays enlargements of indicated areas in the images above. Scale bars: (A,B) 50 μm, (A',B') 10 μm, (C,D) 5 μm, (C',D') 1 μm, (G, upper) 50 μm, (G, lower) 10 μm.

(FIG. 5B) Means±SEM of Hoechst positive cells expressing SARM1-dominant-negatives. More than 100 cells per well were counted and data from at least three independent experiments were averaged for each construct. SARM1-CDN=SARM1 compound dominant negative.

(FIG. 6A, FIG. 6B) Axons of wildtype dorsal root ganglion (DRG) neurons expressing the indicated constructs were transected and imaged using high-throughput automated imaging at indicated time points. AxD was quantified using a degeneration index (DI), which ranges from 0 (perfectly intact) to 1 (perfectly fragmented). Shown are means±standard error (SEM) of 3 independent experiments, each reflecting averages of 4 wells per condition and experiment. The DI of at least 6 images was averaged per well. (FIG. 6A) Data were tested with a two-way ANOVA showing significant main effects of groups F(4,13)=22.77; P<0.0001; time: F(5,65)=48.59 P<0.0001; and interaction F(20,65)=15.31; P<0.0001; post hoc Tukey's multiple comparison test shows no statistical difference between H685A and H685Y or between K193R and K193A. Vector versus all constructs 12-48 hours: **P<0.0001 Vector versus K193R and K193A 72 hours: P<0.0001; Vector versus H685A 72 hrs: P=0.0040; Vector versus H685Y 72 hrs *P=0.0225. (FIG. 6B) Data were tested with a two-way NAOVA, which shows significant main effects of group F(2,6)=228.8, P<0.0001, time F(5,30)=189.9, P<0.0001 and interaction F(10,30)=54.53, P<0.0001. Tukey's multiple comparison test vector versus SARM1-K193R/H685A and versus SARM1-K193R/H194A/H685A ****P<0.0001; SARM1K193R/H685A versus SARM1-K193R/H194A/H685A—no statistical significant difference.

FIG. 7C and FIG. 7D are enlargements of A and B, respectively. Nerves of mice injected with AAV8-Syn-EGFP and AAV8-Syn-SARM1-CDN-EGFP exhibit no significant difference in axon size distribution (FIG. 7E) or G ratios, a measure of axonal myelination (FIG. 7F). Data were subjected to multiple (FIG. 7E) or simple (FIG. 7F) t-tests (n=3 per group). Scale bars 20 μm in A and B; 10 μm in C and D. SARM1-CDN=SARM1 compound dominant negative FIG. 8B and FIG. 8C show brightfield images of axons expressing indicated constructs represented in A, taken at 24 hours (FIG. 8B) and 96 hours (FIG. 4C) hours, **P<0.0001; p<0.01; Error bars reflect SEM.

FIG. 9A show wildtype (WT) DRG neurons expressing the indicated constructs (vector, K193R/E642A, H685A/E642A, K193R/H194A/H685A, K193R/E642A, H685Y) or SARM1 KO DRGs expressing the empty vector were incubated with 40 nM vincristine and axon degeneration was evaluated at the indicated time points. In WT DRGs expressing the empty vector, axons degenerate by 24 hours and completely fragmented at 48 hours after vincristine administration. In contrast, axons of WT DRGs expressing SARM1 double and triple point mutations and axons of SARM1 KO neurons are protected from vincristine induced axon degeneration for at least 120 hours. FIG. 9B shows bright field photographs of the indicated constructs evaluated in A, taken 120 hours after vincristine administration. ****P<0.0001; Error bars reflect ±SEM.

FIG. 11A Wildtype CD1 DRG neurons were infected with virus carrying wildtype Sarm1 (WT), E189K, H190A, or C199S mutation. Five days later, axons were severed and the severity of axon degeneration (ADI) was monitored. E189K and H190A showed a significant protection compared with WT infection while C199S mutation didn't offer any protection. FIG. 11B Wildtype CD1 DRG neurons were infected with virus carrying wildtype Sarm1 (WT), R570A mutation. Five days later, axons were severed and the severity of axon degeneration (ADI) was monitored. R570A showed a significant protection compared with WT. FIG. 11C graphically depicts neurons expressing the indicated SARM1 constructs ability to inhibit axon degeneration. Axons expressing SARM1 E569K, D627K, K628D, or C629S degenerate at a similar speed as wild-type at 24 hours, indicating that they does not act as a dominant negatives.

Figure 1A:
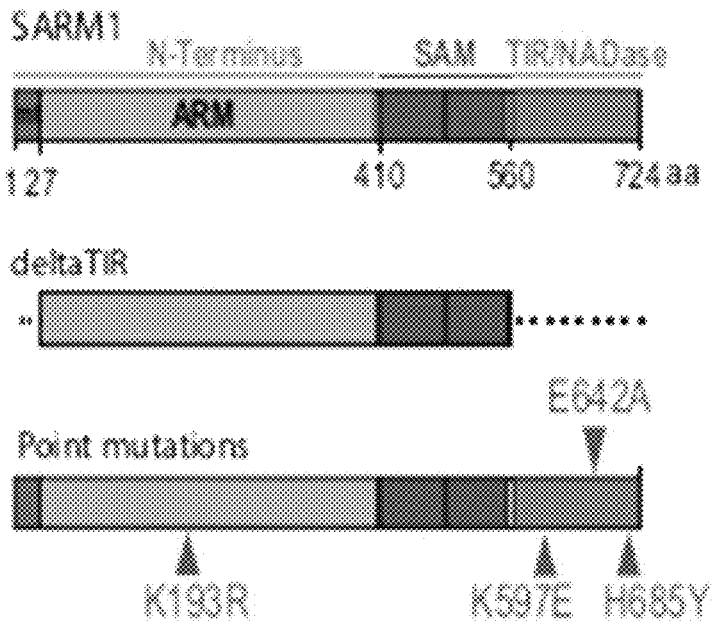
FIG. 1A, FIG. 1B, FIG. 1C, FIG. 1D and FIG. 1E show the identification of SARM1 dominant-negative transgenes.

Reference to various embodiments does not limit the scope of the invention. Figures represented herein are not limitations to the various embodiments according to the invention and are presented for exemplary illustration of the invention.

DETAILED DESCRIPTION

The present disclosure provides, generally, methods and compositions for preventing or ameliorating diseases and disorders resulting from axonal degeneration. In particular, provided herein are dominant negative SARM1 molecules for use as a therapeutic intervention for many neurological disorders that involve axon degeneration or axonopathy.

Axonal degeneration (AxD) is an early, potentially initiating event of some of the most prevalent neurological diseases, including peripheral neuropathies, traumatic brain injury, Parkinson's disease and glaucoma (Howell et al., 2007, 2013; Johnson et al., 2013; Cashman and Höke, 2015; Tagliaferro and Burke, 2016; Bellucci et al., 2017). Although AxD is central to many neurological disorders, no treatments currently exist that effectively target axonal breakdown.

Significant progress has been made unraveling mechanisms of AxD. The discovery of the Wallerian degeneration slow mouse, which harbors a spontaneous mutation causing significantly delayed AxD (Lunn et al., 1989), revealed that axons distal to a cut do not degenerate passively, but instead due to the activation of a genetically encoded AxD program. Recently, two unbiased, large scale forward genetic screens, one in invertebrates and one in mammals, independently identified sterile alpha and TIR motif containing protein 1 (SARM1) as the central executioner of this endogenous AxD program (Osterloh et al., 2012; Gerdts et al., 2013). Genetic deletion of SARM1 markedly preserves the integrity of *Drosophila* olfactory bulb distal axons for more than 50 days after a cut and mouse sciatic distal segments for more than 2 weeks after transection. SARM1 is not only necessary for AxD, it is also sufficient (Gerdts et al., 2015). Activation of SARM1 in healthy axons results in AxD, even in the absence of injury. Hence, SARM1 is the fundamental executioner of the AxD program (Gerdts et al., 2016).

Genetic deletion of SARM1 not only protects axons from degeneration after a cut, but also in models of several neurological diseases, including peripheral neuropathies (Geisler et al., 2016; Turkiew et al., 2017) and traumatic brain injury (Henninger et al., 2016; Ziogas and Koliatsos, 2018). This axon protection is associated with greatly improved functional outcomes, suggesting that targeting SARM1 is a viable strategy to treat neurological diseases characterized by early AxD. Importantly, SARM1 is expressed mainly in neurons and SARM1 knock-out mice have a normal lifespan and no overt behavioral abnormalities, suggesting that targeting SARM1 may be well tolerated. Unfortunately, there are currently no known drugs that inhibit SARM1 activity.

SARM1 is a multidomain protein that consists of an auto-inhibitory N terminus, tandem SAM domains that mediate constitutive homomultimerization, and an executioner TIR NADase domain (Gerdts et al., 2013, 2016; Essuman et al., 2017). Upon injury, N-terminal inhibition is relieved, allowing for TIR-TIR interactions that activate the intrinsic NADase enzyme thereby cleaving the essential metabolic cofactor NAD+ and driving AxD (Gerdts et al., 2016; Essuman et al., 2017). Because SARM1 exists as a homomultimer, co-expression of mutant SARM1 with wild-type SARM1 can act as a dominant-negative, blocking wildtype SARM1 function (Gerdts et al., 2013). SARM1 lacking a TIR domain inhibits wildtype SARM1 function, likely by disrupting the TIR-TIR interactions that activate the enzyme. In addition, we previously identified a highly conserved residue in the TIR domain that is required for the relief of N-terminal autoinhibition and, hence, injury-induced activation of SARM1 (Summers et al., 2016). Expression of this SARM1 mutant (SARM1-K597E) delays AxD in vitro by inhibiting the function of wildtype SARM1. While expressing these SARM1 dominant-negative mutants in wildtype neurons does inhibit pathological AxD, neither blocks axon loss as effectively as the absence of SARM1.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules of the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Various aspects of the invention are described in further detail in the following sections.

(I) Compositions (a) Dominant Negative SARM1 Molecules

One aspect of the present disclosure provides for dominant negative SARM1 polypeptides, as well as nucleic acids encoding the same. As used herein the term "dominant negative SARM1 molecule" is used to encompass both dominant negative SARM1 polypeptides and nucleic acids encoding dominant negative SARM1 polypeptides. Exemplary dominant negative polypeptides and encoding nucleic acids are described below.

As used herein the term "dominant negative SARM1" refers to a mutated SARM1 polypeptide or a nucleic acid encoding the same, which is capable of interacting with a wild-type SARM1 polypeptide, and inhibiting the function of the wild-type SARM1 polypeptide. In some embodiments, administration of a dominant negative SARM1 molecule inhibits the function of endogenous SARM1 to act as a central executioner of the endogenous AxD program. In particular, the term "mutant", "mutated" or "mutation" as it refers to SARM1 is intended to include any polypeptide or representation thereof (e.g. truncations, or fragments) that differs from its corresponding wild-type polypeptide by having at least one amino acid substitution, addition or deletion. In some embodiments, a dominant negative SARM1 comprises one or more amino acid substitutions. In an exemplary embodiment, the amino acid substitution is an arginine substitution.

As used herein, "SARM1" includes both a "SARM1 protein" and a "SARM1 analogue". Unless otherwise indicated, "protein" shall include a protein, protein domain, polypeptide, or peptide, and any fragment thereof. Human wild-type SARM1 protein has the amino acid sequence as set forth in SEQ ID NO:1. Homologs can be identified by comparison of amino acid sequence, e.g., manually or by using known homology-based search algorithms such as those commonly known and referred to as BLAST, FASTA, and Smith-Waterman. A local sequence alignment program, e.g., BLAST, can be used to search a database of sequences to find similar sequences, and the summary Expectation value (E-value) used to measure the sequence base similarity. As a protein hit with the best E-value for a particular organism may not necessarily be an ortholog or the only ortholog, a reciprocal query is used in the present invention to filter hit sequences with significant E-values for ortholog identification. The reciprocal query entails search of the significant hits against a database of amino acid sequences from the base organism that are similar to the sequence of the query protein. A hit is a likely ortholog, when the reciprocal query's best hit is the query protein itself or a protein encoded by a duplicated gene after speciation. In some embodiments, the dominant negative SARM1 is a human dominant negative SARM1, a mouse dominant negative SARM1, a zebrafish dominant negative SARM1, a chimpanzee dominant negative SARM1, a Rhesus monkey dominant negative SARM1, a canine dominant negative SARM1, a feline dominant negative SARM1, a rat dominant negative SARM1, a chicken dominant negative SARM1, *Drosophila* dominant negative SARM1, a mosquito dominant negative SARM1, a *C. elegans* dominant negative SARM1, or a frog dominant negative SARM1.

In certain embodiments, the dominant negative SARM1 comprises at least one mutation in the region corresponding to amino acids 1 to 25, at least one mutation in the region corresponding to amino acids 25 to 50, at least one mutation in the region corresponding to amino acids 50 to 75, at least one mutation in the region corresponding to amino acids 75 to 100, at least one mutation in the region corresponding to amino acids 100 to 125, at least one mutation in the region corresponding to amino acids 125 to 150, at least one mutation in the region corresponding to amino acids 150 to 175, at least one mutation in the region corresponding to amino acids 175 to 200, at least one mutation in the region corresponding to amino acids 200 to 225, at least one mutation in the region corresponding to amino acids 225 to 250 at least one mutation in the region corresponding to amino acids 250 to 275, at least one mutation in the region corresponding to amino acids 275 to 300, at least one mutation in the region corresponding to amino acids 300 to 325, at least one mutation in the region corresponding to amino acids 325 to 350, at least one mutation in the region corresponding to amino acids 350 to 375, at least one mutation in the region corresponding to amino acids 375 to 400, at least one mutation in the region corresponding to amino acids 400 to 425, at least one mutation in the region corresponding to amino acids 425 to 450, at least one mutation in the region corresponding to amino acids 450 to 475, at least one mutation in the region corresponding to amino acids 475 to 500, at least one mutation in the region corresponding to amino acids 500 to 525, at least one mutation in the region corresponding to amino acids 525 to 550, at least one mutation in the region corresponding to amino acids 550 to 575, at least one mutation in the region corresponding to amino acids 575 to 600, at least one mutation in the region corresponding to amino acids 600 to 625, at least one mutation in the region corresponding to amino acids 625 to 650, at least one mutation in the region corresponding to amino acids 650 to 675, at least one mutation in the region corresponding to amino acids 675 to 700, at least one mutation in the region corresponding to amino acids 700 to 724, or a combination thereof. In some embodiments the position of the mutation in a dominant negative SARM1 is determined by sequence alignment with SEQ ID NO:1. In another aspect, a dominant negative SARM1 comprises at least one mutation in the region corresponding to amino acids 625 to 650, wherein the amino acid corresponding to 642 is not mutated. In one aspect, a dominant negative SARM1 comprises an amino acid substitution at the residue corresponding to 193. In another aspect, a dominant negative SARM1 comprises an amino acid substitution at the residue corresponding to 685. In yet another aspect, a dominant negative SARM1 comprises an amino acid substitution at the residue corresponding to 193 and an amino acid substitution at the residue corresponding to 685. In still yet another aspect, a dominant negative SARM1 consists essentially of an amino acid substitution at the residue corresponding to 193 and an amino acid substitution at the residue corresponding to 685. In another aspect, a dominant negative SARM1 consists of an amino acid substitution at the residue corresponding to 193 and an amino acid substitution at the residue corresponding to 685.

In some embodiments, a dominant negative SARM1 comprises an amino acid sequence that has at least 60, 65, 70, 75, 80, 85, 90, or 95% homology with SEQ ID NO: 1, 3, 4, 5, 6, 7, 8, 10, 13 or 14. In one embodiment, the dominant negative SARM1 comprises an amino acid sequence that has at least about 95, 96, 97, 98, or 99% sequence homology with SEQ ID NO: 1, 3, 4, 5, 6, 7, 8, 10, 13 or 14. A "homologous" amino acid sequence, as used herein, refers to an amino acid sequence that differs from a reference amino acid sequence, only by one or more (e.g., 1, 2, 3, 4 or 5) conservative amino acid substitutions, or by one or more (e.g., 1, 2, 3, 4 or 5) non-conservative amino acid substitutions, deletions, or additions. Homologous amino acid sequences include peptide sequences that are identical or substantially identical to a reference amino acid sequence. By "amino acid sequence substantially identical" is meant a sequence that is at least 90%, preferably 95%, more preferably 97%, and most preferably 99% identical to an amino acid sequence of reference and that preferably differs from the sequence of reference, if at all, by a majority of conservative amino acid substitutions.

Conservative amino acid substitutions typically include substitutions among amino acids of the same class. These classes include, for example, (a) amino acids having uncharged polar side chains, such as asparagine, glutamine, serine, threonine, and tyrosine; (b) amino acids having basic side chains, such as lysine, arginine, and histidine; (c) amino acids having acidic side chains, such as aspartic acid and glutamic acid; and (d) amino acids having nonpolar side chains, such as glycine, alanine, valine, leucine, isoleucine, proline, phenylalanine, methionine, tryptophan, and cysteine.

As used herein, the term "inhibiting SARM1 activity" refers to inhibition, negation, or diminution of certain particular activities of endogenous SARM1. These particular attributes include the activity of SARM1 as a central regulator of axonal degradation. Inhibiting SARM1 activity means a measurable change in endogenous SARM1 activity between a sample comprising a dominant negative SARM1 or dominant negative SARM1 composition, compared to an equivalent sample comprising endogenous SARM1 activity in the absence of a provided dominant negative SARM1 or dominant negative SARM1 composition. In some embodiments, a dominant negative SARM1 or dominant negative SARM1 composition "inhibits" SARM1 activity by inhibiting, delaying, or reducing SARM1-mediated axon degeneration. In some embodiments, SARM1 inhibition a reduced degeneration index, as compared to a control. In some embodiments, a dominant negative SARM1 or dominant negative SARM1 composition leads to a degeneration index provided by is about 0.5, about 0.45, about 0.4, about 0.35, about 0.3, about 0.25, about 0.2, about 0.15, about 0.1, about 0.5 or about 0.01. In some embodiments, the dominant negative SARM1 molecule leads to a degeneration index of about 0.4 or below at 36 hours, at 48 hours, at 72 hours, at 96 hours, at 120 hours or longer after axotomy. In some embodiments, a dominant negative SARM1 or dominant negative SARM1 composition "inhibits" SARM1 activity by at least 10%, 20%, 25%, 50%, 75% or more as compared to the control.

The method to determine the degeneration index resulting from the expression of a dominant negative SARM1 molecule is as follows. For the production of lentiviral particles containing SARM1 expression transgenes, HEK293t cells are transfected with the following plasmids: pcDNA expressing vesicular stomatitis virus glycoprotein, PspAX2 lentiviral packaging plasmid, and an FUGW plasmid containing the SARM1 open reading frame downstream of the human ubiquitin promoter. Two days after transfection, media supernatant containing lentiviral particles is collected and stored at −80° C. until applied to primary neuron cultures.

For functional analysis of SARM1 dominant negative molecules, primary embryonic Dorsal Root Ganglion (DRG) neurons are isolated from embryonic day 13.5 mouse embryos. DRG neurons are maintained in neurobasal medium supplemented with L-glutamine, 2% (vol/vol) B27 supplement, 50 ng/mL NGF, and 1 μM 5-fluoro-2'deoxyuridine plus 1 μM uridine to induce death of mitotic cells. DRG neurons are seeded on plates precoated with poly-D-lysine and laminin. On days in vitro (DIV) 1, DRGs are transduced with lentivirus containing an expression transgene encoding wildtype SARM1 or dominant negative SARM1 molecule. On DIV 7, axons are severed with a razor blade and the distal axons are visualized at the indicated time point after axotomy under brightfield microscopy.

Axon degeneration is quantified from bright-field images using an ImageJ macro (Sasaki, 2009) that defines the ratio of fragmented axon area to total axon area and expressed as degeneration index (DI). This metric ranges from 0 (perfectly intact) to 1 (completely fragmented) and values of 0.5 and above correspond to extensive axon degeneration. Ten images per well are measured as technical replicates, and 4-6 wells per condition are averaged. At least three independent experiments are performed.

The dominant negative SARM1 polypeptide may optionally comprise further functional domains such that they increase the availability or targeting of the dominant negative molecule to a cell (e.g., cell-penetrating) or at least one tag. In some embodiments, the dominant negative protein further comprises at least one additional domain. In one embodiment, the cell-penetrating domain can be a cell-penetrating peptide sequence derived from the HIV-1 TAT protein. In non-limiting examples the at least one tag is a StrepTag, a polyhistidine tag, an antibody epitope (e.g., derived from myc), and the like or a combination thereof. The additional domain or at least one tag can be located at the N-terminus, the C-terminus, or in an internal location of the protein. The additional domain or tag may be attached to a dominant negative SARM1 by a linker domain, where the linker domain optionally comprises an enzymatic cleavage site for the release of the cell-penetrating domain from the dominant negative SARM1 upon entry into a cell. Preferably, the cleavage enzyme is an enzyme enriched in neurons.

Another aspect of the present disclosure provides nucleic acids encoding any of the dominant negative molecules described above. The nucleic acid can be DNA or RNA. In one embodiment the DNA can be present in a vector. The nucleic acid sequences which encode the dominant negative molecule of the invention can be operatively linked to expression control sequences. "Operatively linked" refers to a juxtaposition wherein the components so described are in a relationship permitting them to function in their intended manner. An expression control sequence operatively linked to a coding sequence is achieved under conditions compatible with the expression control sequences. As used herein, the expression control sequences refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, and maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

In some embodiments, a dominant negative SARM1 comprises an nucleic acid sequence that has at least 60, 65, 70, 75, 80, 85, 90, or 95% homology with SEQ ID NO: 15. In one embodiment, the dominant negative SARM1 comprises an nucleic acid sequence that has at least about 95, 96, 97, 98, or 99% sequence homology with SEQ ID NO: 15.

In one aspect, the present disclosure provides for a vector comprising a nucleic acid sequence encoding for a dominant negative SARM1 polypeptide. In one aspect, the present disclosure is predicated, at least in part, on the ability of adeno-associated virus (AAV) vectors to be safely administered to humans and to provide persistent expression of a therapeutic transgene. The invention provides an adeno-associated virus (AAV) vector which comprises, consists essentially of, or consists of a nucleic acid sequence encoding a dominant negative SARM1 polypeptide. When the AAV vector consists essentially of a nucleic acid sequence encoding a dominant negative SARM1 polypeptide, additional components can be included that do not materially affect the AAV vector (e.g., genetic elements such as poly(A) sequences or restriction enzyme sites that facilitate manipulation of the vector in vitro). When the AAV vector consists of a nucleic acid sequence encoding a dominant negative SARM1 polypeptide, the AAV vector does not comprise any additional components (i.e., components that are not endogenous to AAV and are not required to effect expression of the nucleic acid sequence to thereby provide the dominant negative SARM1).

Adeno-associated virus is a member of the Parvoviridae family and comprises a linear, single-stranded DNA genome of less than about 5,000 nucleotides. AAV requires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DNA replication by serving as primers for the cellular DNA polymerase complex. The Rep genes encode the Rep proteins Rep78, Rep68, Rep52, and Rep40. Rep78 and Rep68 are transcribed from the p5 promoter, and Rep 52 and Rep40 are transcribed from the p19 promoter. The Rep78 and Rep68 proteins are multifunctional DNA binding proteins that perform helicase and nickase functions during productive replication to allow for the resolution of AAV termini (see, e.g., Im et al., Cell, 61: 447-57 (1990)). These proteins also regulate transcription from endogenous AAV promoters and promoters within helper viruses (see, e.g., Pereira et al., J. Virol., 71: 1079-1088 (1997)). The other Rep proteins modify the function of Rep78 and Rep68. The cap genes encode the capsid proteins VP1, VP2, and VP3. The cap genes are transcribed from the p40 promoter. In a particular embodiment, the AAV contains a pair of inverted terminal repeats (ITRs) which flank at least one cassette containing a promoter which directs cell-specific expression (e.g. neuron) operably linked to a heterologous gene. Heterologous in this context refers to any nucleotide sequence or gene which is not native to the AAV or B19 parvovirus (e.g. dominant negative SARM1). Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference in its entirety for material related to the AAV vector.

As used herein, the term "AAV vector" means a vector derived from an adeno-associated virus serotype. In non-limitation examples AAV vectors include, AAV1, AAV2, AAV3, AAV4, AAV5, AAV6, AAV7, AAV8, AAV9, and mutated forms thereof. AAV vectors can have one or more of the AAV wild-type genes deleted in whole or part, preferably the rep and/or cap genes, but retain functional flanking ITR sequences. Despite the high degree of homology, the different serotypes have tropisms for different tissues.

An AAV vector, as disclosed herein, can be generated using any AAV serotype known in the art. Several AAV serotypes and over 100 AAV variants have been isolated from adenovirus stocks or from human or nonhuman primate tissues (reviewed in, e.g., Wu et al., Molecular Therapy, 14(3): 316-327 (2006)). Generally, the AAV serotypes have genomic sequences of significant homology at the nucleic acid sequence and amino acid sequence levels, such that different serotypes have an identical set of genetic functions, produce virions which are essentially physically and functionally equivalent, and replicate and assemble by practically identical mechanisms. AAV serotypes 1-6 and 7-9 are defined as "true" serotypes, in that they do not efficiently cross-react with neutralizing sera specific for all other existing and characterized serotypes. In contrast, AAV serotypes 6, 10 (also referred to as Rh10), and 11 are considered "variant" serotypes as they do not adhere to the definition of a "true" serotype. AAV serotype 2 (AAV2) has been used extensively for gene therapy applications due to its lack of pathogenicity, wide range of infectivity, and ability to establish long-term transgene expression (see, e.g., Carter, B. J., Hum. Gene Ther., 16: 541-550 (2005); and Wu et al., supra). Genome sequences of various AAV serotypes and comparisons thereof are disclosed in, for example, GenBank Accession numbers U89790, J01901, AF043303, and AF085716; Chiorini et al., J. Virol., 71: 6823-33 (1997); Srivastava et al., J. Virol., 45: 555-64 (1983); Chiorini et al., J. Virol., 73: 1309-1319 (1999); Rutledge et al., J. Virol., 72: 309-319 (1998); and Wu et al., J. Virol., 74: 8635-47 (2000)).

AAV rep and ITR sequences are particularly conserved across most AAV serotypes. For example, the Rep78 proteins of AAV2, AAV3A, AAV3B, AAV4, and AAV6 are reportedly about 89-93% identical (see Bantel-Schaal et al., J. Virol., 73(2): 939-947 (1999)). It has been reported that AAV serotypes 2, 3A, 3B, and 6 share about 82% total nucleotide sequence identity at the genome level (Bantel-Schaal et al., supra). Moreover, the rep sequences and ITRs of many AAV serotypes are known to efficiently cross-complement (i.e., functionally substitute) corresponding sequences from other serotypes during production of AAV particles in mammalian cells.

Generally, the cap proteins, which determine the cellular tropicity of the AAV particle, and related cap protein-encoding sequences, are significantly less conserved than Rep genes across different AAV serotypes. In view of the ability Rep and ITR sequences to cross-complement corresponding sequences of other serotypes, the AAV vector can comprise a mixture of serotypes and thereby be a "chimeric" or "pseudotyped" AAV vector. A chimeric AAV vector typically comprises AAV capsid proteins derived from two or more (e.g., 2, 3, 4, etc.) different AAV serotypes. In contrast, a pseudotyped AAV vector comprises one or more ITRs of one AAV serotype packaged into a capsid of another AAV serotype. Chimeric and pseudotyped AAV vectors are further described in, for example, U.S. Pat. No. 6,723,551; Flotte, Mol. Ther., 13(1): 1-2 (2006); Gao et al., J. Virol., 78: 6381-6388 (2004); Gao et al., Proc. Natl. Acad. Sci. USA, 99: 11854-11859 (2002); De et al., Mol. Ther., 13: 67-76 (2006); and Gao et al., Mol. Ther., 13: 77-87 (2006).

In one embodiment, the AAV vector is generated using an AAV that infects humans (e.g., AAV2). Alternatively, the AAV vector is generated using an AAV that infects non-human primates, such as, for example, the great apes (e.g., chimpanzees), Old World monkeys (e.g., macaques), and New World monkeys (e.g., marmosets). Preferably, the AAV vector is generated using an AAV that infects a non-human primate pseudotyped with an AAV that infects humans. Examples of such pseudotyped AAV vectors are disclosed in, e.g., Cearley et al., Molecular Therapy, 13: 528-537 (2006). In one embodiment, an AAV vector can be generated which comprises a capsid protein from an AAV that infects rhesus macaques pseudotyped with AAV2 inverted terminal repeats (ITRs). In a particularly preferred embodiment, the inventive AAV vector comprises a capsid protein from AAV10 (also referred to as "AAVrh.10"), which infects rhesus macaques pseudotyped with AAV2 ITRs (see, e.g., Watanabe et al., Gene Ther., 17(8): 1042-1051 (2010); and Mao et al., Hum. Gene Therapy, 22: 1525-1535 (2011)).

An AAV vector, as disclosed herein, comprises a nucleic acid sequence encoding a dominant negative SARM1 polypeptide. "Nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides.

In some embodiments, a vector comprising a nucleic acid sequence encoding a dominant negative SARM1 can be a plasmid, cosmid, yeast artificial chromosome (YAC), bacterial artificial chromosome (BAC), viral vector or bacteriophage. The vectors can provide for replication of dominant negative SARM1 nucleic acids, expression of dominant negative SARM1 polypeptides or integration of dominant negative SARM1 nucleic acids into the chromosome of a host cell. The choice of vector is dependent on the desired purpose. Certain cloning vectors are useful for cloning, mutation and manipulation of the dominant negative SARM1 nucleic acid. Other vectors are useful for expression of the dominant negative SARM1 polypeptide, being able to express the polypeptide in large amounts for purification purposes or to express the dominant negative SARM1 polypeptide in a temporal or tissue specific manner, for example, expression of dominant negative SARM1 only in neurons. The vector can also be chosen on the basis of the host cell, e.g., to facilitate expression in bacteria, mammalian cells, insect cells, fish cell (e.g., zebrafish) and/or amphibian cells. The choice of matching vector to host cell is apparent to one of skill in the art, and the types of host cells are discussed below. Many vectors or vector systems are available commercially, for example, the pET bacterial expression system (Invitrogen™, Carlsbad Calif.).

The vectors disclosed herein can be viral or non-viral vectors. For example, the disclosed vectors can be viral vectors. Specifically, the disclosed vectors can be adenoviral vectors. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasm ids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain neurodegenerative diseases or disorders and cell populations by using the targeting characteristics of the carrier.

Vectors can include various components including, but not limited to, an origin of replication, one or more marker or selectable genes (e.g. GFP, neo), promoters, enhancers, terminators, poly-adenylation sequences, repressors or activators. Such elements are provided in the vector so as to be operably linked to the coding region of the dominant negative SARM1-encoding nucleic acid, thereby facilitating expression in a host cell of interest. Cloning and expression vectors can contain an origin of replication which allows the vector to replicate in the host cells. Vectors can also include a selectable marker, e.g., to confer a resistance to a drug or compliment deficiencies in growth. Examples of drug resistance markers include, but are not limited to, ampicillin, tetracycline, neomycin or methotrexate. Examples of other marker genes can be the fluorescent polypeptides such one of the members of the fluorescent family of proteins, for example, GFP, YFP, BFP, RFP etc. These markers can be contained on the same vector as the gene of interest or can be on separate vectors and co-transfected with the vector containing the gene of interest.

The vector can contain a promoter that is suitable for expression of the dominant negative SARM1 in mammalian cells, which promoter can be operably linked to provide for inducible or constitutive expression of a dominant negative SARM1 peptide. Exemplary inducible promoters include, for example, the metallothionine promoter or an ecdysone-responsive promoter. Exemplary constitutive promoters include, for example, the viral promoters from cytomegalovirus (CMV), Rous Sarcoma virus (RSV), Simian virus 40 (SV40), avian sarcoma virus, the beta-actin promoter and the heat-shock promoters. The promoter can be chosen for its tissue specificity. Certain promoters only express in certain tissues, and when it is desirable to express the polypeptide of interest only in a selected tissue, one of these promoters can be used. For example, the synapsin 1 gene promoter was used in a recombinant adenoviral vector system to express therapeutic proteins only in neuronal cells (Kugler et al., *Mol Cell Neurosci.* (2001) 17(1):78-96). The choice of promoter will be apparent to one of skill in the art for the desired host cell system.

The vector encoding dominant negative SARM1 can be a viral vector. Examples of viral vectors include retroviral vectors, such as: adenovirus, simian virus 40 (SV40), cytomegalovirus (CMV), Moloney murine leukemia virus (Mo-MuLv), Rous Sarcoma Virus (RSV), lentivirus, herpesvirus, poxvirus and vaccinia virus. A viral vector can be used to facilitate expression in a target cell, e.g., for production of dominant negative SARM1 or for use in therapy (e.g., to deliver dominant negative SARM1 to a patient by expression from the vector). Where used for therapy, dominant negative SARM1-encoding vectors (e.g, viral vectors), can be administered directly to the patient via an appropriate route or can be administered using an ex vivo strategy using patient cells (autologous) or allogeneic cells, which are suitable for administration to the patient to be treated.

As used herein, plasm id or viral vectors are agents that transport the disclosed nucleic acids, such as a nucleic acid sequence capable of encoding one or more of the disclosed peptides into the cell without degradation and include a promoter yielding expression of the gene in the cells into which it is delivered. In some embodiments the nucleic acid sequences disclosed herein are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. The viral vectors may be formulated in pharmaceutical compositions as those described above. Additionally, viral vectors may be formulated for direct delivery to the central nervous system, outside the blood/brain barrier, inside the blood/brain barrier, or any combination thereof. The viral vector may be formulated for administration via intrathecal, intravenous or intracranial injection. The viral vector may be in the form of an isolated viral particle.

Retroviral vectors, in general, are described by Verma, I. M., Retroviral vectors for gene transfer. In Microbiology, Amer. Soc. for Microbiology, pp. 229-232, Washington, (1985), which is hereby incorporated by reference in its entirety. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference in their entirety for their teaching of methods for using retroviral vectors for gene therapy.

Other useful systems include, for example, replicating and host-restricted non-replicating vaccinia virus vectors. In addition, the disclosed nucleic acid sequences can be delivered to a target cell in a non-nucleic acid based system. For example, the disclosed polynucleotides can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed expression vectors, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a peptide and a cationic liposome can be administered to the blood, to a target organ, or inhaled into the respiratory tract to target cells of the respiratory tract. For example, a composition comprising a peptide or nucleic acid sequence described herein and a cationic liposome can be administered to a subjects lung cells. Regarding liposomes, see, e.g., Brigham et al. Am. J. Resp. Cell. Mol. Biol. 1:95-100 (1989); Feigner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

Host cells modified to provide for expression of a dominant negative SARM1 peptide disclosed herein are also contemplated. Such host cells can be modified to express a dominant negative SARM1 peptide from either an episomal or genomically integrated nucleic acid. Such host cells can be produced by any suitable method, e.g., electroporation, transfection or transformation with a vector encoding a dominant negative SARM1 peptide. Host cells can be selected according to a desired use (e.g., mammalian cell expression), and modified to provide for dominant negative SARM1 expression according to methods well known in the art. Techniques for introducing the vectors into host cells and subsequent culture of the host cells are well known in the art.

Host cells (e.g., mammalian host cells) suitable for replication and expression of dominant negative SARM1 containing vectors are provided, wherein the cells may be stably or transiently transfected and/or stably or transiently express a dominant negative SARM1. Such dominant negative SARM1-expressing mammalian cells find use in, for example, production of a dominant negative SARM1 polypeptide. Production of dominant negative SARM1 in mammalian cells can provide for post-translational modifications of dominant negative SARM1 and/or heterologous amino acids to which it may be fused (e.g., glycosylation, cleavage of signal peptide (if present)). In addition, mammalian cell lines can be selected for use in replicating, packaging and producing high titers of virus particles which contain a dominant negative SARM1 of interest or nucleic acid-encoding dominant negative SARM1. Such dominant negative SARM1 containing viruses can then be used to provide for delivery of dominant negative SARM1-encoding nucleic acids and dominant negative SARM1 peptides to a subject in need thereof.

Exemplary host cells include bacteria, yeast, mammalian cells (e.g., human cells or cell lines), insect cells, and the like. Examples of bacterial host cells include *E. coli* and other bacteria which can find use in cloning, manipulation and production of dominant negative SARM1 nucleic acids or the production of dominant negative SARM1 polypeptide. Examples of mammalian cells include, but are not limited to, Chinese hamster ovary (CHO) cells, HEK 293 cells, human cervical carcinoma cells (Hela), canine kidney cells (MDCK), human liver cells (HepG2), baby hamster kidney cells (BHK), and monkey kidney cells (CV1).

(b) Compositions Comprising Dominant Negative SARM1

The present disclosure also provides pharmaceutical compositions. The pharmaceutical composition comprises a dominant negative SARM1, as an active ingredient, and at least one pharmaceutically acceptable excipient. In some embodiments, the present disclosure provides a composition comprising, consisting essentially of, or consisting of the above-described AAV vector and a pharmaceutically acceptable (e.g. physiologically acceptable) carrier. When the composition consists essentially of the inventive AAV vector and a pharmaceutically acceptable carrier, additional components can be included that do not materially affect the composition (e.g., adjuvants, buffers, stabilizers, anti-inflammatory agents, solubilizers, preservatives, etc.). When the composition consists of the inventive AAV vector and the pharmaceutically acceptable carrier, the composition does not comprise any additional components. Any suitable carrier can be used within the context of the invention, and such carriers are well known in the art. The choice of carrier will be determined, in part, by the particular site to which the composition may be administered and the particular method used to administer the composition. The composition optionally can be sterile with the exception of the AAV vector described herein. The composition can be frozen or lyophilized for storage and reconstituted in a suitable sterile carrier prior to use. The compositions can be generated in accordance with conventional techniques described in, e.g., Remington: The Science and Practice of Pharmacy, 21st Edition, Lippincott Williams & Wilkins, Philadelphia, Pa. (2001).

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the AAV vector is administered in a composition formulated to protect the AAV vector from damage prior to administration. For example, the composition can be formulated to reduce loss of the AAV vector on devices used to prepare, store, or administer the AAV vector, such as glassware, syringes, or needles. The composition can be formulated to decrease the light sensitivity and/or temperature sensitivity of the AAV vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the AAV vector, facilitate administration, and increase the efficiency of the inventive method. Formulations for AAV vector-containing compositions are further described in, for example, Wright et al., Curr. Opin. Drug Discov. Devel., 6(2): 174-178 (2003) and Wright et al., Molecular Therapy, 12: 171-178 (2005))

The composition also can be formulated to enhance transduction efficiency. In addition, one of ordinary skill in the art will appreciate that the AAV vector can be present in a composition with other therapeutic or biologically-active agents. For example, factors that control inflammation, such as ibuprofen or steroids, can be part of the composition to reduce swelling and inflammation associated with in vivo administration of the AAV vector. Thus, in addition to the therapies described herein, one may also provide to the subject other therapies known to be efficacious for treatment of the disease, disorder, or condition. In some embodiments, the additional drug or therapeutic agent may be a small molecule, a polypeptide, a nucleic acid, a cell or parts thereof, and antibody or the like. In some embodiments, the administration of a dominant negative SARM1 may be administered before concurrently or after administration of an additional drug or therapeutic agent.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.
(i) Diluent In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methyl-cellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.
(ii) Binder In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.
(iii) Filler In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.
(iv) Buffering Agent In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).
(v) pH Modifier In various embodiments, the excipient may be a pH modifier. By way of non-limiting example, the pH modifying agent may be sodium carbonate, sodium bicarbonate, sodium citrate, citric acid, or phosphoric acid.
(vi) Disintegrant In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palm itate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A.R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules. The composition can be administered in or on a device that allows controlled or sustained release, such as a sponge, biocompatible meshwork, mechanical reservoir, or mechanical implant. Implants (see, e.g., U.S. Pat. No. 5,443, 505), devices (see, e.g., U.S. Pat. No. 4,863,457), such as an implantable device, e.g., a mechanical reservoir or an implant or a device comprised of a polymeric composition, are particularly useful for administration of the AAV vector. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a poly-lactic-glycolic acid.

(c) Administration (i) Dosage Forms

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intraocular, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising the a dominant negative SARM1., is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

Generally, a safe and effective amount of a composition comprising a dominant negative SARM1 is, for example, that amount that would cause the desired therapeutic effect in a subject while minimizing undesired side effects. In various embodiments, an effective amount of a composition comprising a dominant negative SARM1 described herein can substantially inhibit endogenous SARM1 activity and treat associated diseases. In some embodiments, an effective amount is an amount capable of inhibiting, delaying, or reducing SARM1-mediated axon degeneration. In some embodiments, a dominant negative SARM1 or dominant negative SARM1 composition leads to a degeneration index of about 0.5, about 0.45, about 0.4, about 0.35, about 0.3, about 0.25, about 0.2, about 0.15, about 0.1, about 0.5 or about 0.01. In some embodiments, the composition comprising a dominant negative SARM1 molecule leads to a degeneration index of about 0.4 or below at 36 hours, at 48 hours, at 72 hours, at 96 hours, at 120 hours or longer after axotomy. In some embodiments, compositions provided herein contain and/or deliver an amount of a dominant negative SARM1 that is effective to measurably inhibit endogenous SARM1 activity and/or treat, and/or decrease the infectivity, morbidity, and rate of mortality associated with a disease or disorder associated with axon degeneration in a subject when administered to the subject in an appropriate dosing regimen.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the LD50 (the dose lethal to 50% of the population) and the ED50, (the dose therapeutically effective in 50% of the population). The dose ratio between toxic and therapeutic effects is the therapeutic index that can be expressed as the ratio LD50/ED50, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Shargel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a composition comprising a dominant negative SARM1 can occur as a single event or over a time course of treatment. For example, a composition comprising a dominant negative SARM1 can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

(II) Methods

The present disclosure encompasses a method of measurably inhibiting the activity of an endogenously expressed SARM1 polypeptide. The present disclosure provides methods of inhibiting SARM1 activity use in vitro, in vivo, in situ or ex vivo. Generally, the method comprises administration of an effective amount of dominant negative SARM1 or a composition comprising a dominant negative SARM1, so as to down-regulate the activity of an endogenously expressed SARM1 polypeptide. In some embodiments, the dominant negative SARM1 or the composition comprising a dominant negative SARM1 is administered to a biological sample. The term "biological sample", as used herein, includes, without limitation, tissues, cells, cell cultures or extracts thereof; biopsied material obtained from a subject or extracts thereof; and blood, saliva, urine, feces, semen, tears, or other body fluids or extracts thereof. In some embodiments, dominant negative SARM1 or a composition comprising a dominant negative SARM1 is administered to a subject in need thereof. Suitable dominant negative SARM1 molecules or compositions comprising a dominant negative SARM1 are disclosed herein, for instance those described in Section I.

In one aspect of the present disclosure provides a method of inhibiting endogenously expressed SARM1 activity, thereby treating a neurodegenerative or neurological disease in a subject in need thereof. In general, the method comprises administering a therapeutically effective amount of a composition comprising a dominant negative SARM1. In some embodiments, the methods include administering a therapeutically effective amount of a composition comprising an AAV comprising a nucleic acid sequence encoding a dominant negative SARM1 to a subject. The dominant negative SARM1 molecules as described herein are useful in decreasing the infectivity, morbidity, and/or rate of mortality associated with a variety of axon degeneration mediated diseases and disorders. As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

For a predisposition to a neurodegenerative or neurological disease, a dominant negative SARM1 can be administered on a prophylactic basis. An effective amount of dominant negative SARM1 that will prevent or slow the progression of a neurodegenerative or neurological disease is known as a "prophylactic effective dose." The prophylactic effective dose will depend on the factors of weight, age, administration route, and seriousness of the predisposition. The dose can be lower or the same as the effective dose used in treating diagnosed neurodegenerative or neurological disease.

In one aspect, administration of a dominant negative SARM1 or a composition comprising a dominant negative SARM1 transiently prevents axon degeneration in a subject in need thereof. In some embodiments, a dominant negative SARM1 or a composition comprising a dominant negative SARM1 is administered one day, two days, three days, four days, five days, six days, one week, two weeks, three weeks, a month, six weeks, two months, three months, four months, five months, six months or more, before or after axon injury or damage. In some embodiments, administration of a dominant negative SARM1 or a composition comprising a dominant negative SARM1 leads to about 50% normal fiber content, about 60% normal fiber content, about 70% normal fiber content, about 80% normal fiber content, about 90% normal fiber content, or about 95% or more normal fiber content In some embodiments, the neurodegenerative or neurological disease or disorder is associated with axonal degeneration, axonal damage, axonopathy, a demyelinating disease, a central pontine myelinolysis, a nerve injury disease or disorder, a metabolic disease, a mitochondrial disease, metabolic axonal degeneration, axonal damage resulting from a leukoencephalopathy or a leukodystrophy. In some embodiments, the neurodegenerative or neurological disease or disorder is selected from the group consisting of diabetic peripheral neuropathy, inherited neuropathy, acute angle glaucoma, spinal cord injury, stroke, multiple sclerosis, progressive multifocal leukoencephalopathy, congenital hypomyelination, encephalomyelitis, acute disseminated encephalomyelitis, central pontine myelolysis, osmotic hyponatremia, hypoxic demyelination, ischemic demyelination, adrenoleukodystrophy, Alexander's disease, Niemann-Pick disease, Pelizaeus Merzbacher disease, periventricular leukomalacia, globoid cell leukodystrophy (Krabbe's disease), Wallerian degeneration, optic neuritis, transverse myelitis, amyotrophic lateral sclerosis (ALS, Lou Gehrig's disease), Huntington's disease, Alzheimer's disease, Parkinson's disease, Tay-Sacks disease, Gaucher's disease, Hurler Syndrome, traumatic brain injury, post radiation injury, neurologic complications of chemotherapy (chemotherapy induced neuropathy; CIPN), neuropathy, acute ischemic optic neuropathy, vitamin B12 deficiency, isolated vitamin E deficiency syndrome, Bassen-Kornzweig syndrome, Glaucoma, Leber's hereditary optic atrophy, Leber congenital amaurosis, neuromyelitis optica, metachromatic leukodystrophy, acute hemorrhagic leukoencephalitis, trigeminal neuralgia, Bell's palsy, cerebral ischemia, multiple system atrophy, traumatic glaucoma, tropical spastic paraparesis human T-lymphotropic virus 1 (HTLV-1) associated myelopathy, west nile virus encephalopathy, La Crosse virus encephalitis, Bunyavirus encephalitis, pediatric viral encephalitis, essential tremor, Charcot-Marie-Tooth disease, motorneuron disease, spinal muscular atrophy (SMA), hereditary sensory and autonomic neuropathy (HSAN), adrenomyeloneuropathy, progressive supra nuclear palsy (PSP), Friedrich's ataxia, hereditary ataxias, noise induced hearing loss and congenital hearing loss.

According to another embodiment, the invention provides a composition comprising dominant negative SARM1 molecule, and a pharmaceutically acceptable carrier, adjuvant, or vehicle. In some embodiments the amount of dominant negative SARM1 provided by the therapeutic compositions of this invention are effective to measurably inhibit endogenous SARM1 activity and/or treat a neurodegenerative or neurological disease, in a biological sample or in a subject. In some embodiments, compositions provided herein contain and/or deliver an amount of a composition comprising a dominant negative SARM1 molecule that is effective to measurably inhibit SARM1 activity in a biological sample. In some embodiments, compositions provided herein contain and/or deliver an amount of a dominant negative SARM1 molecule that is effective to measurably inhibit such SARM1 activity and/or treat, and/or decrease the axonal degradation, morbidity, and rate of mortality associated with an neurodegenerative or neurological disease or disorder in a subject when administered to the subject in an appropriate dosing regimen. In certain embodiments, a composition of this invention is formulated for administration to a subject in need of such composition. In some embodiments, a composition of this invention is formulated for injectable administration to a subject.

Methods described herein are generally performed on a subject in need thereof. A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

(III) Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to compositions and pharmaceutical formulations comprising dominant negative SARM1 molecule, as described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions

It is to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Here, the inventors introduce point mutations into human SARM1 and expressed the constructs in wildtype neurons with the goal to identify SARM1 dominant-negatives that potently inhibit SARM1 function. The inventors have unexpectedly found several SARM1 single mutants that strongly inhibit AxD in vitro. Surprisingly, combining the best two of these yields a dominant-negative that potently inhibits SARM1 enzymatic function and that protects axons in cellular models of axotomy and neuropathy as robustly as SARM1 knock-out neurons. Using adeno-associated virus mediated expression of this optimized construct in adult wildtype mice and sciatic nerve cut as a model of most severe AxD, the inventors demonstrate axon preservation similar to that observed in SARM1 knock-out mice. Thus, provided is a novel strategy to effectively and enduringly inhibit SARM1 function in vivo. AAV mediated expression of SARM1-dominant negatives represents a therapeutic option to block pathological AxD and improve functional outcomes in neuropathies and likely other diseases characterized by acute and chronic axonal degeneration. Unlike traditional gene therapy that seeks to treat a single, genetic disorder, gene therapy targeting SARM1 has the potential to treat a wide range of diseases characterized by a shared pathological process—axon loss.

Figure 1B:
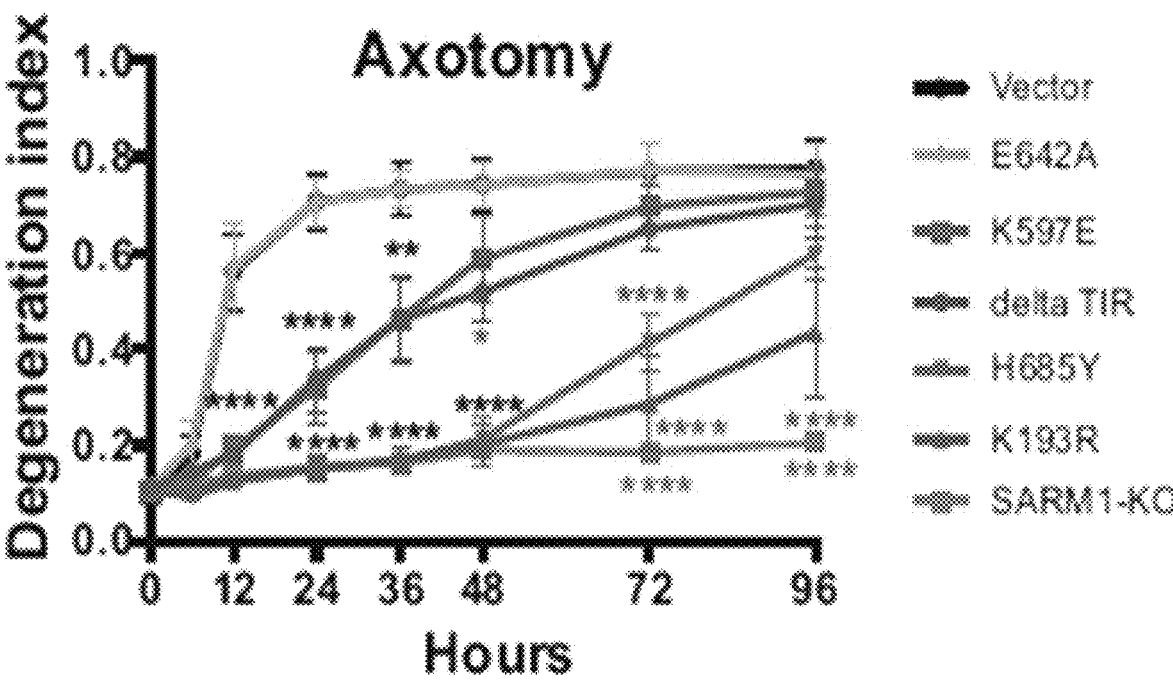
Figure 1C:
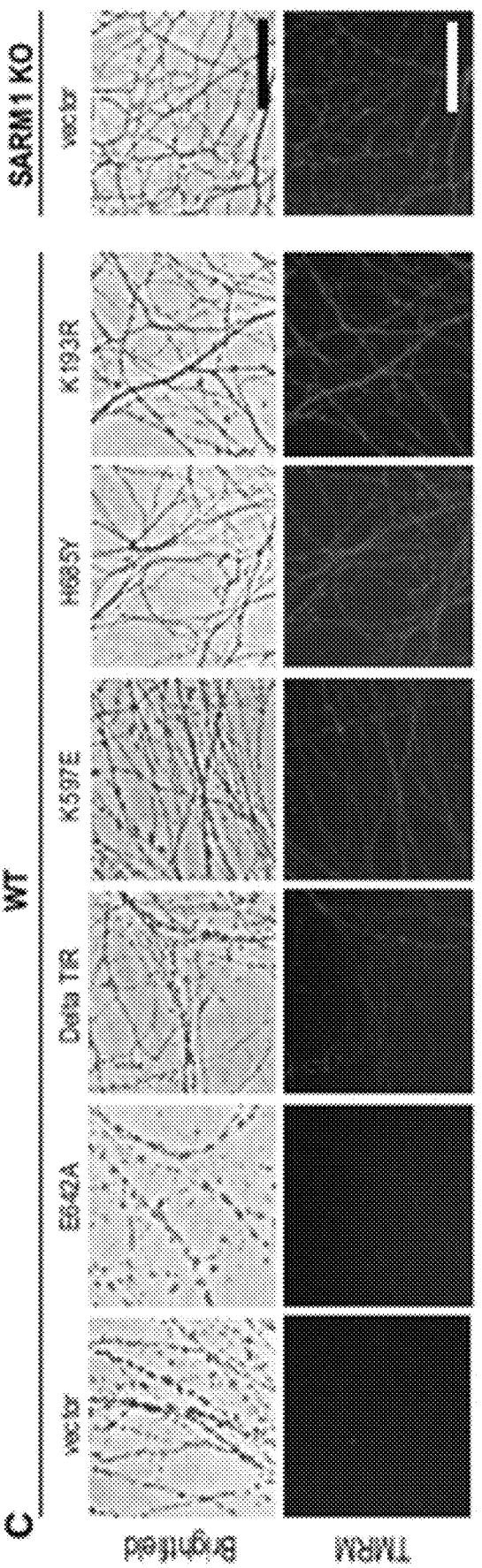
Figure 5A:
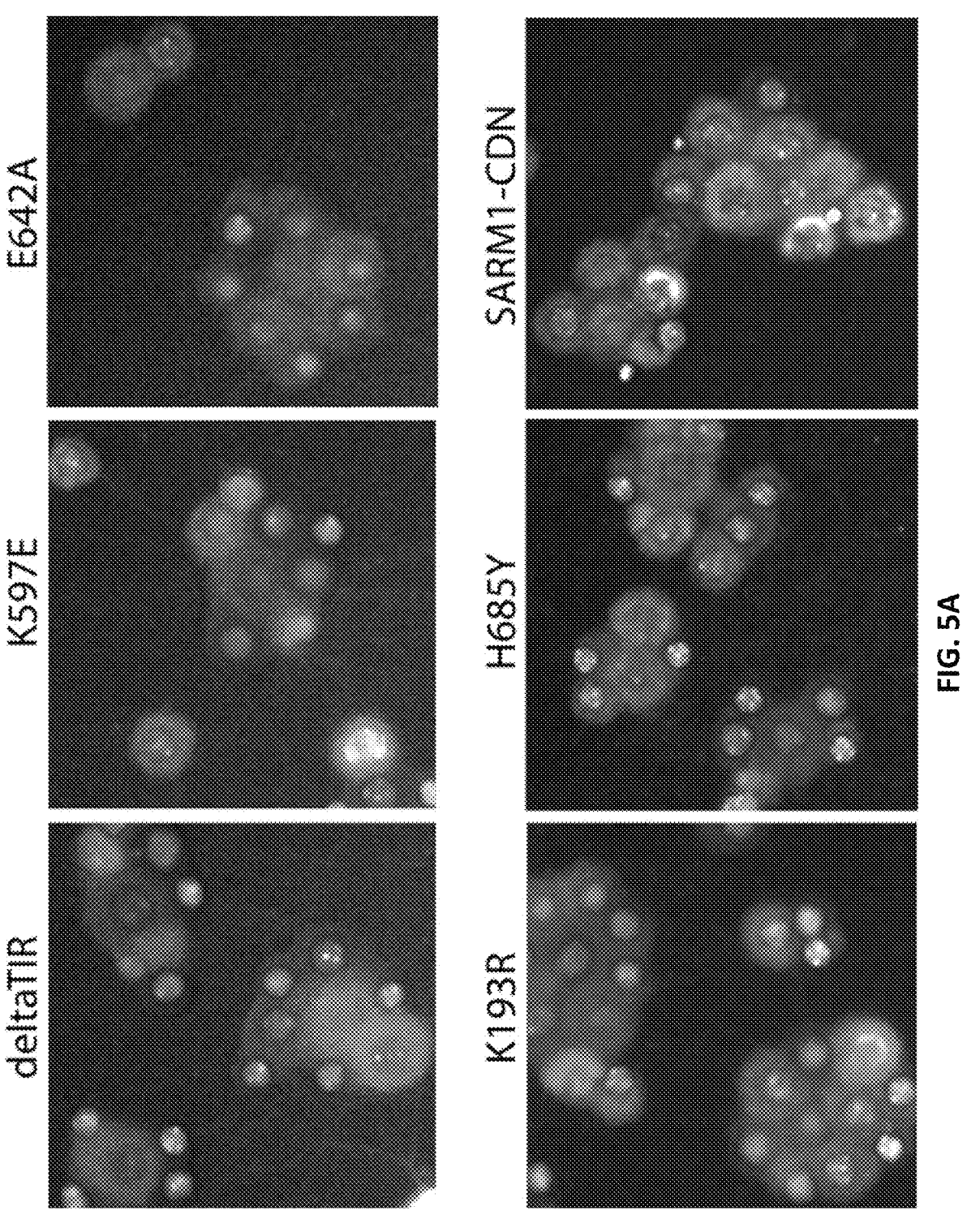
FIG. 5A and FIG. 5B Transduction efficiency of DRG neurons (FIG. 5A) Representative photomicrographs of DRG neurons transduced with lentivirus expressing SARM1 dominant-negative mutants tagged with venus (green) and counterstained with Hoechst 33342 to label nuclei (blue).
Figure 5B:
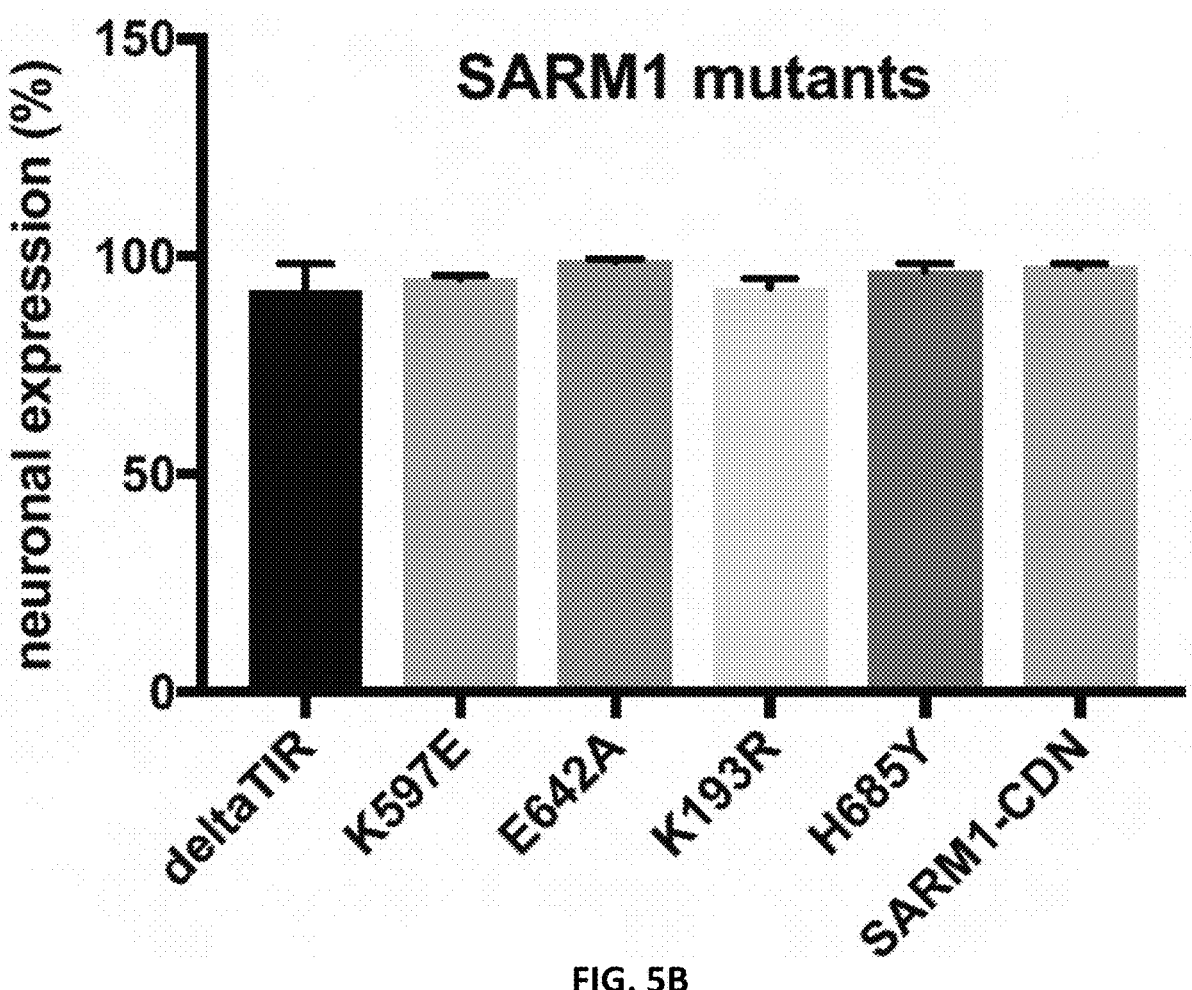
Figure 6A:
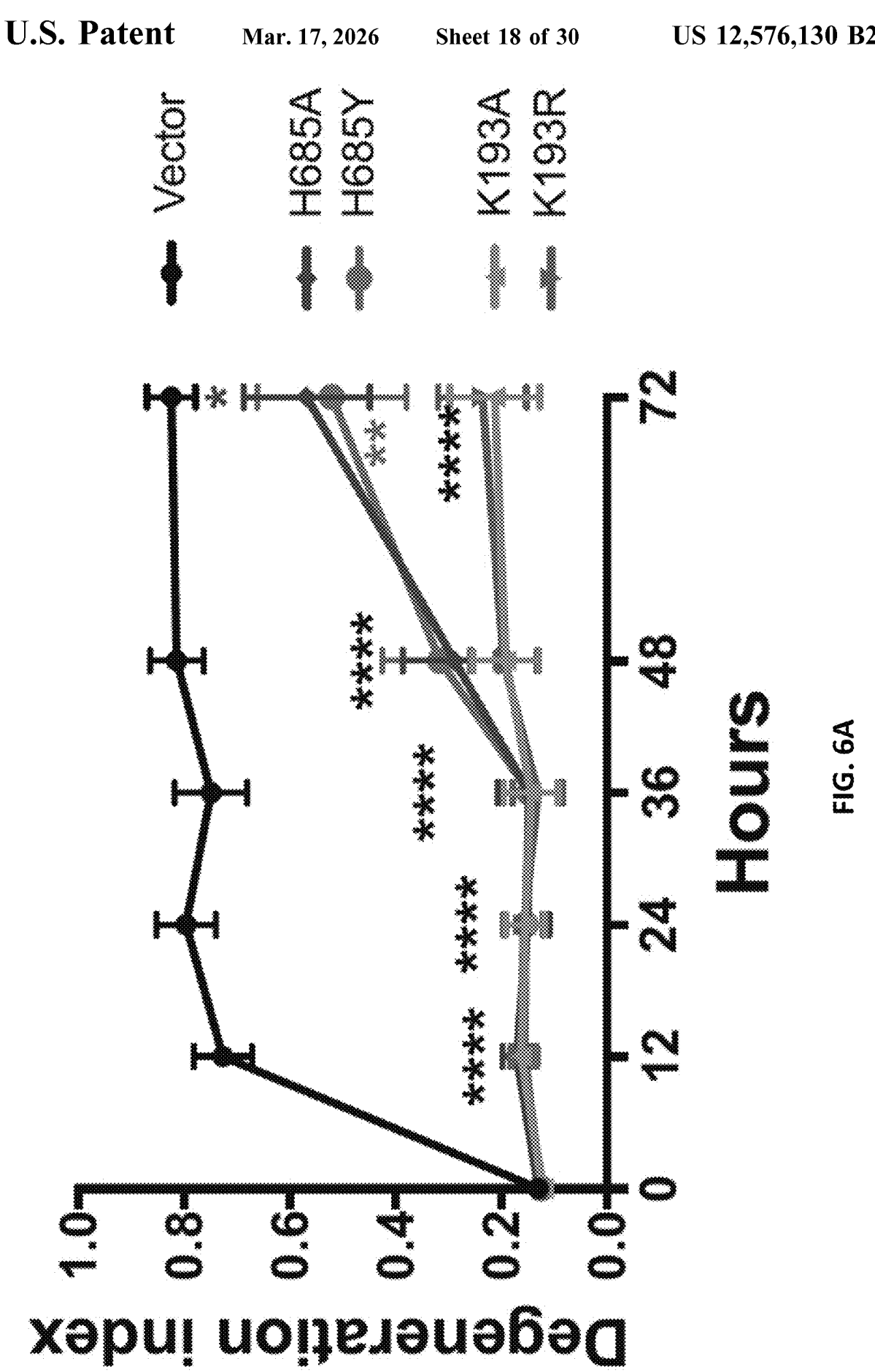
FIG. 6A and FIG. 6B show a comparison of SARM1 dominant-negative transgenes.
Figure 6B:
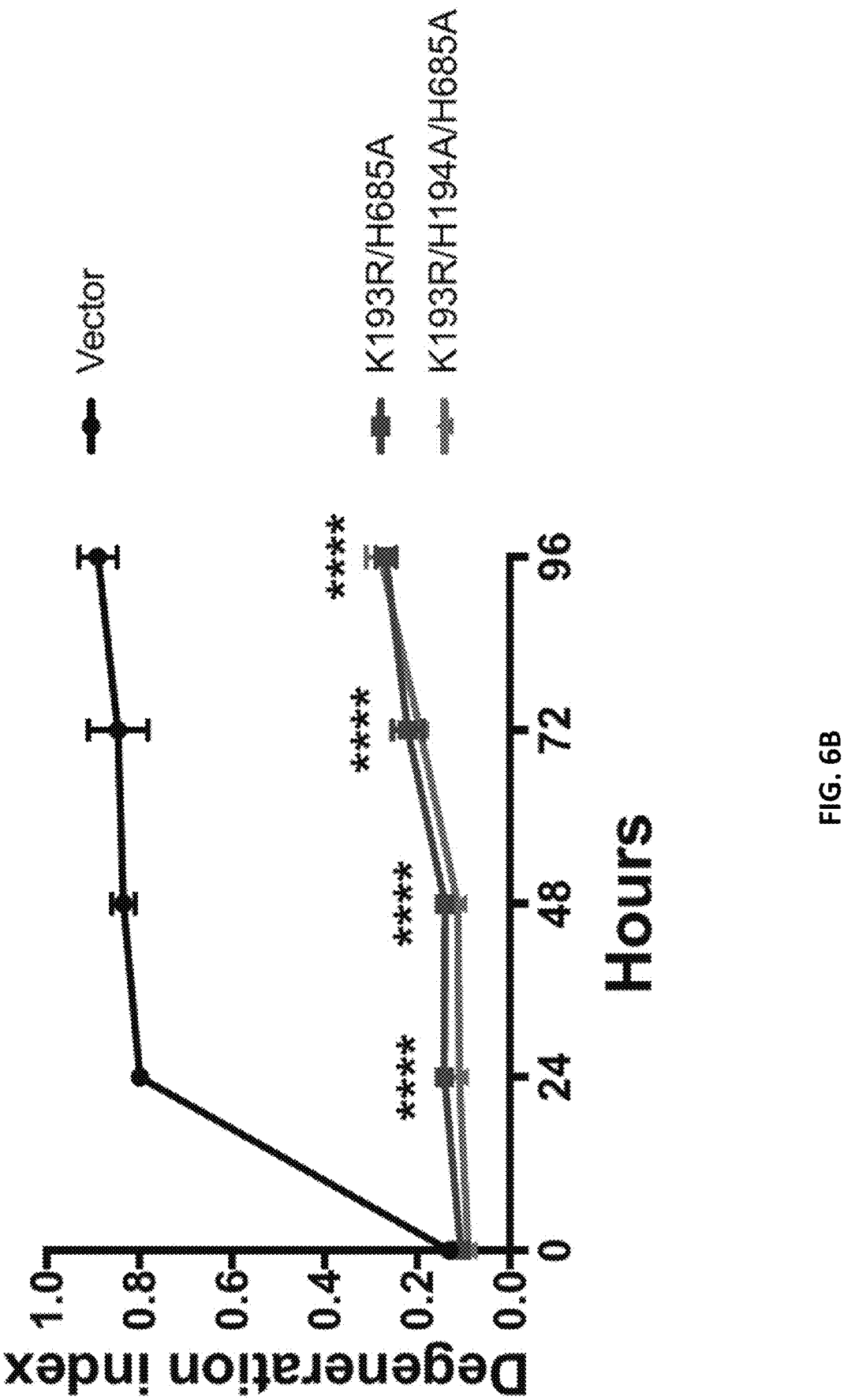

Example 1—Identification of SARM1 Dominant-Negative Mutants that Inhibit Axonal Degeneration To develop potent SARM1 dominant-negatives, individual point mutations were introduced in highly conserved regions of the N terminal- and TIR domains (FIG. 1A) and tested if lentivirus-mediated expression of these constructs decreases AxD. All constructs were well expressed in cultured dorsal root ganglion neurons (FIG. 5). Axons were severed and cell bodies removed to avoid axon-regrowth into the injury site. With the aid of high-throughput automated imaging and an automated AxD index (Sasaki et al., 2009), fragmentation of distal axons was assessed over time. Fragmentation of axons begins 6 hours after cut and is complete by 24 hours (FIG. 1B, FIG. 1C). Expression of the previously discovered dominant-negatives SARM1-K597E (Summers et al., 2016) and SARM1-deltaTIR (Gerdts et al., 2013) in wildtype DRG neurons delays AxD until 36 hours after axotomy (FIG. 1B, FIG. 1C). We recently identified glutamic acid E642 as the key catalytic residue within the active site of the TIR NADase (Essuman et al., 2017). To evaluate if blocking enzyme function would yield a potent dominant-negative, SARM1-E642A was expressed in wildtype neurons. Although SARM1-E642A is non-functional when expressed in SARM1-KO neurons (Essuman et al., 2017), when SARM1-E642A is expressed in wildtype neurons axon fragmentation proceeds with the same kinetics as in wildtype axons expressing EGFP-vector (FIG. 1B). Surprisingly, while the SARM1-E642A mutant is non-functional, it does not act as a dominant-negative, suggesting that it cannot disrupt TIR-TIR interactions that allow for activation of the wildtype TIR NADase. In contrast, introducing a point mutation at another highly conserved residue in the TIR domain, at position H685 (FIG. 1A), results in a dominant-negative that potently protects axons for 72 hours after axotomy (FIG. 1B, FIG. 1C). Mutating H685 to either Y or A yields constructs whose dominant negative efficacy is indistinguishable, suggesting that it is the loss of the H rather than the conversion to any particular amino acid that generates the dominant negative effect (FIG. 6). Therefore, this histidine is likely necessary for the TIR-TIR interaction involved in SARM1 activity. The strongest dominant-negative effect was observed when a lysine at 193 in the N terminus was mutated (FIG. 1A). This lysine is present within a highly conserved region of the N-terminus that we hypothesized could be necessary for injury-induced activation of SARM1. SARM1-K193R expression in wildtype DRGs potently protects axons for 72 hours after axotomy (FIG. 1B, FIG. 1C). As with H685, mutating K193 to either R or A generates constructs whose dominant negative activity is indistinguishable, suggesting that it is the loss of the lysine that blocks injury-induced activation of SARM1 (FIG. 6).

As a second index of neuronal health, the mitochondrial potential in severed axons using the fluorescent mitochondrial membrane indicator TMRM was examined. Activation of SARM1 causes a drop in mitochondrial membrane potential (Summers et al., 2016), which is indicated by loss of red fluorescence. In wildtype DRG neurons expressing EGFP-vector or SARM1-E642A, TMRM fluorescence is no longer observed 24 hours after axotomy (FIG. 1C). In contrast, TMRM-positive mitochondria are preserved in wildtype DRGs expressing the SARM1 dominant-negative mutations and in SARM1-KO DRGs (FIG. 1C), indicating the morphologically intact severed axons remain metabolically active.

Figure 1D:
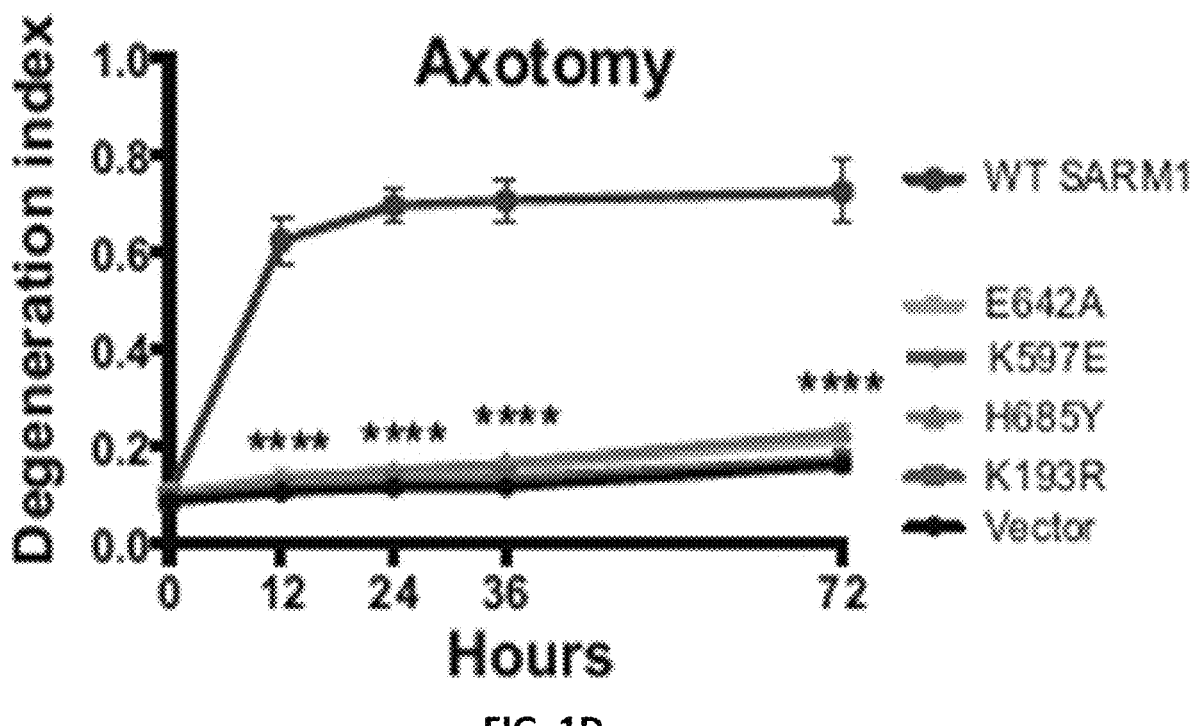
Figure 1E:
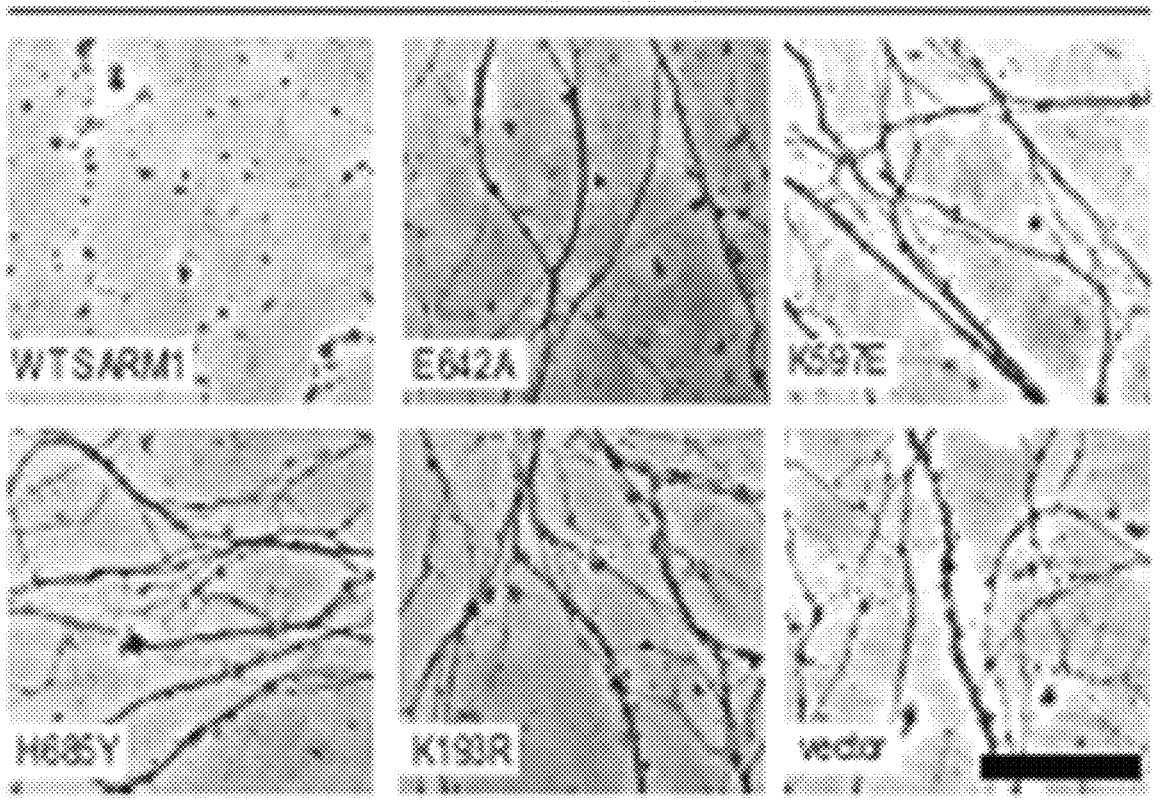

To evaluate whether these SARM1 mutants have pro-degenerative function on their own, we expressed either wildtype SARM1 or the SARM1 mutants (FIG. 1A) in cultured SARM1-KO DRG neurons and assessed AxD after axotomy. Axons of SARM1-KO neurons are completely intact for at least 72 hours after axotomy (FIG. 1D, FIG. 1E), whereas re-introducing enzymatically active wildtype SARM1 promotes rapid AxD after severing (FIG. 1D, FIG. 1E). In contrast, expression of the dominant-negative mutants and SARM1-E642A in SARM1-K0 DRGs does not induce AxD for at least 72 hours after transection (FIG. 1D, FIG. 1E) demonstrating that the evaluated SARM1 mutants do not possess pro-degenerative capabilities.

Figure 2A:
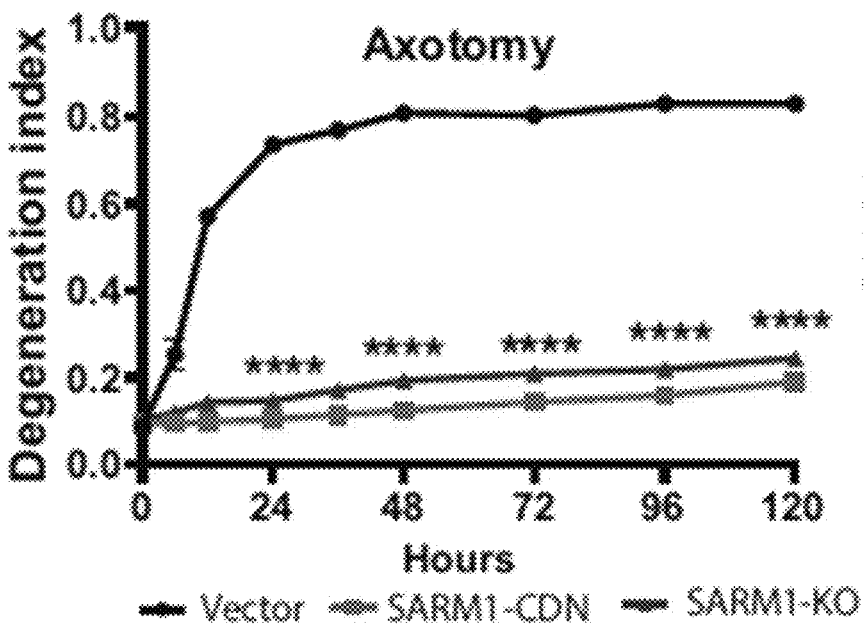
FIG. 2A, FIG. 2B, FIG. 2C, FIG. 2D, FIG. 2E and FIG. 2F show SARM1-CDN potently inhibits wildtype SARM1 function.
Figure 2B:
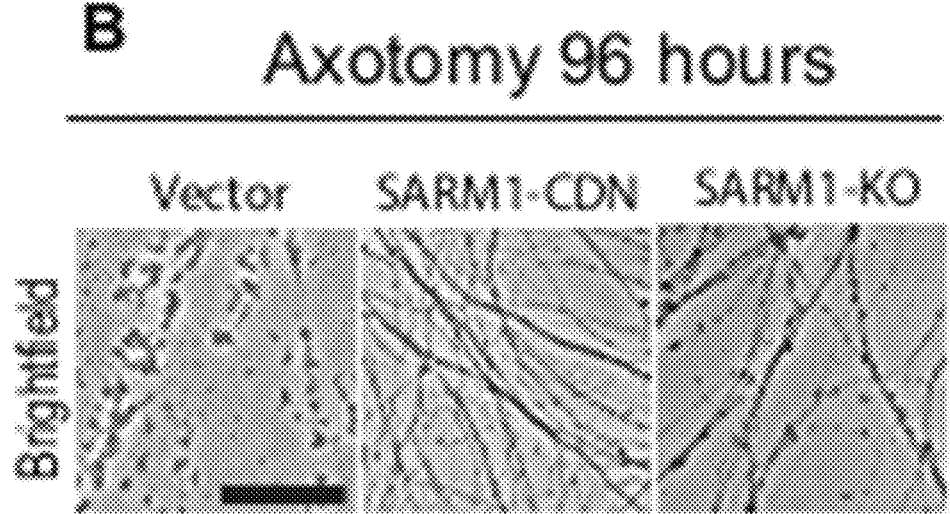
Figure 2C:
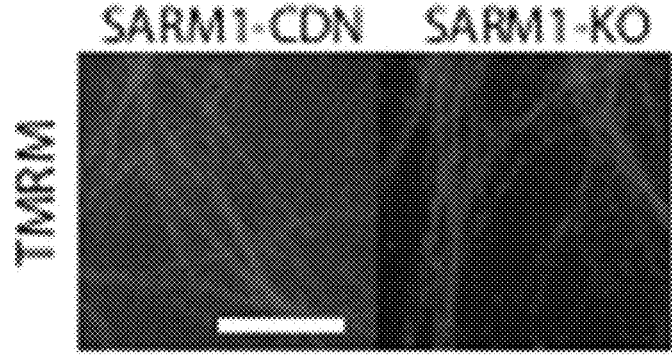
Figure 2D:
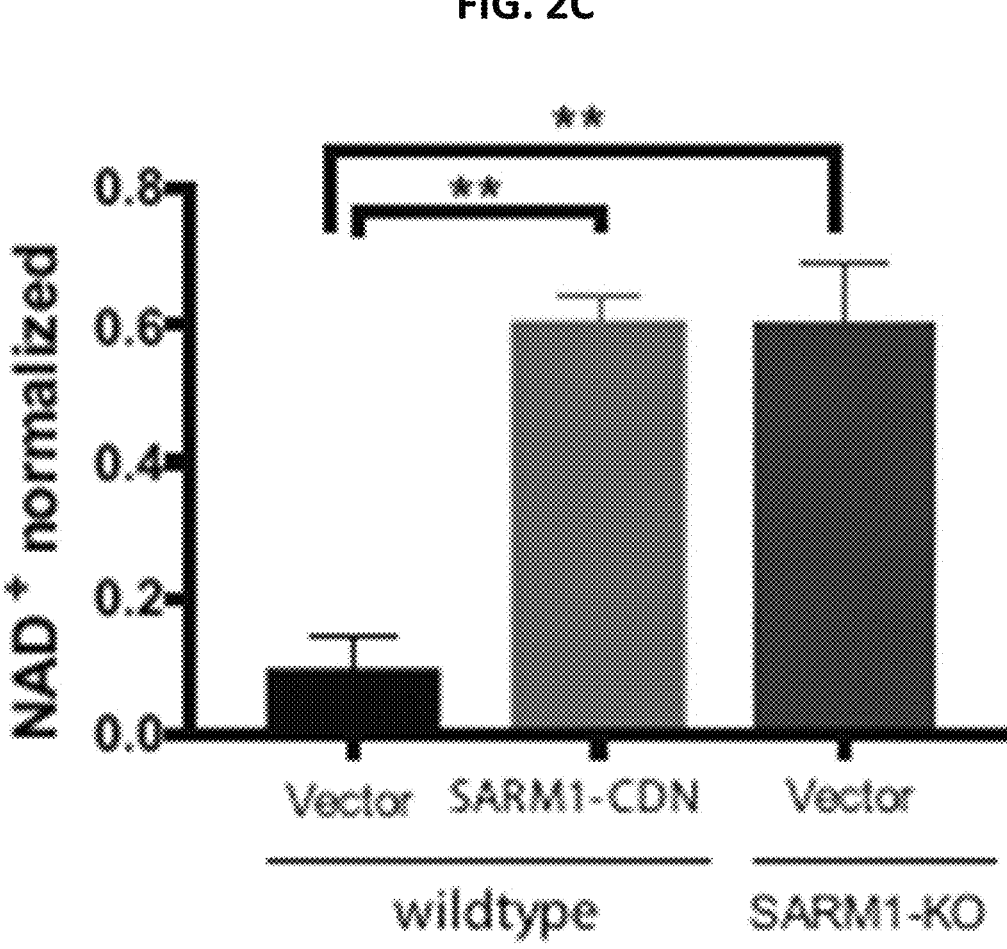

Example 2—Combining the SARM1-K193R and H685A Mutations Blocks Wildtype SARM1 Enzymatic Activity and Potently Protects from Axonal Degeneration in Cellular Models of Axotomy and Neuropathy Although expression of SARM1-K193R (FIG. 1B, FIG. 1C) and SARM1-H685A (FIG. 6A) strongly delays AxD after axotomy, the protection is less robust than deletion of SARM1 (FIG. 1B, FIG. 1C). We therefore evaluated whether a SARM1 molecule with mutations at both K193 and H685 would result in even more potent dominant negative activity. We generated a construct with both mutations as well as a third mutation, H194A, and we call this construct the SARM1-compound dominant negative (SARM1-CDN). Subsequent analysis demonstrated that addition of H194A does not impact the potency of SARM1-CDN (FIG. 6B), however since it was generated first and gave such a strong dominant negative effect, the remainder of our analysis is with SARM1-CDN. Expression of SARM1-CDN completely prevents AxD (FIG. 2A, FIG. 2B) and preserves TMRM-positive mitochondria (FIG. 2C) for at least 96 hours after axotomy. Upon activation, wildtype SARM1 rapidly degrades NAD+(Gerdts et al., 2015; Sasaki et al., 2016; Essuman et al., 2017), which results in local metabolic failure (Gerdts et al., 2015; Yang et al., 2015) and subsequent AxD. To assess whether SARM1-CDN also blocks this molecular activity of SARM1, axonal NAD+ levels in healthy and injured axons was measured. As expected, four hours after transection, NAD+ is largely depleted in wildtype neurons expressing a control vector (FIG. 2D). In contrast, NAD+ is maintained in wildtype neurons expressing SARM1-CDN and in SARM1-KO neurons (FIG. 2D). Hence, expression of SARM1-CDN in wildtype neurons potently blocks SARM1 enzymatic function and its pro-degenerative activity.

Figure 2E:
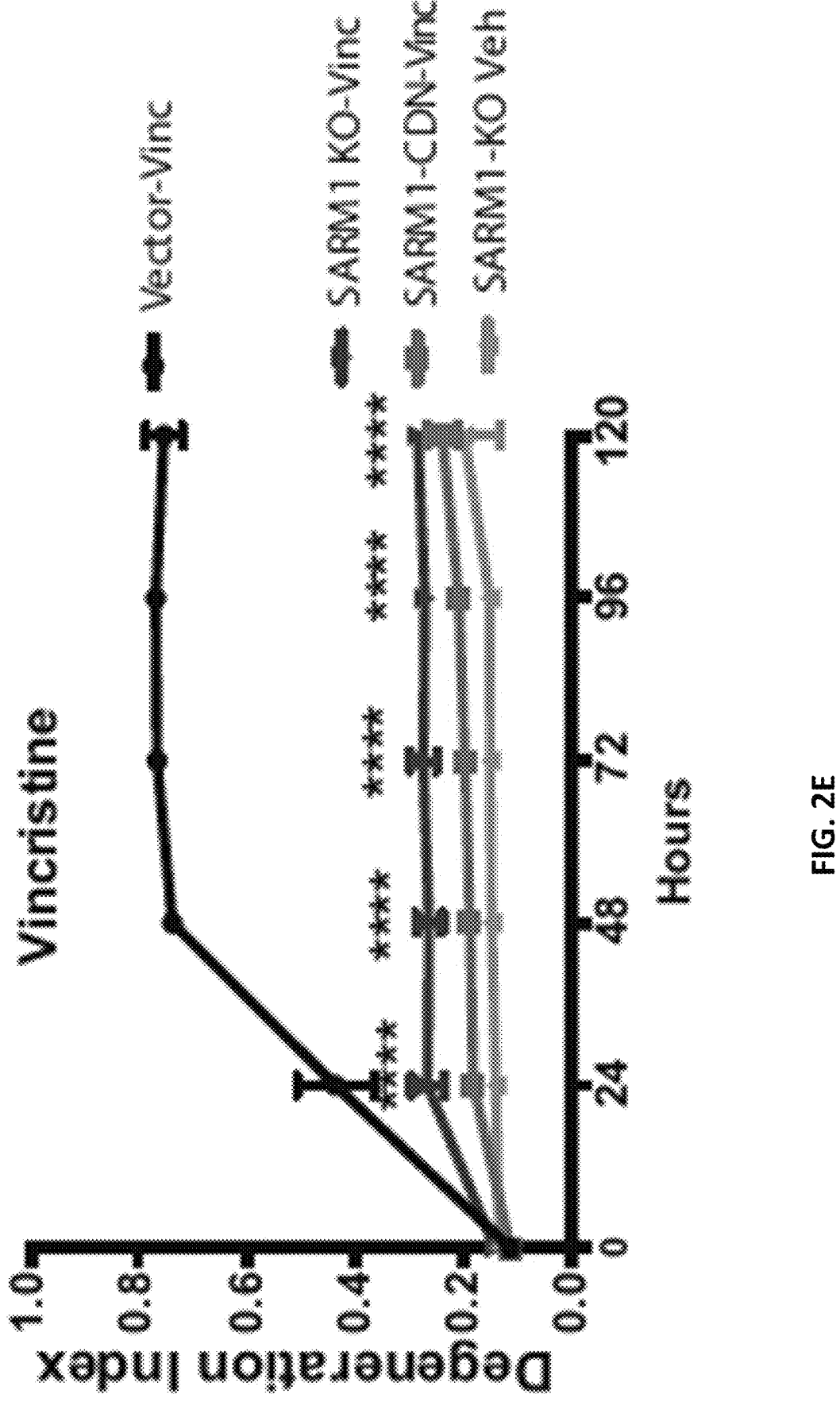
Figure 2F:
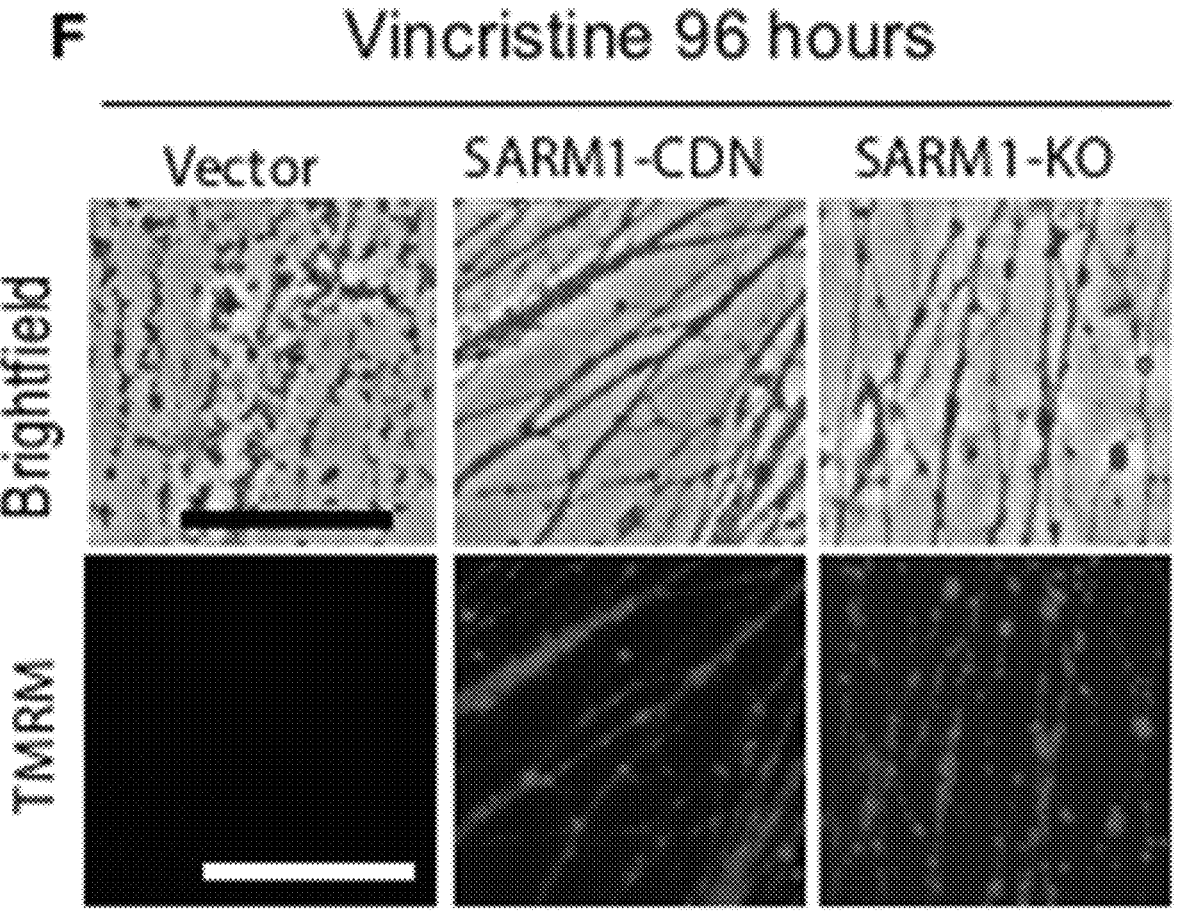

The loss of SARM1 inhibits AxD in models of disease, including traumatic brain injury (Henninger et al., 2016; Ziogas and Koliatsos, 2018) and chemotherapy-induced peripheral neuropathy (Geisler et al., 2016; Turkiew et al., 2017). To examine the effects of SARM1-CDN in chemotherapy-induced peripheral neuropathy, wildtype DRGs with vincristine were treated and observed complete fragmentation of axons 48 hours after application of the drug (FIG. 2E). In contrast, axons of both SARM1-KO neurons as well as wildtype neurons expressing the SARM1 dominant-negative mutant are morphologically intact and retain TMRM-positive mitochondria for at least 96 hours after vincristine application (FIG. 2E, FIG. 2F). Taken together, these data demonstrate that expressing SARM1-CDN in wildtype neurons potently inhibits SARM1 function in response to diverse insults in vitro.

Figure 3A:
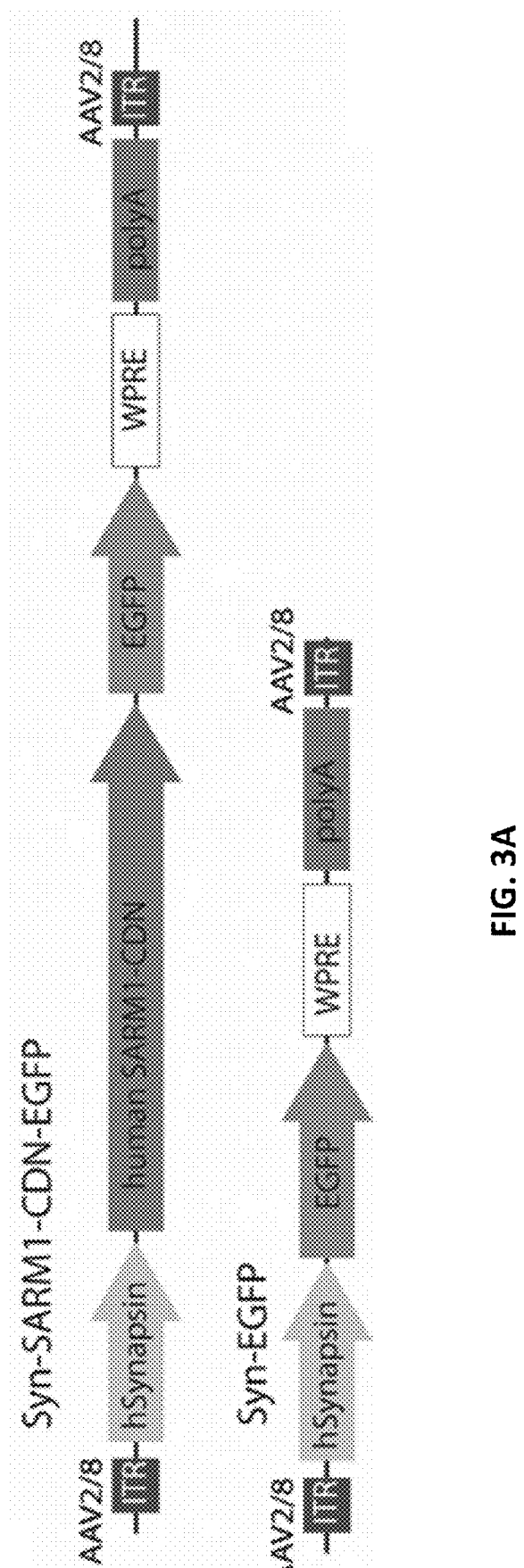
FIG. 3A, FIG. 3B, FIG. 3C, FIG. 3D and FIG. 3E show SARM1-CDN efficiently transduces DRGs in vivo and protects from AxD.
Figure 3B:
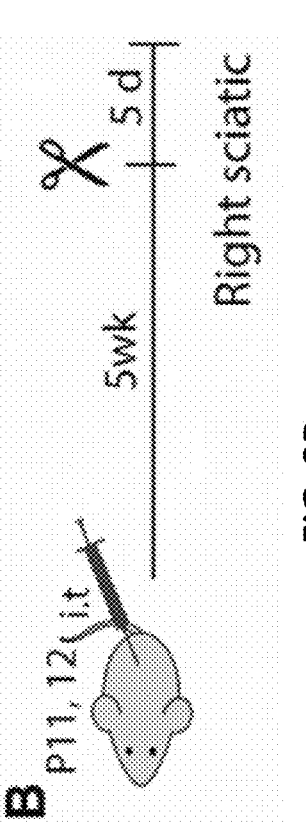
Figure 3C:
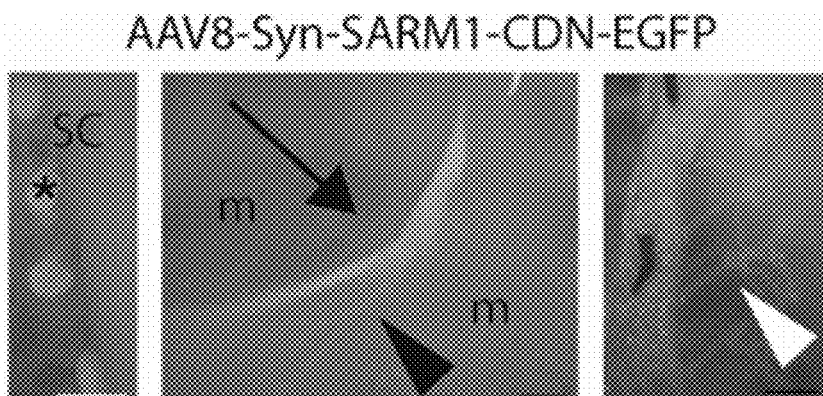
Figure 3D:
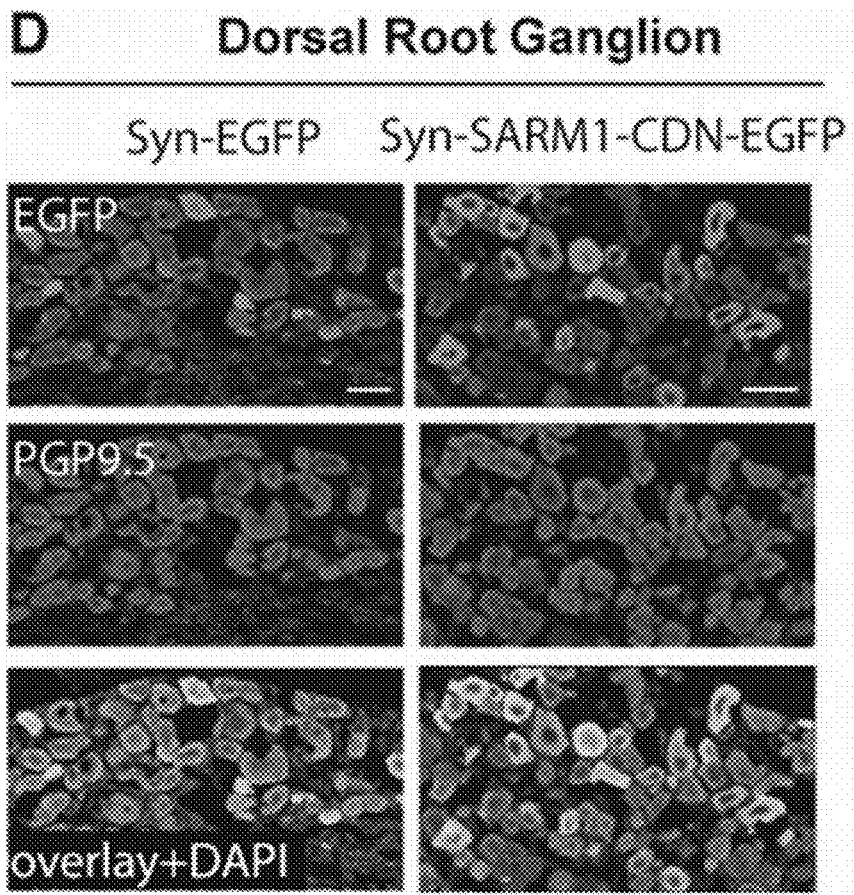

Example 3—SARM1-CDN is Strongly Expressed in Dorsal Root Ganglion Neurons and Peripheral Nerves Upon AAV Mediated Gene Transfer Next, any axo-protective properties of SARM1-CDN in vivo were analyzed. As a proof of concept, sciatic nerve transection as a model of severe pathological AxD was utilized, reasoning that this is the most robust test of efficacy. SARM1-CDN fused to EGFP (FIG. 3A) or EGFP alone were cloned into an AAV8 vector and expressed under the neuron-specific synapsin (Syn) promoter (FIG. 3A). Five weeks after intrathecal administration of AAV8-Syn-SARM1-CDN-EGFP (AAV-SARM1-CDN) or control EGFP virus (FIG. 3B) we observed robust EGFP labeling of DRGs and peripheral nerves, including the sciatic (FIG. 3C, FIG. 3D) and intercostal nerves (FIG. 3C). DRGs are efficiently transduced as determined by staining with the neuronal marker PGP9.5 (FIG. 3D).

Figure 7A:
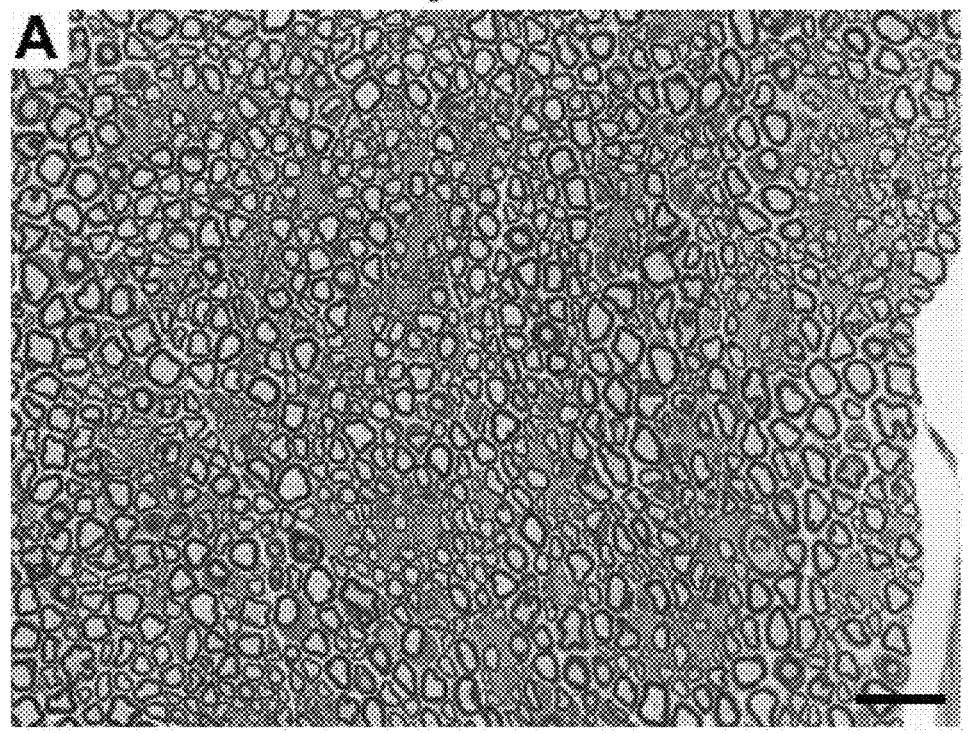
FIG. 7A, FIG. 7B, FIG. 7C, FIG. 7D, FIG. 7E and FIG. 7F show no morphometric differences between uninjured sciatic nerves after injection with AAV-vector and AAV-SARM1 dominant-negative (FIG. 7A-FIG. 7D) Representative photomicrographs of toluidine blue stained semithin cross sections of the uninjured sciatic nerve in mice injected with (FIG. 7A, FIG. 7C) EGFP vector (AAV-Syn-EGFP) or (FIG. 7B, FIG. 7D) AAV-Syn-SARM1-CDN-EGFP (AAV-SARM1-CDN-EGFP).
Figure 7B:
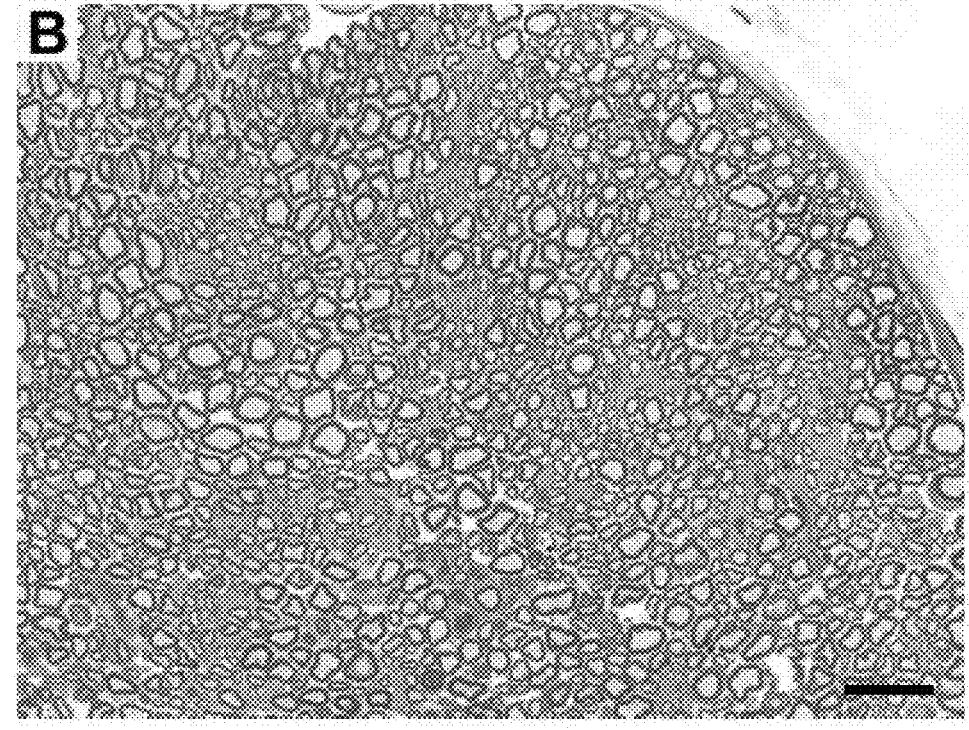
Figure 7C:
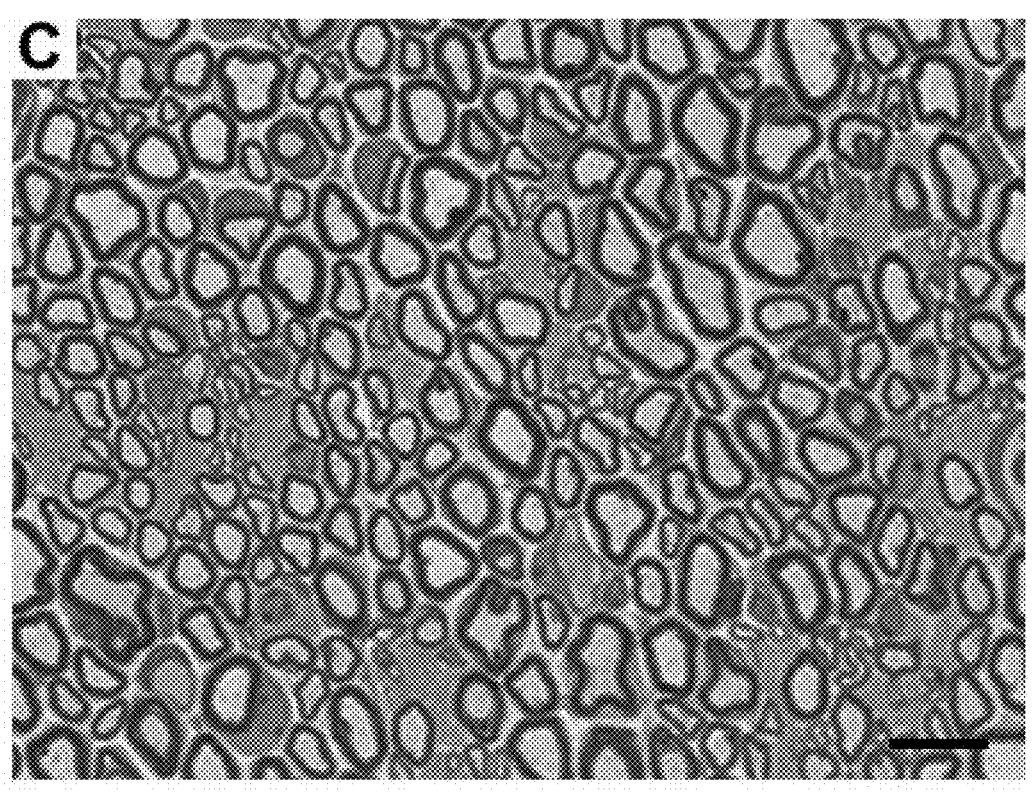
Figure 7D:
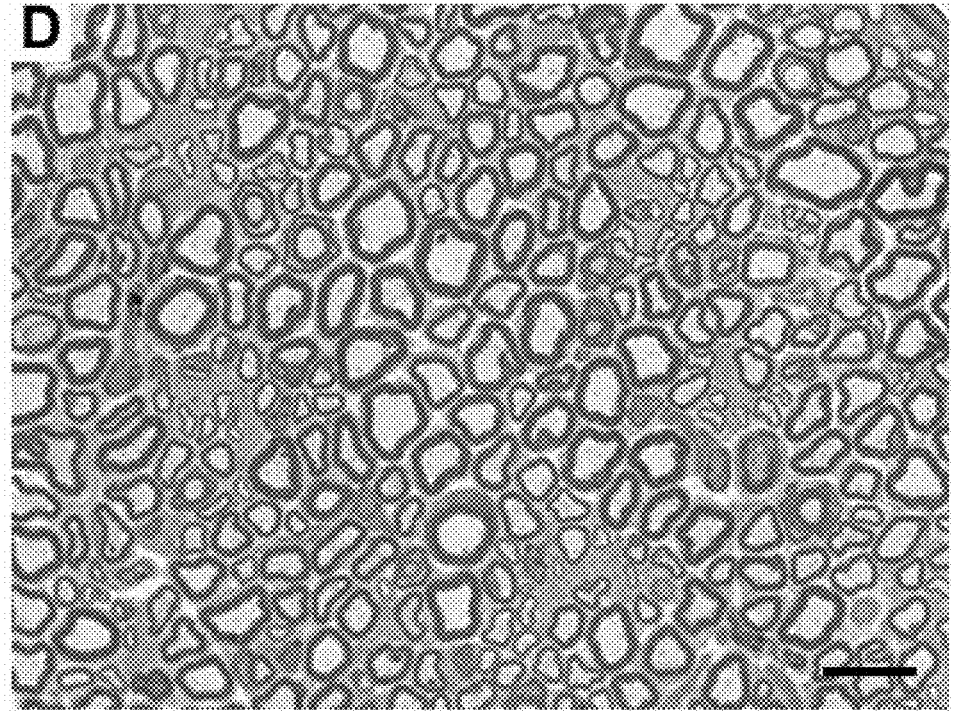
Figure 7E:
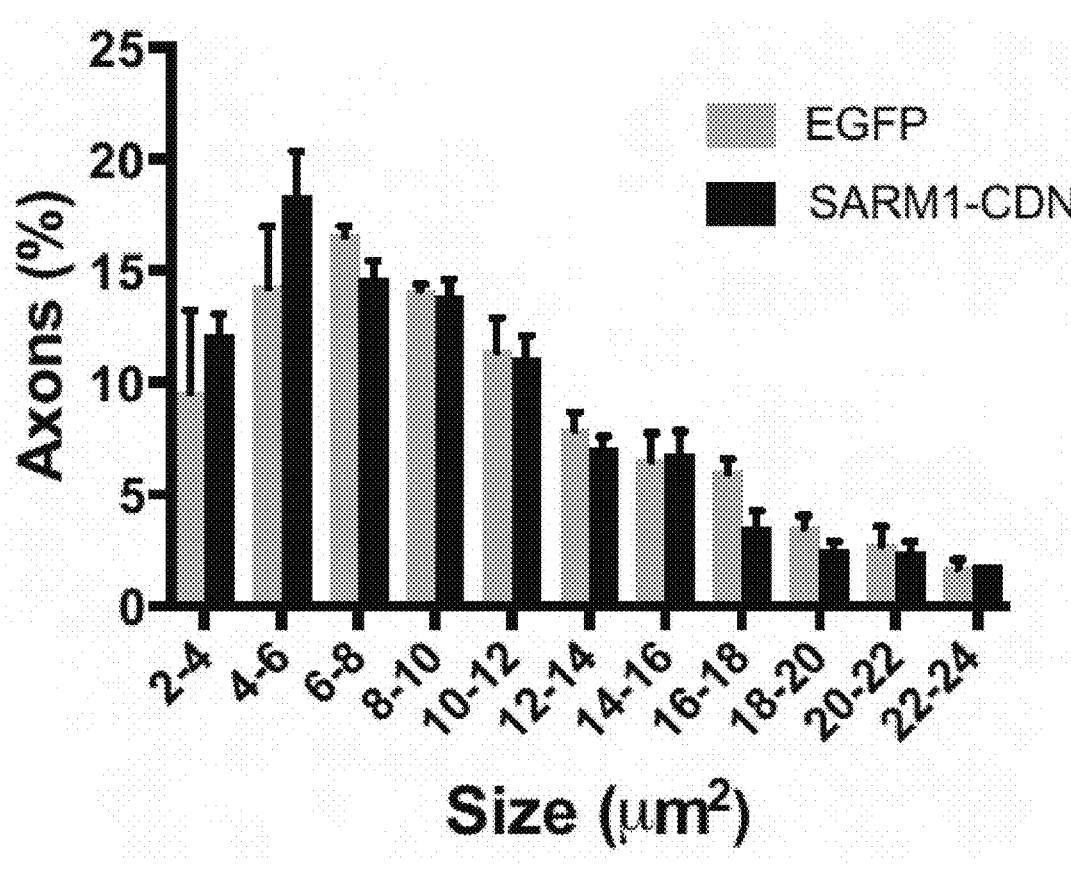
Figure 7F:
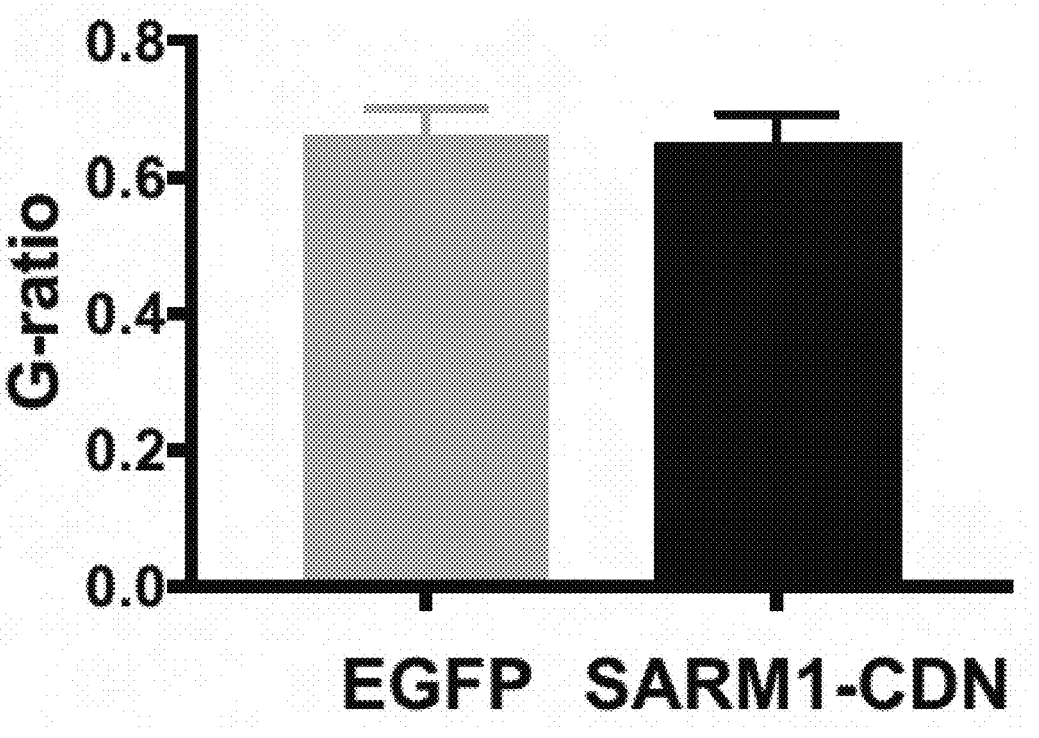

Before evaluating the role of the SARM1-CDN in blocking injury-induced axon degeneration, it was first assessed whether expression of AAV-SARM1-CDN induces morphological changes to axons in the absence of injury. Toluidine blue stained semithin cross sections of the uninjured sciatic nerves of mice injected with dominant-negative or control EGFP virus was analyzed. Axons of sciatic nerves of mice injected with AAV-SARM1CDN and AAV-EGFP appeared morphologically intact (FIG. 7A-D). There was no difference in axon size distribution (FIG. 7E) and G-ratio (FIG. 7F) between the two treatment groups. Hence, expression of SARM1-CDN has no detectable influence on axons in the absence of injury.

Example 4—SARM1-CDN Potently Protects from Axonal Degeneration In Vivo

Figure 3E:
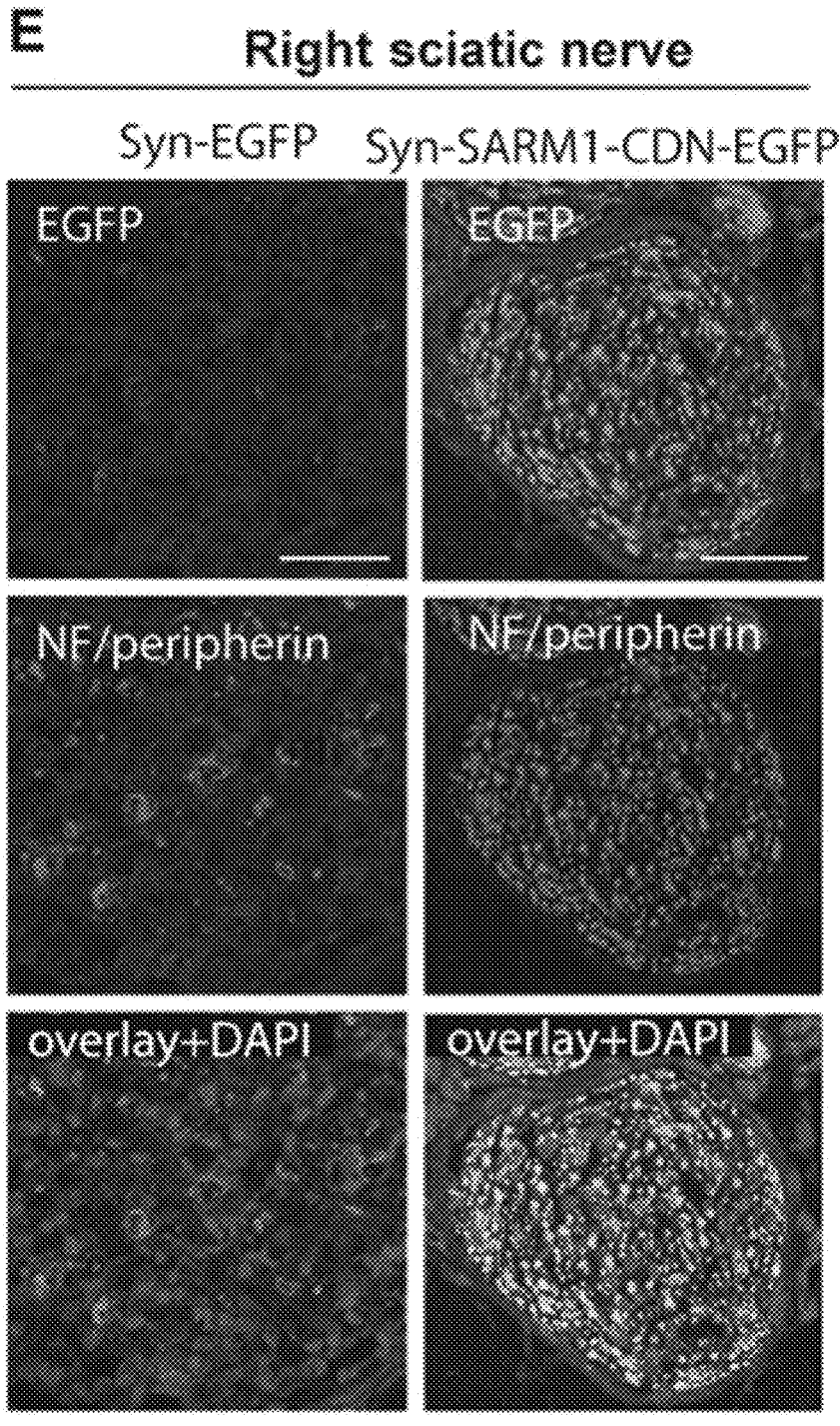

Five days after sciatic transection, axons are largely absent in the distal nerve segment in mice injected with control virus, as evidenced by lack of EGFP fluorescence and loss of neurofilament and peripherin staining (FIG. 3E). In contrast, EGFP fluorescence and neurofilament and peripherin staining are readily observed in nerves of mice injected with AAV-SARM1-CDN (FIG. 3E), indicating that axons expressing the dominant-negative are protected from degeneration.

Figure 4A:
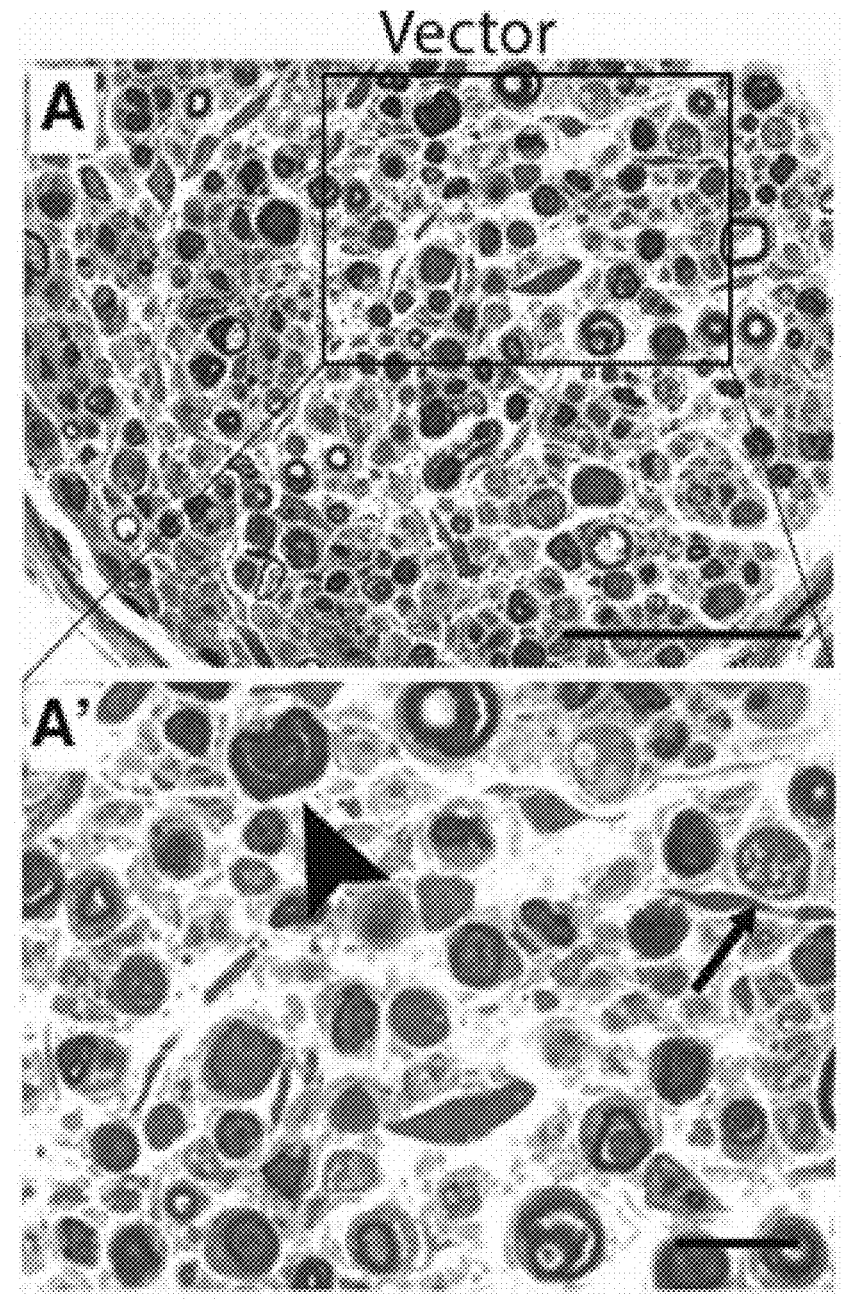
FIG. 4A, FIG. 4B, FIG. 4C, FIG. 4D, FIG. 4E, FIG. 4F and FIG. 4G show SARM1-CDN protects from AxD in vivo with efficacy similar to SARM1-KO.
Figure 4B:
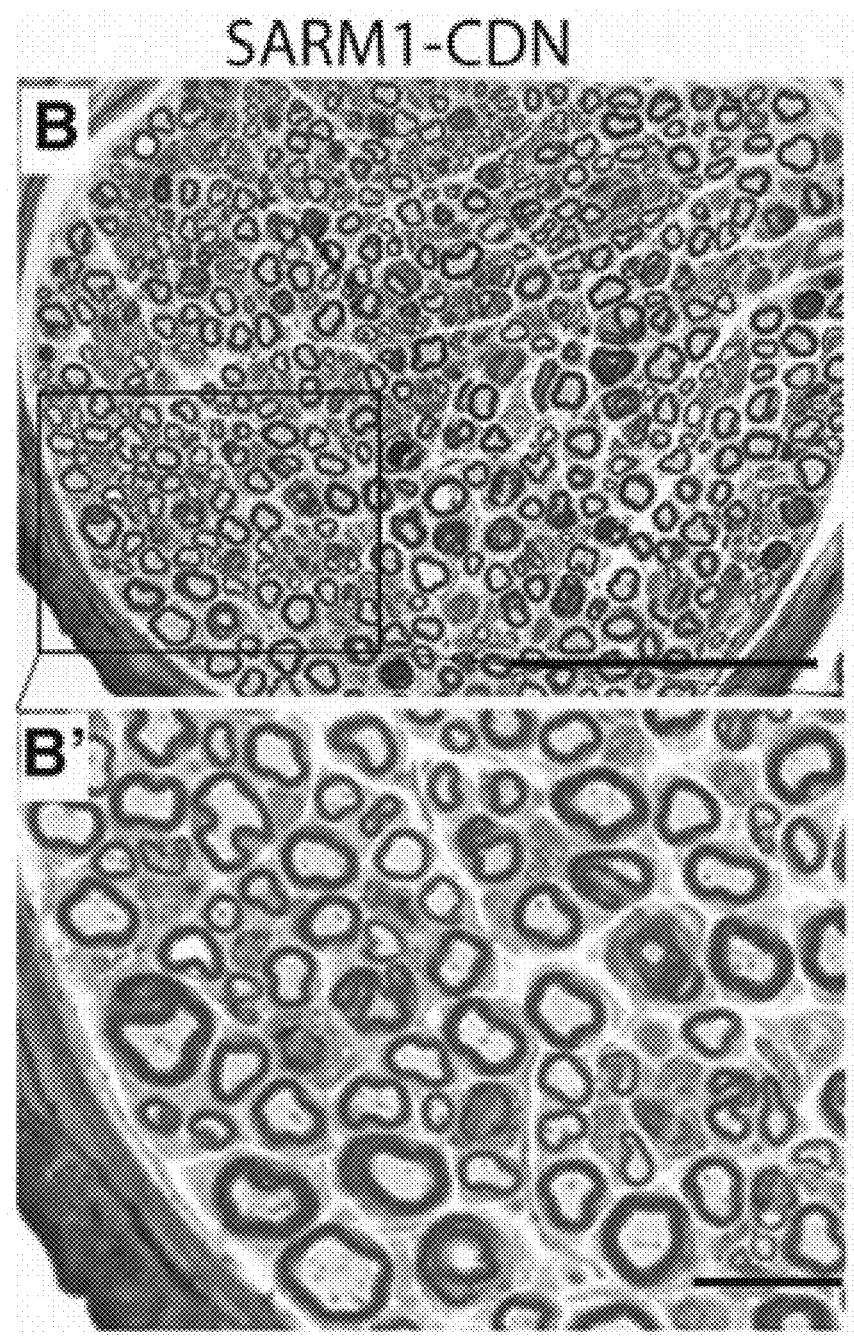
Figure 4C:
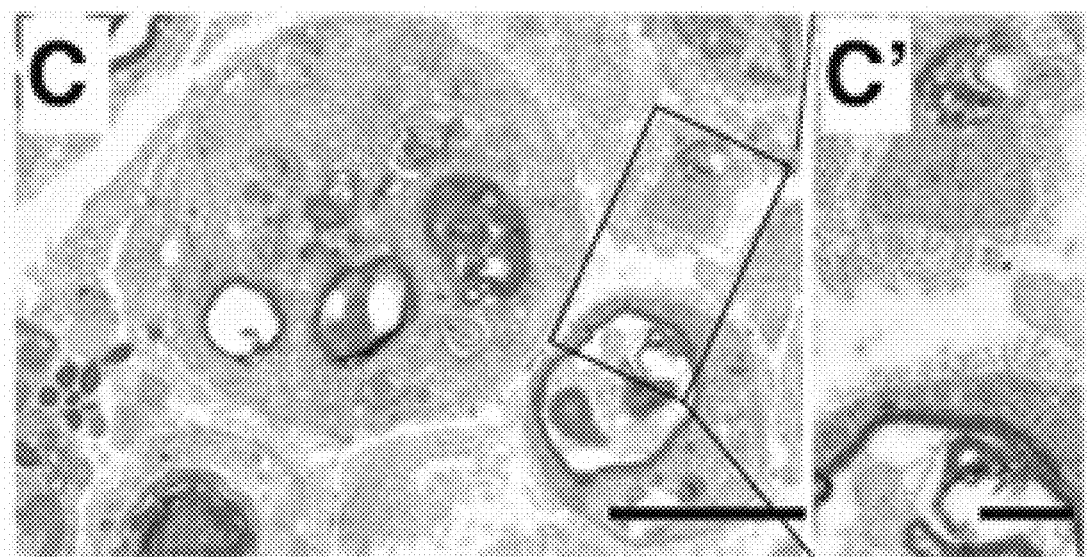
Figure 4D:
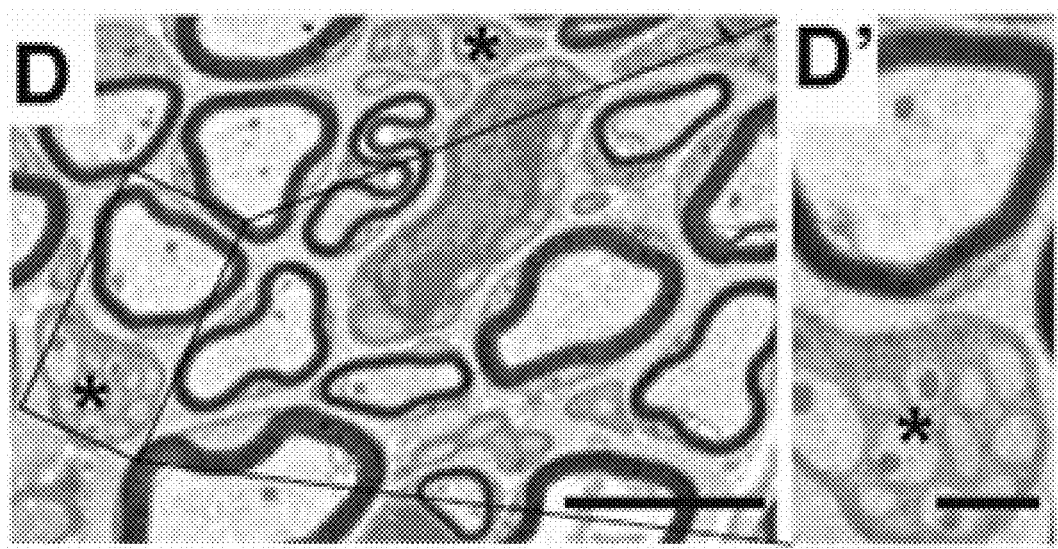
Figures 4E, 4F:
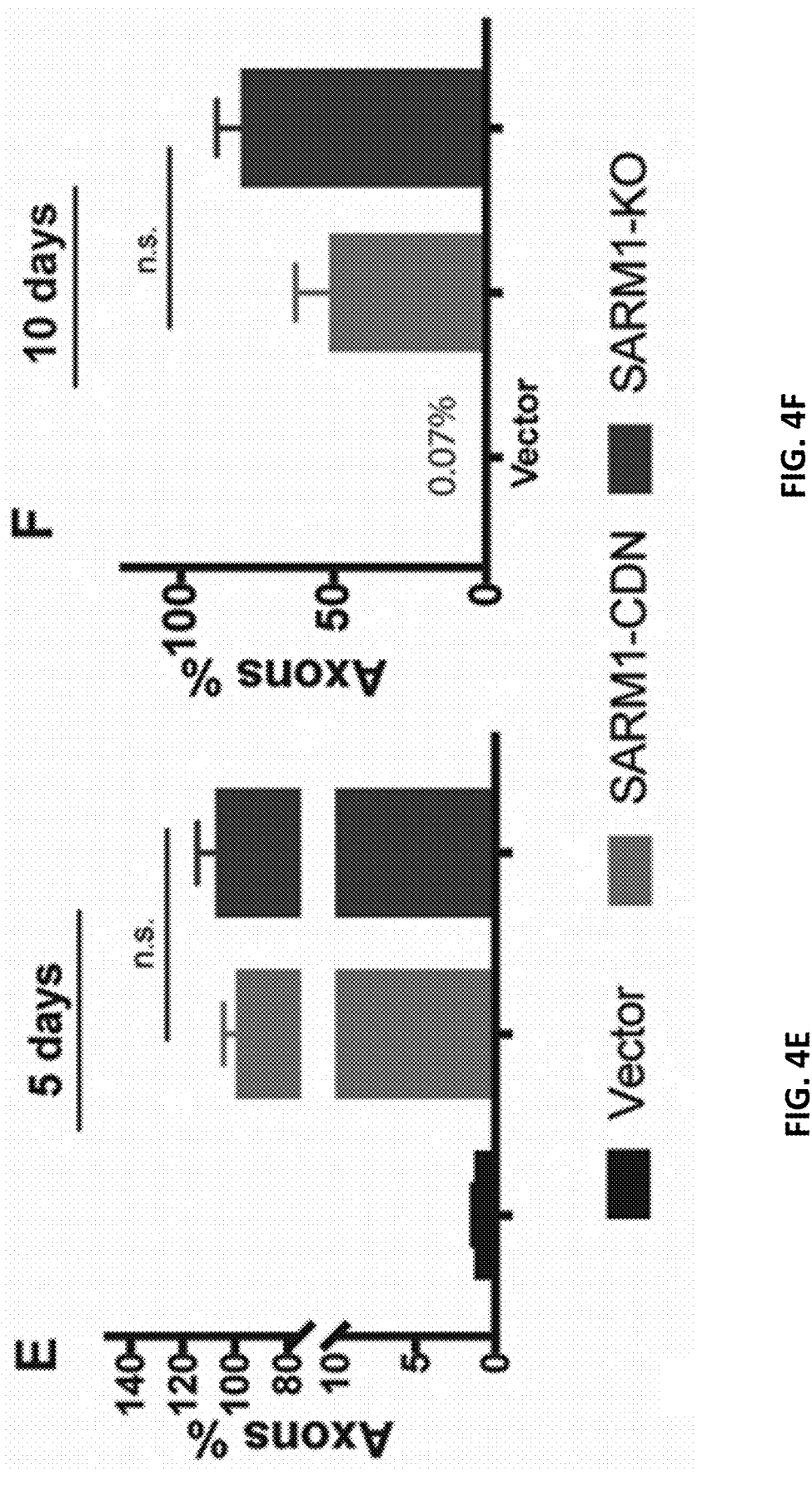
Figure 4G:
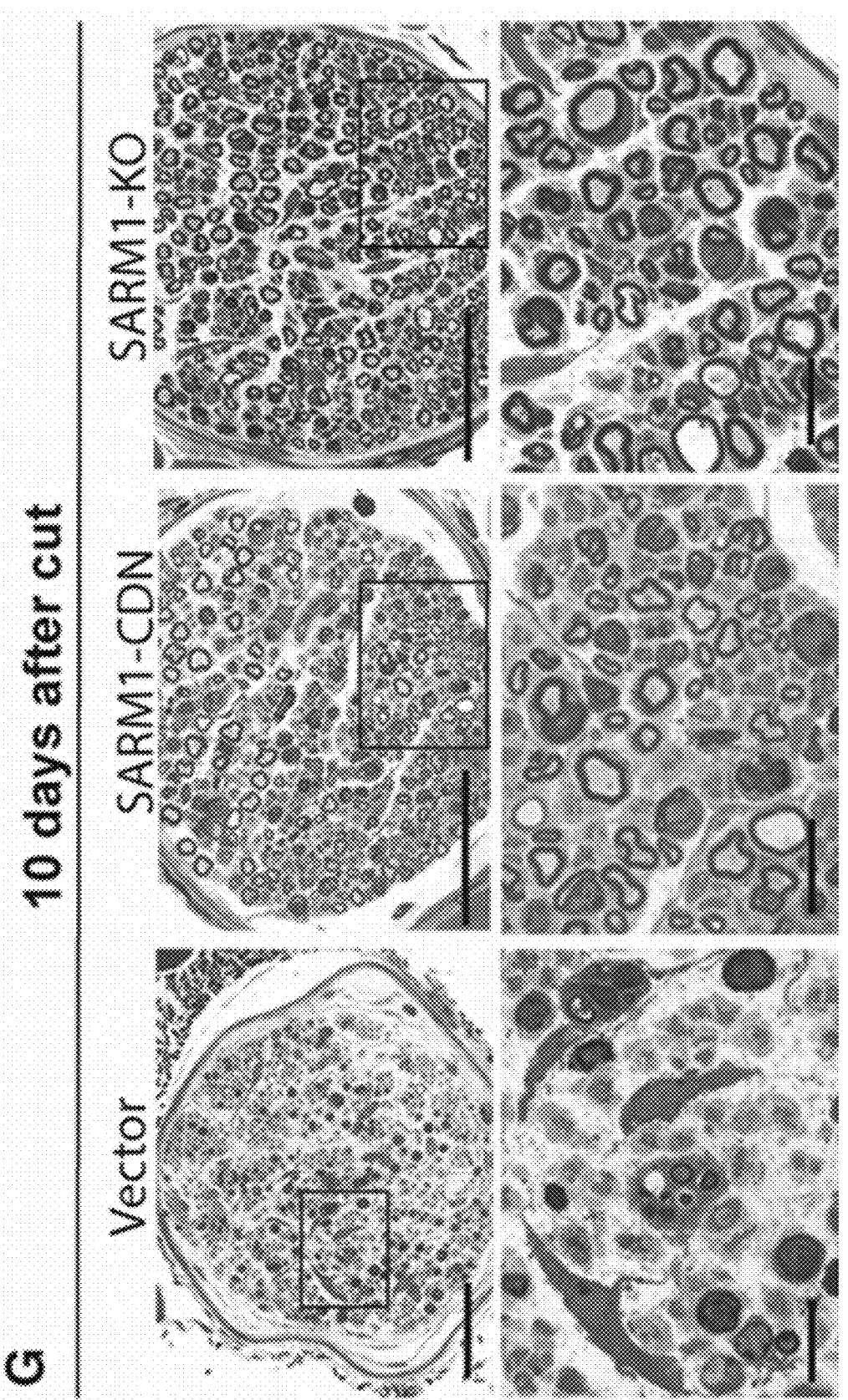

The severity of axonal loss after nerve cut and degree of protection afforded by the dominant negative are even better appreciated using plastic-embedded thin sections. Five days after transection, signs of widespread Wallerian degeneration, including Schwann cells with myelin debris, lipid laden histiocytes and axon remnants with dark cytoplasm (FIG. 4A, A', C, C') are apparent in cross-sections of the sural nerve, a sensory branch of the sciatic nerve distal to the cut. In contrast, in mice injected with AAV-SARM1-CDN, myelinated axons are remarkably well preserved, with normal shape, myelin thickness, and internal architecture (FIG. 4B, B', D, D'). With the aid of electron microscopy, it becomes evident that this protection also extends to unmyelinated axons (FIG. 4D, D'). When the numbers of myelinated axons on the injured and uninjured sides were compared, mice injected with EGFP-vector show a reduction of ~99% (ipsilateral 5±0.9 axons/nerve; contralateral 446±57 axons/nerve; n=4 mice; FIG. 4E), whereas there is no significant axon loss in mice expressing SARM1-CDN (cut site: 389±13 axons/nerve; contralateral 396±28 axons, n=5 mice, FIG. 4E) or in SARM1-KO mice (FIG. 4E). Even ten days after transection, distal axons are present in mice injected with SARM1-CDN (FIG. 4G). While axons in the sural nerves of the vector treated group at that time point were not detected (0.3±0.3 axons; n=3 mice, FIG. 4F, FIG. 4G), 160±40 axons per sural nerve (n=3 mice) in the AAV-SARM1-CDN group were identified, which is about 59±15% of the number of axons present in the uninjured nerve (FIG. 4F). This preservation is comparable to SARM1-KO mice (FIG. 4F, FIG. 4G), in which 79±9% of axons remain distal to injury site (FIG. 4F, FIG. 4G).

The above examples establish AAV-mediated, neuron-specific expression of a SARM1-dominant-negative as a powerful tool to potently inhibit AxD in vivo. These findings demonstrate that SARM1 acts neuron-autonomously and show that it can be effectively targeted in adult wildtype mice. These findings translate the recent dramatic progress in defining the molecular mechanism of axon degeneration into a novel therapeutic strategy to block pathological AxD in neurological disorders.

SARM1 is a multimer, and mutant SARM1 co-assembles with wildtype SARM1 (Gerdts et al., 2013). Hence, the relative dominant negative efficacy of distinct SARM1 mutants may give mechanistic clues to SARM1 function, although differences in expression and/or localization may also contribute. Mutating residues K193 and H685 in SARM1 generate very potent dominant negative transgenes, indicating that K193 in the N terminus and H685 in the TIR domain are likely essential for activation of SARM1. Interestingly, mutating the active site of the TIR domain (E642A) completely abrogates SARM1 function when re-expressed in SARM1 null neurons, but has no dominant-negative effect when expressed in wildtype neurons. This suggests that each enzymatic active site in the complex functions independently. However, our data (Gerdts et al., 2013) as well as a vast literature on other TIR domain proteins (Narayanan and Park, 2015) demonstrate that TIR dimer interactions are necessary for activation of TIR domains. We suggest that while the E642 residue is necessary for intrinsic enzyme activity of a TIR domain, the H685 residue is necessary for activation of enzyme activity in the adjacent, interacting TIR domain, and so when mutated can act as a dominant-negative. In addition, N-terminal residues such as K193 appear to be required for injury-induced activation of SARM1 via relief of autoinhibitory interactions with the TIR domain. Because the effects of H685A and K193R mutations are additive, their mechanisms of inhibition are likely distinct.

Many common neurodegenerative diseases are characterized by early AxD (Burke and O'Malley, 2013; Johnson et al., 2013; Howell et al., 2013; Yin et al., 2016). Peripheral neuropathies are the most common neurodegenerative diseases affecting more than 20 million people in the US alone. Many neuropathies are caused by degeneration of long axons, yet specific therapies to block this degeneration do not exist. Furthermore, in some of the most prevalent diseases of the central nervous system, such as Parkinson's disease, traumatic brain injury and glaucoma, AxD precedes neuronal degeneration (Tagliaferro and Burke, 2016; Cam initi et al., 2017; Fazio et al., 2018; O'Keeffe and Sullivan, 2018). Studies using Wallerian degeneration slow (wlds) mice, which harbor a spontaneous mutation causing significantly delayed AxD (Lunn et al., 1989), and SARM1-KO mice demonstrate that inhibiting the axon destruction program leads to greatly improved functional outcomes (Wang et al., 2001, 2002; Sajadi et al., 2004; Meyer zu Horste et al., 2011; Geisler et al., 2016; Henninger et al., 2016; Fernandes et al., 2018). The active component of WLDs fusion protein is NMNAT1 (Araki et al., 2004), which inhibits SARM1 (Gilley et al., 2015; Sasaki et al., 2016). However, expression of WLDs is less effective than genetic deletion of SARM1 in protecting axons of older mice and in preserving synapses (Conforti et al., 2014; Gilley et al., 2017), suggesting that directly targeting SARM1 will provide better inhibition of pathological AxD. Here we demonstrate that viral delivery of SARM1-K193R/H685A induces long-lasting axon protection following sciatic nerve transection, the most rapid and aggressive trigger of AxD, providing a template for gene therapy treatments of slower axon loss in chronic neurodegenerative diseases.

AAV-mediated gene delivery has been safely used in patients in clinical trials and has shown promising results in neurological diseases, e.g., spinal muscular atrophy (Mendell et al., 2017; Deverman et al., 2018; Sumner and Crawford, 2018). AAV effectively transduces neurons, is not pathogenic, and supports long-lasting expression after a single delivery (Mittermeyer et al., 2012; Hwu et al., 2012). Thus, AAV-mediated expression of SARM1-CDN, if proven safe in humans, may be useful for the treatment of chronic neurodegenerative diseases, such as hereditary and idiopathic neuropathies and Parkinson's disease, as well as acquired neuropathies, such as chemotherapy-induced neuropathy. In treating chemotherapy-induced neuropathy, it is tempting to speculate that a single injection of AAV- SARM1-CDN may be sufficient to provide axon protection for the duration of chemotherapy treatment.

Example 5—Efficacy of Various SARM1 Mutations

Figure 8A:
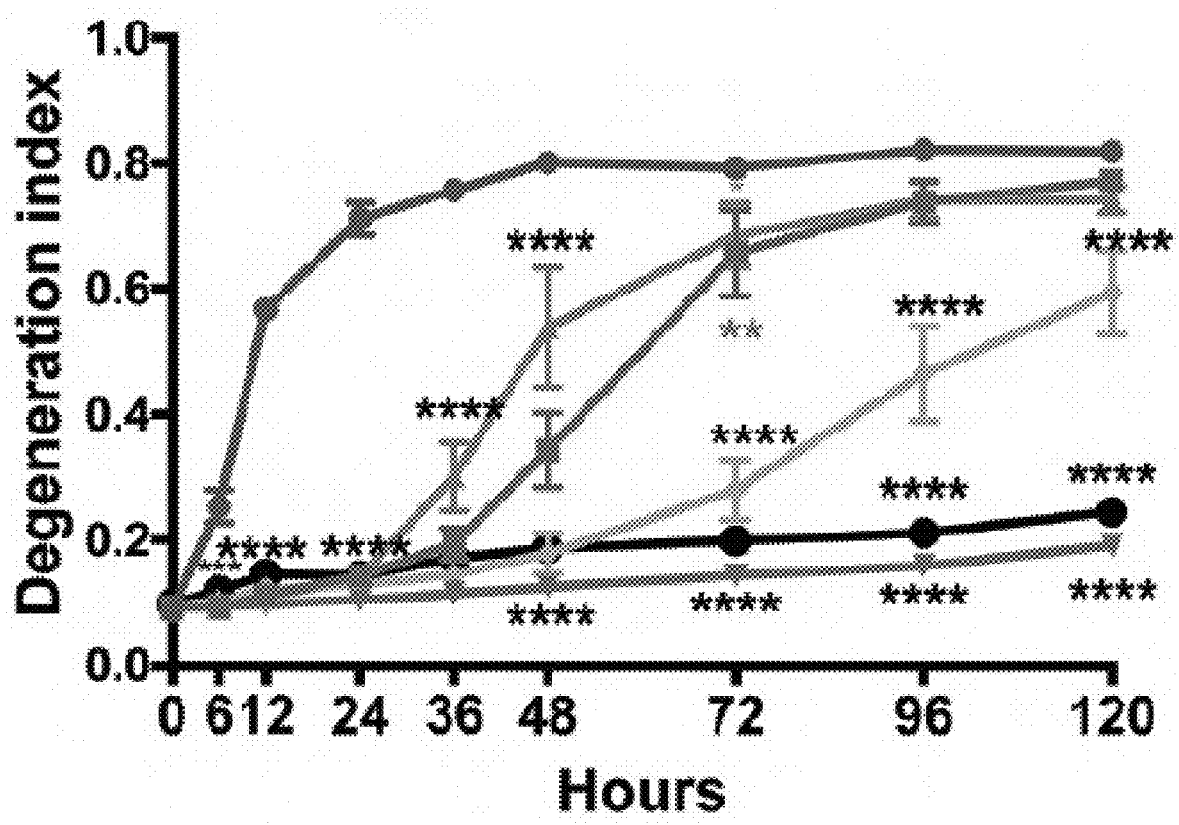
FIG. 8A, FIG. 8B, and FIG. 8C show combining SARM1 point mutations results in powerful dominant negatives that prevent injury induced axon degeneration as potently as SARM1 KO. To investigate if combining the point mutations results in increased protection from injury induced axon degeneration, the inventors generated SARM1 constructs with two or three point mutations. While K193R/E642A and H685A/E642A do not prevent axon degeneration to a greater extent than K193R or H685A alone, expressing a SARM1 construct with point mutations at K193R and H685A prevents axotomy-induced axon degeneration for at least 120 hours and to the same extent as SARM1 KO.
Figure 8B:
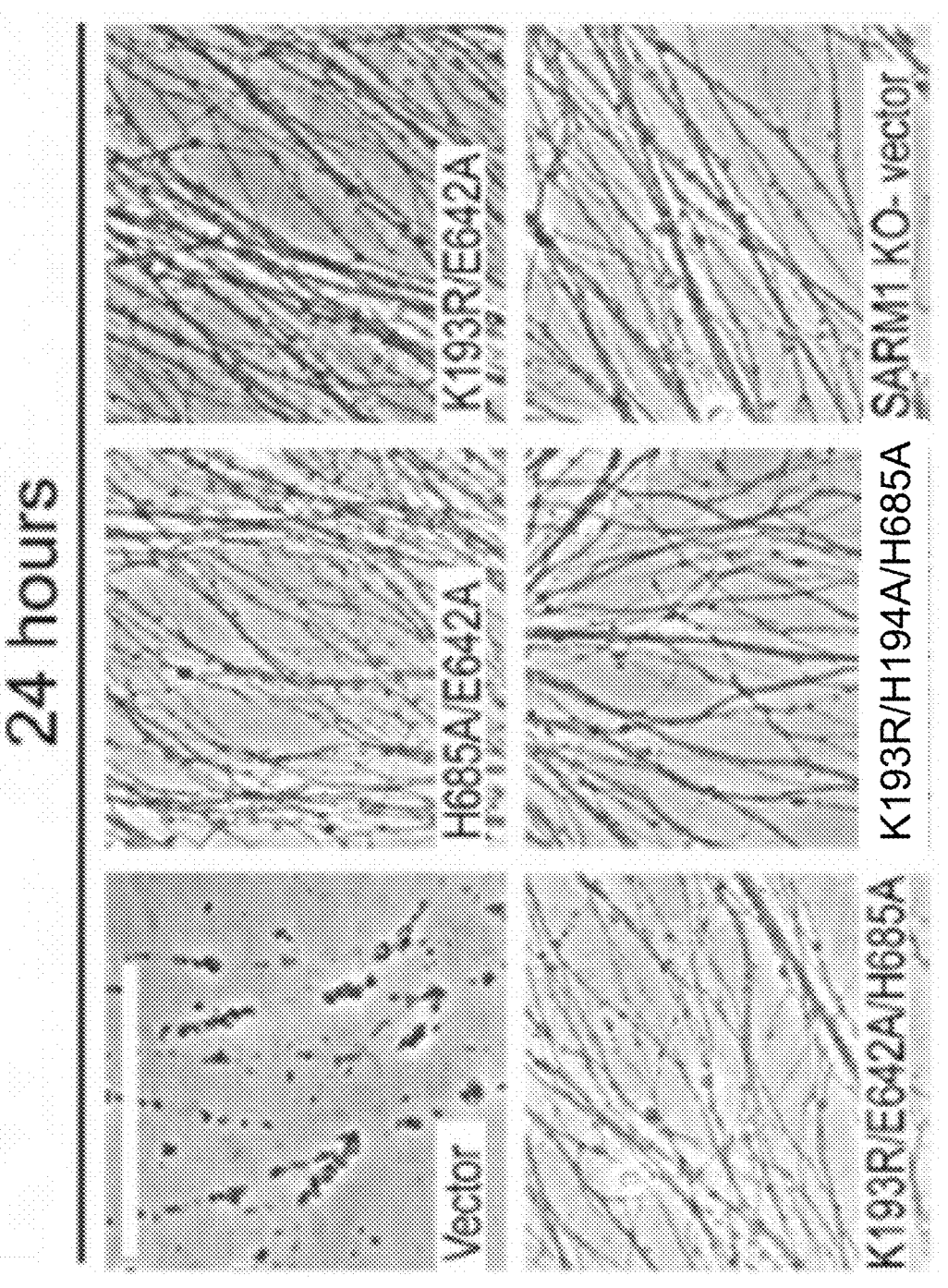
Figure 8C:
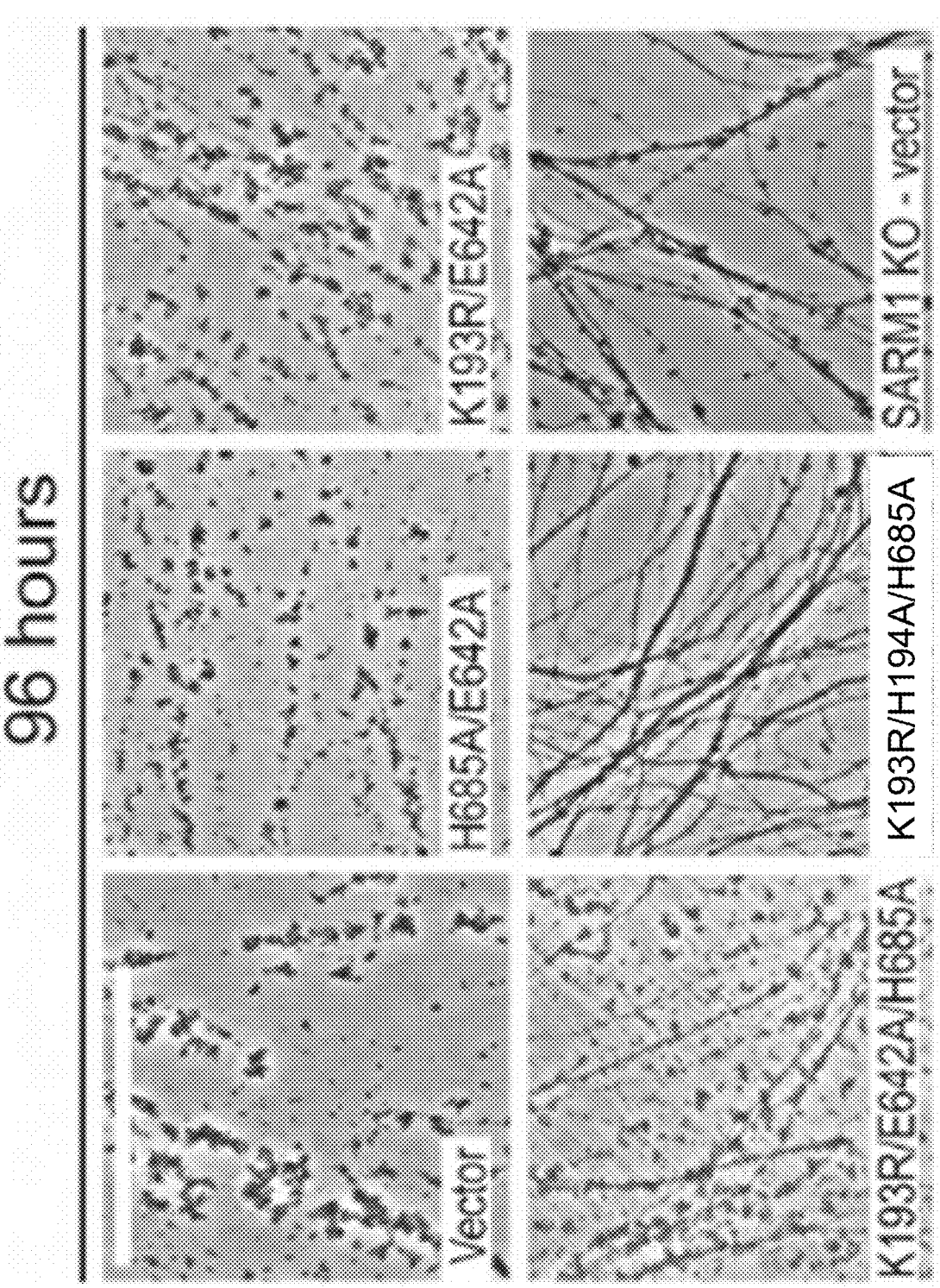
Figure 9A:
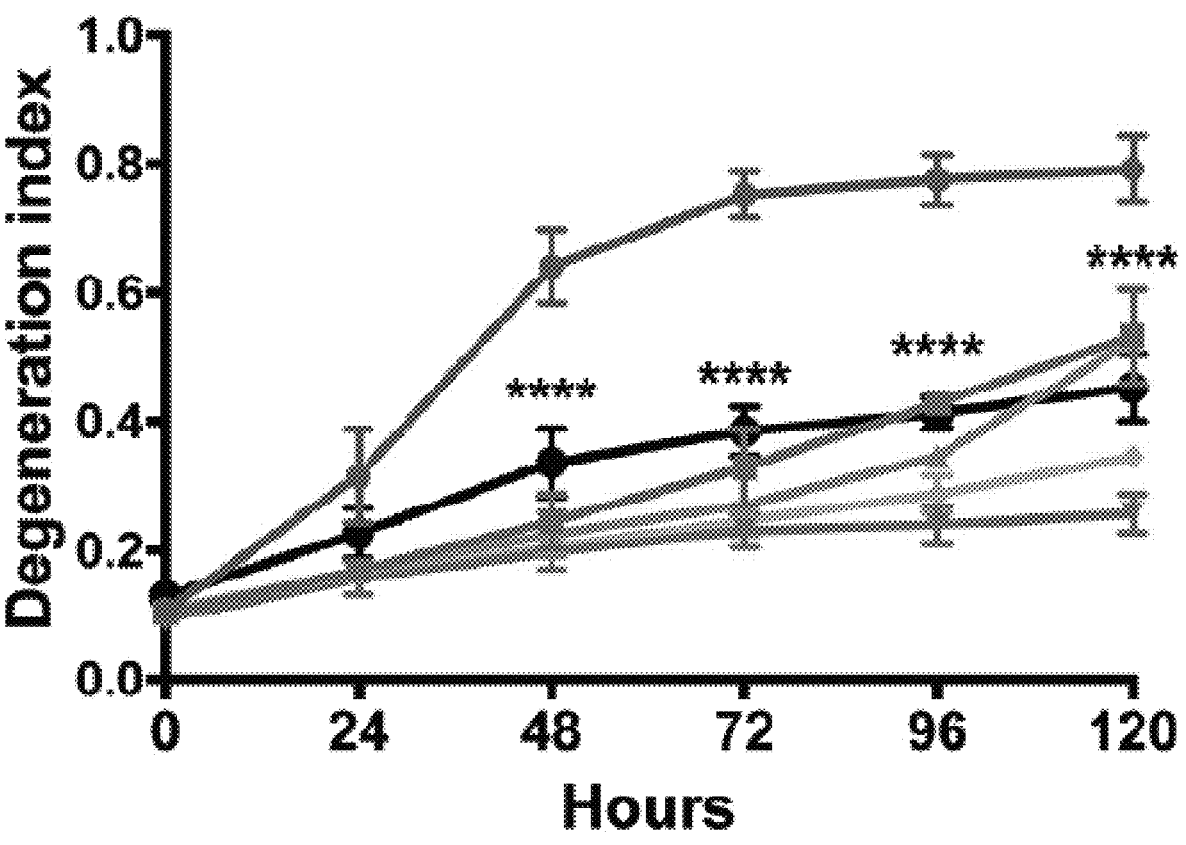
FIG. 9A and FIG. 9B show expression of SARM1 double and triple mutants preserve axon integrity in response to the chemotherapeutic agent vincristine.
Figure 9B:
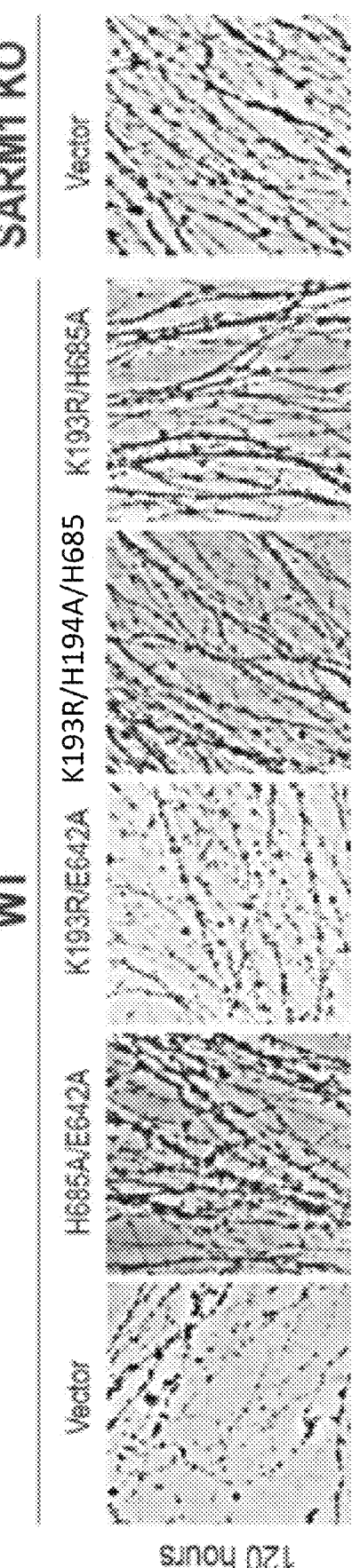
Figure 10:
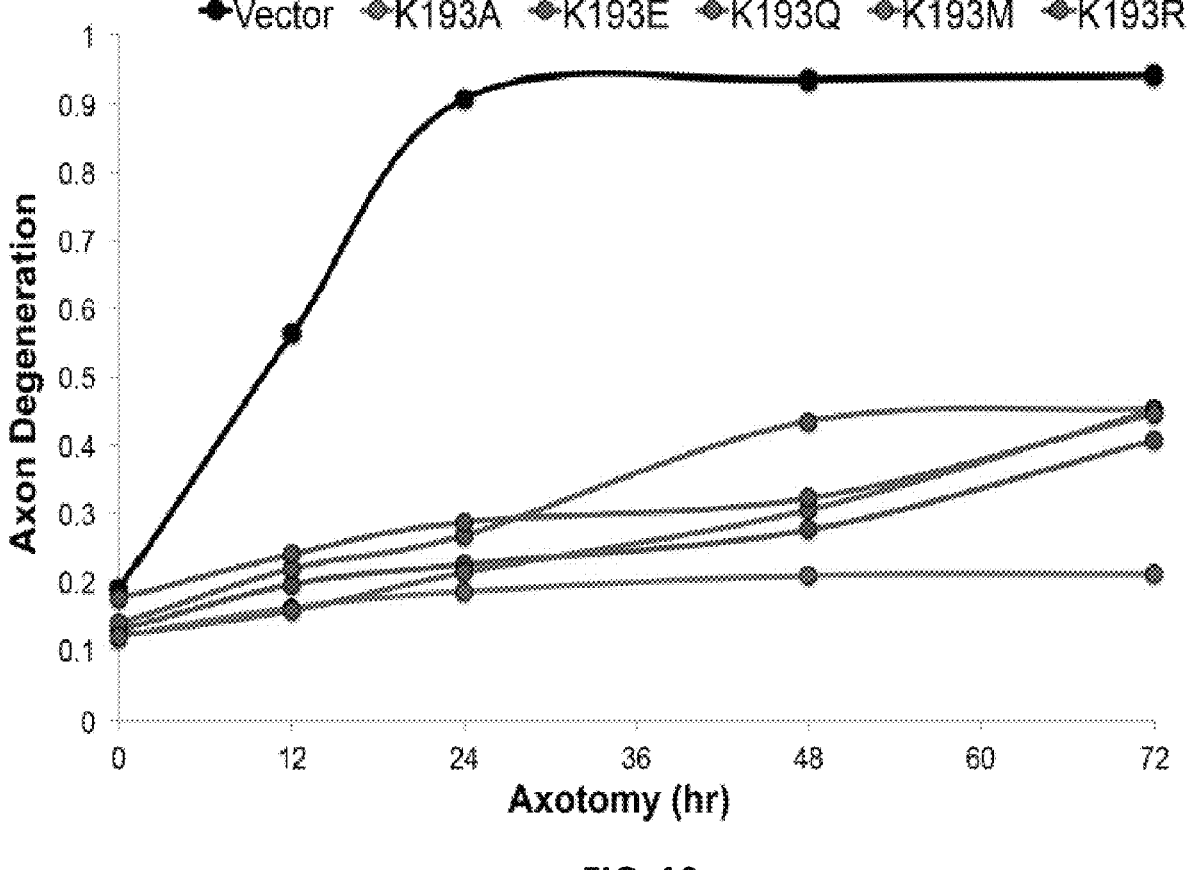
FIG. 10 shows many amino acid substitutions at K193 generate potent dominant negative SARM1 constructs. SARM1 transgenes were generated with the indicated amino acid substitutions (K193A, K193E, K193Q, K193M, as well as the K193R described above). When expressed in wild type axons, all indicated mutants are potent dominant negatives, leading to long lasting axonal protection following axotomy. Hence, mutation of K193 to a wide variety of amino acid types generates a potent dominant negative SARM1 transgene. Note that K193A is particularly potent.

To investigate if combining the point mutations results in increased protection from injury induced axon degeneration, we generated SARM1 constructs with two or three point mutations. While K193R/E642A and H685A/E642A do not prevent axon degeneration to a greater extent than K193R or H685A alone, expressing a SARM1 construct with point mutations at K193R and H685A prevents axotomy-induced axon degeneration for at least 120 hours and to the same extent as SARM1 KO. Combining SARM1 point mutations results in powerful dominant negatives that prevent injury induced axon degeneration as potently as SARM1 KO (FIG. 8A). To investigate, the efficacy of the dominant negative SARM1 molecules in protecting axon integrity in response to chemotherapeutic agents. Wildtype (WT) DRG neurons expressing the indicated constructs (vector, K193R/E642A, H685A/E642A, K193R/H194A/H685A, K193R/E642A, H685A) or SARM1 KO DRGs expressing the empty vector were incubated with 40 nM vincristine and axon degeneration was evaluated at the indicated time points (FIG. 9A). In WT DRGs expressing the empty vector, axons degenerate by 24 hours and completely fragmented at 48 hours after vincristine administration. In contrast, axons of WT DRGs expressing SARM1 double and triple point mutations and axons of SARM1 KO neurons are protected from vincristine induced axon degeneration for at least 120 hours. The expression of SARM1 double and triple mutants preserves axon integrity in response to the chemotherapeutic agent vincristine. Moreover, many amino acid substitutions at K193 generate potent dominant negative SARM1 constructs. SARM1 transgenes were generated with the indicated amino acid substitutions (K193A, K193E, K193Q, K193M, as well as the K193R described above). When expressed in wild type axons, all indicated mutants are potent dominant negatives, leading to long lasting axonal protection following axotomy. Hence, mutation of K193 to a wide variety of amino acid types generates a potent dominant negative SARM1 transgene. Note that K193A is particularly potent (FIG. 10).

Figure 11A:
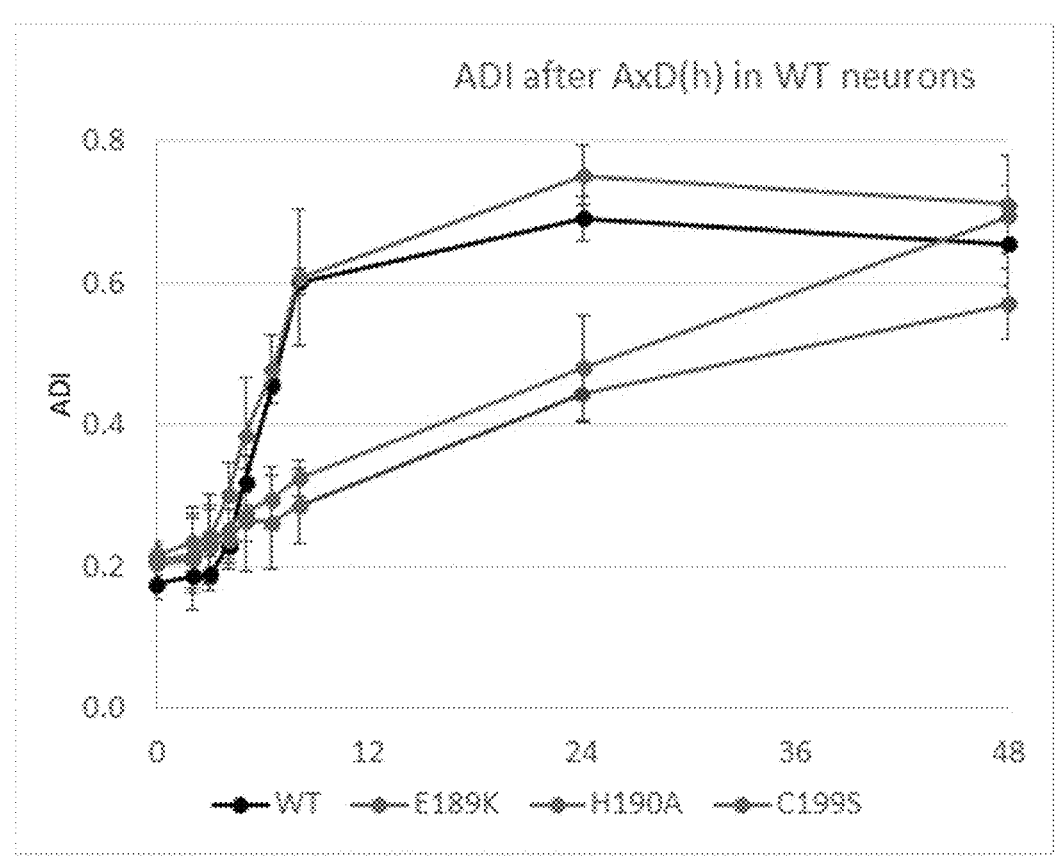
FIG. 11A, FIG. 11B, and FIG. 11C show the efficacy of individual point mutants to act as dominant negatives.
Figure 11B:
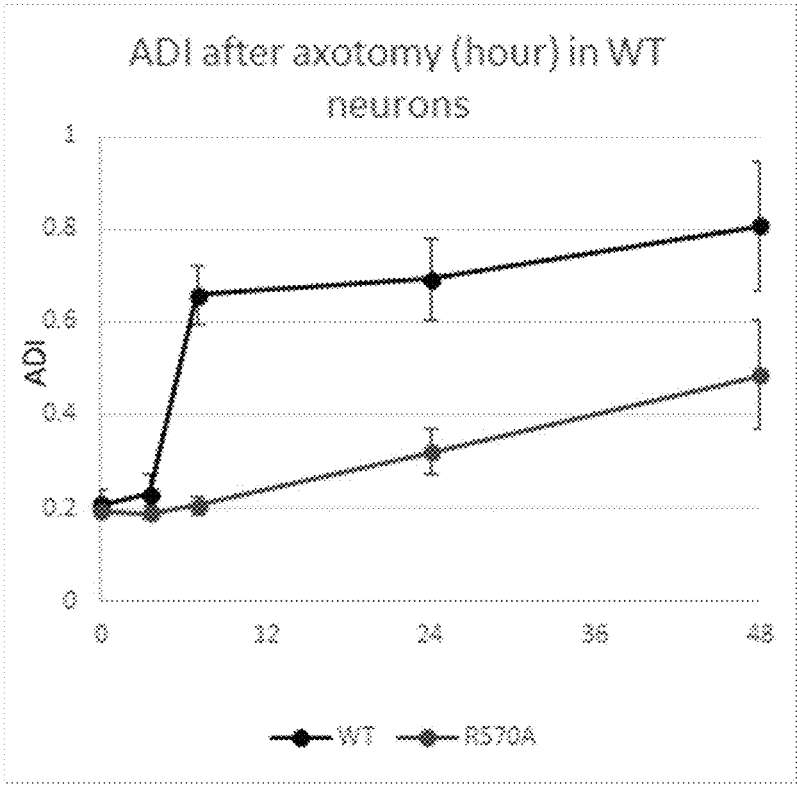
Figure 11C:
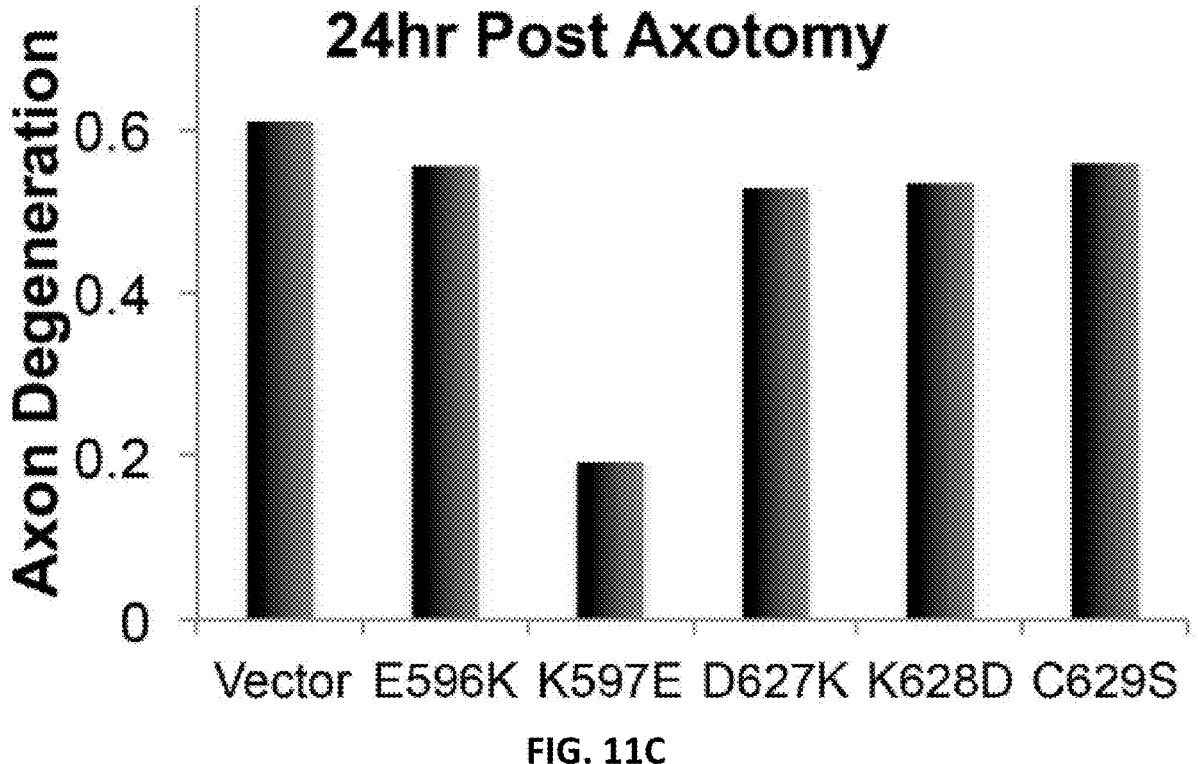

Mutations near 193 were also tested. Wildtype CD1 DRG neurons were infected with virus carrying wildtype Sarm1 (WT), E189K, H190A, or C199S mutation (FIG. 11A). Five days later, axons were severed and the severity of axon degeneration (ADI) was monitored. E189K and H190A showed a significant protection compared with WT infection while C199S mutation didn't offer any protection. Wildtype CD1 DRG neurons were infected with virus carrying wild-type Sarm1 (WT), R570A mutation (FIG. 11B). Five days later, axons were severed and the severity of axon degeneration (ADI) was monitored. R570A showed a significant protection compared with WT. Lastly, neurons expressing SARM1 E569K, D627K, K628D, or C629S constructs were tested for the ability to inhibit axon degeneration. Axons expressing SARM1 E569K, D627K, K628D, or C629S degenerate at a similar speed as wild-type at 24 hours, indicating that they does not act as a dominant negatives (FIG. 11C).

Materials and Methods for Example

All procedures were carried out in accordance with guidelines mandated in the National Institutes of Health Guide for the Care and Use of Laboratory Animals and approved by the Washington University of Saint Louis Medical School Institutional Animal Care and Use Committee (Protocols

20170030 and 20150043). This manuscript was prepared in adherence to the ARRIVE guidelines. Pregnant C57Bl/6NTac mice were purchased from Taconic (Rensselaer, NY) and pregnant CD1 mice were purchased from Charles River (Wilmington, MA). SARM1 knock-out mice were a gift from Marco Colonna (Szretter et al., 2009) and bred in our colony. Male and female mice were used for all experiments. Chemicals were purchased from Sigma Aldrich (Saint Louis, MO) unless indicated otherwise.

Dorsal Root Ganglia Culture

Dorsal root ganglia (DRGs) were dissected from embryonic day 13.5 (E13.5) or E14.5 CD-1 (Charles River) or from E13.5 SARM1 knock-out mouse embryos in Dulbecco's Modified Eagle's medium. DRG neurons were dissociated in 0.05% trypsin-EDTA at 37° C., resuspended in Neurobasal media (Invitrogen) containing 2% B27 (Invitrogen), 50 ng/ml nerve growth factor (Harlan Laboratories), 1 μM 5-fluoro-2-deoxyuridine, and 1 μM uridine and plated in 48 well plates coated with poly-D-lysine and laminin. Concentrated lentivirus was added at 50 fold final dilution the following day (DIV1). All experiments with direct comparisons were performed on the same plate to minimize variability.

Lentiviral Constructs and Infection

Mammalian expression constructs were derived from an FCIV lentiviral vector (Araki et al., 2004) containing a ubiquitin promoter and Venus marker. Venus tagged SARM1 fusion proteins were created by inserting SARM1 cDNA in frame with Venus with an Ala-Thr-Thr linker between the SARM1 C terminus and Venus. SARM1 mutant constructs were generated by the megaprime PCR method. The SARM1 deletion mutant lacking residues 2-27 and 561-724 (deltaTIR) was subcloned into FCIV using the InFusion system. The control vector contained venus or enhanced green fluorescent protein (EGFP) under control of the ubiquitin promoter (EGFP vector). Successful insertions of clones were verified by sequencing. Lentiviral particles were produced by co-transfection of the lentiviral expression vector FCIV with lentiviral packaging plasmid psPAX2 and vesicular stomatitis virus glycoprotein into HEK293T cells as described previously (Araki et al., 2004). Lentiviral particles were collected 48 hours post-transfection and concentrated with Lenti-X concentrator (Clontech) to a final concentration of 1-10×107 infectious particles/ml. Lentiviral expression of constructs was confirmed by positive fluorescence signal in the cell bodies and ranged from 92.2±7.6% (SARM1-delta TIR) to 98.8±0.7% (SARM1-E642A; FIG. 6) infected DRGs.

Axotomy and Vincristine

DRG neurons were cultured in 48-well microtiter plates with cell bodies sequestered to allow imaging of axons by automated microscopy. On DIV8, axons of DRGs were severed manually near the somae with a 3 mm wide flat blade under microscopic guidance. Cell bodies were removed to preclude axon regeneration. Vincristine (40 nM in DMSO) or vehicle (DMSO) was added on DIV 8 and remained in the wells until the end of the experiment.

Imaging and Quantification of Axonal Degeneration

Fifteen to 20 bright-field images per well of live axons were acquired at indicated time points using an Operetta high-content imaging system (PerkinElmer) with a 20× objective. Axon degeneration was quantified based on axon morphology and reported as the "degeneration index" (DI) using an ImageJ-based script (Sasaki et al., 2009) DI ranges from 0 (perfectly intact) to 1 (perfectly fragmented). Values above 0.5 indicate extensive axon degeneration. All images were inspected and fields without axons or inadequate imaging were omitted. Ten to fifteen images per well were measured as technical replicates. All experiments were performed at least three times and 3-5 wells per condition were averaged for each experiment. To assess mitochondrial potential, tetramethylrhodamine methyl ester (TMRM; ThermoFisher Scientific) was added and axons were imaged 30 min later with an inverted Olympus CKX41 microscope and Nikon DS-QiIMC camera. Exposure times were kept constant between constructs. Brightfield images were obtained in phase contrast using the same microscope and camera.

HPLC Quantification of NAD+

CD1 E13.5 DRGs and SARM1 KO E13.5 DRGs were plated as spot cultures in 24-well plates coated with poly-D-lysine and laminin. On DIV1, neurons were transduced with concentrated virus expressing either Ubquitin-EGFP or Ubiquitin-SARM1-CDN-Venus. On DIV 6, axons were severed and cell bodies removed as described. Immediately (=0 hour time point) or 4 hours post-axotomy, axons were washed with cold 0.9% saline and lysed by addition of 0.5M perchloric acid. Extracts were centrifuged and supernatants collected, neutralized with 3M $K_2CO_3$ and diluted in potassium phosphate buffer. NAD+ was assayed by HPLC on a LC-18T HPLC column (Supelco) at a flow rate of 1 ml/min. Elution peaks were matched to NAD+ standards. Four wells per condition were averaged and three independent experiments were performed.

AAV Constructs and Virus Injections

AAV vector expressing EGFP under control of the human synapsin promoter was obtained from Addgene (gift from Bryan Roth; Addgene #50465) and used as EGFP-vector control (Addgene viral prep #50465-AAV8). pAAV-hSyn-EGFP (Addgene #50465) was cut with Bam HI and Ncol and SARM1-K193R/H194A/H685A (SARM1-CDN) was inserted between the synapsin promoter and EGFP sequence using inFusion (Clontech) system. AAV8-hSYN-SARM1-CDN-EGFP was generated by the viral vector core of the Hope Center for Neurological Diseases at Washington University Saint Louis. Viral particles were purified by iodixanol gradient ultracentrifugation and virus titers were measured by dot blot. Under light anaesthesia with Avertin, 6×1011 viral genomes (vg) were injected intrathecally at L6/S1 into male (n=7) and female (n=10) C57131/6 mice (Taconic) at postnatal day 11 or 12. Two female mice injected with EGFP-vector died subsequently, whereas none injected with the SARM1 dominant-negative construct died.

Sciatic Nerve Transection and Tissue Collection

Five weeks after virus injection, one group of mice (n=9) was anaesthetized with isoflurane, the right sciatic nerve transected and nerve ends bent away from each other to prevent re-connection. Five days after nerve transection, mice were anaesthetized with Avertin and, after the sciatic and sural nerves were dissected out, perfused transcardially with 4% paraformaldehyde in phosphate buffered saline. Spinal cord and dorsal root ganglia were dissected out, cryoprotected overnight in 30% sucrose and frozen in O.C.T (Tissue Tec) in liquid 2-methylbutane cooled by dry ice. The sciatic nerves of a second group of mice (n=6) were transected eight weeks after virus injection and tissue was collected ten days later as described above. For comparison, age matched (11 weeks) SARM1 knock-out mice (n=10; 5 male/5 female) received a sciatic nerve transection and sciatic and sural nerves were dissected out five (n=5 mice; 2 female/3 male) or ten (n=5 mice, 3 female/2 male) days after transection.

Toluidine Blue Staining and Axon Quantification

Sural and sciatic nerves were fixed over night by immersion in freshly prepared 3% glutaraldehyde in 0.1 M PBS and processed as described recently (Geisler et al., 2016). Cross sections (400 nm thick) were cut using a Leica EM UC7 ultramicrotome and stained with 1% toluidine blue (Fisher Scientific). Sural nerve sections were imaged with the 63× oil immersion objective of a Leica DMI 4000B microscope equipped with a Leica DFC 7000-T Camera. Micrographs were stitched using the Leica software and all axons per cross-section were counted in ImageJ. To determine axon size distribution and G-ratios of the sciatic nerve, four non-overlapping areas per cross-section were imaged with a 100× oil objective of a Zeiss Axioskop and photographed with a Hitachi camera. Photographs were analyzed with a customized semi-automated binary imaging analysis method (Hunter et al., 2007). Three nerves per treatment group were analyzed and results of four areas per nerve were averaged. All analyses were done by blinded observers.

Electron Microscopy

Selected blocks of sural nerves were used to cut 90 nm thick ultrathin sections, which were stained with uranyl acetate and lead citrate and viewed with a JEOL JEM 1400 TEM.

Immunohistochemistry

Six μm thick sections of dorsal root ganglia and sciatic nerves were cut at the cryostat (Leica CM1860), mounted onto slides and processed as described recently (Geisler et al., 2016). Experiments with direct comparisons between groups were performed in parallel to minimize variability. Primary antibodies included rabbit anti-Protein Gene Product 9.5 (1:1000, EMD Millipore #AB1761-1-I), rabbit anti-peripherin (1:250, EMD Millipore #AB1530), rabbit anti-neurofilament 200 (1:1000, Sigma Aldrich #N4142), and mouse-anti green fluorescent protein conjugated to alexa-fluor 488 (1:250, ThermoFisherScientific #A-21311). Secondary antibody was Alexa Fluor 594-conjugated goat anti-rabbit (Invitrogen) at a dilution of 1:500. Sections were coverslipped with Vectashield with DAPI (Vector laboratories) to allow visualization of nuclei. Sciatic nerves and DRGs were imaged with the confocal mode of the Leica DMI 4000B using 40× and 20× immersion oil objectives, respectively. PGP 9.5 positive and GFP positive DRG neurons were counted in one stitched confocal slice of the entire DRG in Image J. One section each of two different DRGs was counted per animal and values averaged. GFP was expressed in 85±0.4% of PGP9.5 positive DRG neurons after injection of AAV8-Syn-SARM1-CDN-EGFP.

Statistical Analysis

Unless otherwise stated, data are reported as means±standard error of the mean (SEM). Between group comparisons were made with one way or two way ANOVA as appropriate. Two-sided significance tests were used throughout and P<0.05 was considered statistically significant. All statistics were calculated with the aid of Prism software.

REFERENCES

Araki, T., Y. Sasaki, and J. Milbrandt. 2004. Increased nuclear NAD biosynthesis and SIRT1 activation prevent axonal degeneration. Science. 305:1010-1013. doi: 10.1126/science.1098014.

Bellucci, A., A. Antonini, M. Pizzi, and P. Spano. 2017. The End Is the Beginning: Parkinson's Disease in the Light of Brain Imaging. Front Aging Neurosci. 9:330. doi: 10.3389/fnagi.2017.00330.

Burke, R. E., and K. O'Malley. 2013. Axon degeneration in Parkinson's disease. *Exp. Neurol.* 246:72-83. doi: 10.1016/j.expneurol.2012.01.011.

Caminiti, S. P., L. Presotto, D. Baroncini, V. Garibotto, R. M. Moresco, L. Gianolli, M. A. Volonté, A. Antonini, and D. Perani. 2017. Axonal damage and loss of connectivity in nigrostriatal and mesolimbic dopamine pathways in early Parkinson's disease. *Neuroimage Clin.* 14:734-740. doi:10.1016/j.nicl.2017.03.011.

Cashman, C. R., and A. Höke. 2015. Mechanisms of distal axonal degeneration in peripheral neuropathies. *Neurosci. Lett.* 596:33-50. doi:10.1016/j.neulet.2015.01.048.

Conforti, L., J. Gilley, and M. P. Coleman. 2014. Wallerian degeneration: an emerging axon death pathway linking injury and disease. *Nature Reviews Neuroscience.* 15:394-409. doi:10.1038/nrn3680.

Deverman, B. E., B. M. Ravina, K. S. Bankiewicz, S. M. Paul, and D. W. Y. Sah. 2018. Gene therapy for neurological disorders: progress and prospects. *Nat Rev Drug Discov.* doi:10.1038/nrd.2018.110.

Essuman, K., D. W. Summers, Y. Sasaki, X. Mao, A. DiAntonio, and J. Milbrandt. 2017. The SARM1 Toll/Interleukin-1 Receptor Domain Possesses Intrinsic NAD+ Cleavage Activity that Promotes Pathological Axonal Degeneration. *Neuron.* 93:1334-1343.e5. doi:10.1016/j.neuron.2017.02.022.

Fazio, P., P. Svenningsson, Z. Cselonyi, C. Halldin, L. Farde, and A. Varrone. 2018. Nigrostriatal dopamine transporter availability in early Parkinson's disease. *Movement Disorders.* 33:592-599. doi:10.1002/mds.27316.

Fernandes, K. A., K. L. Mitchell, A. Patel, O. J. Marola, P. Shrager, D. J. Zack, R. T. Libby, and D. S. Welsbie. 2018. Role of SARM1 and DR6 in retinal ganglion cell axonal and somal degeneration following axonal injury. *Exp. Eye Res.* 171:54-61. doi:10.1016/j.exer.2018.03.007.

Geisler, S., R. A. Doan, A. Strickland, X. Huang, J. Milbrandt, and A. DiAntonio. 2016. Prevention of vincristine-induced peripheral neuropathy by genetic deletion of SARM1 in mice. *Brain.* 139:3092-3108. doi:10.1093/brain/aww251.

Gerdts, J., E. J. Brace, Y. Sasaki, A. DiAntonio, and J. Milbrandt. 2015. SARM1 activation triggers axon degeneration locally via NAD+ destruction. *Science.* 348:453-457. doi:10.1126/science.1258366.

Gerdts, J., D. W. Summers, J. Milbrandt, and A. DiAntonio. 2016. Axon Self-Destruction: New Links among SARM1, MAPKs, and NAD+ Metabolism. *Neuron.* 89:449-460. doi:10.1016/j.neuron.2015.12.023.

Gerdts, J., D. W. Summers, Y. Sasaki, A. DiAntonio, and J. Milbrandt. 2013. Sarm1-mediated axon degeneration requires both SAM and TIR interactions. *J. Neurosci.* 33:13569-13580. doi:10.1523/JNEUROSCI.1197-13.2013.

Gilley, J., G. Orsomando, I. Nascimento-Ferreira, and M. P. Coleman. 2015. Absence of SARM1 rescues development and survival of NMNAT2-deficient axons. *Cell Rep.* 10:1974-1981. doi:10.1016/j.celrep.2015.02.060.

Gilley, J., R. R. Ribchester, and M. P. Coleman. 2017. Sarm1 Deletion, but Not WldS, Confers Lifelong Rescue in a Mouse Model of Severe Axonopathy. *Cell Rep.* 21:10-16. doi:10.1016/j.celrep.2017.09.027.

Henninger, N., J. Bouley, E. M. Sikoglu, J. An, C. M. Moore, J. A. King, R. Bowser, M. R. Freeman, and R. H. Brown. 2016. Attenuated traumatic axonal injury and improved functional outcome after traumatic brain injury in mice lacking Sarm1. *Brain.* 139:1094-1105. doi:10.1093/brain/aww001.

Howell, G. R., R. T. Libby, T. C. Jakobs, R. S. Smith, F. C. Phalan, J. W. Barter, J. M. Barbay, J. K. Marchant, N. Mahesh, V. Porciatti, A. V. Whitmore, R. H. Masland, and S. W. M. John. 2007. Axons of retinal ganglion cells are insulted in the optic nerve early in DBA/2J glaucoma. *J. Cell Biol.* 179:1523-1537. doi:10.1083/jcb.200706181.

Howell, G. R., I. Soto, R. T. Libby, and S. W. M. John. 2013. Intrinsic axonal degeneration pathways are critical for glaucomatous damage. *Exp. Neurol.* 246:54-61. doi: 10.1016/j.expneurol.2012.01.014.

Hunter, D. A., A. Moradzadeh, E. L. Whitlock, M. J. Brenner, T. M. Myckatyn, C. H. Wei, T. H. H. Tung, and S. E. Mackinnon. 2007. Binary imaging analysis for comprehensive quantitative histomorphometry of peripheral nerve. *Journal of Neuroscience* Methods. 166:116-124. doi:10.1016/j.jneumeth.2007.06.018.

Hwu, W.-L., S. Muramatsu, S.-H. Tseng, K.-Y. Tzen, N.-C. Lee, Y.-H. Chien, R. O. Snyder, B. J. Byrne, C.-H. Tai, and R.-M. Wu. 2012. Gene therapy for aromatic L-amino acid decarboxylase deficiency. *Sci Transl Med.* 4:134ra61. doi:10.1126/scitranslmed.3003640.

Johnson, V. E., W. Stewart, and D. H. Smith. 2013. Axonal pathology in traumatic brain injury. *Exp. Neurol.* 246:35-43. doi:10.1016/j.expneurol.2012.01.013.

Lunn, E. R., V. H. Perry, M. C. Brown, H. Rosen, and S. Gordon. 1989. Absence of Wallerian Degeneration does not Hinder Regeneration in Peripheral Nerve. *Eur. J. Neurosci.* 1:27-33.

Mendell, J. R., S. Al-Zaidy, R. Shell, W. D. Arnold, L. R. Rodino-Klapac, T. W. Prior, L. Lowes, L. Alfano, K. Berry, K. Church, J. T. Kissel, S. Nagendran, J. L'Italien, D. M. Sproule, C. Wells, J. A. Cardenas, M. D. Heitzer, A. Kaspar, S. Corcoran, L. Braun, S. Likhite, C. Miranda, K. Meyer, K. D. Foust, A. H. M. Burghes, and B. K. Kaspar. 2017. Single-Dose Gene-Replacement Therapy for Spinal Muscular Atrophy. *N. Engl. J. Med.* 377:1713-1722. doi: 10.1056/NEJMoa1706198.

Meyer zu Horste, G., T. A. Miesbach, J. I. Muller, R. Fledrich, R. M. Stassart, B. C. Kieseier, M. P. Coleman, and M. W. Sereda. 2011. The Wlds transgene reduces axon loss in a Charcot-Marie-Tooth disease 1A rat model and nicotinamide delays post-traumatic axonal degeneration. *Neurobiol. Dis.* 42:1-8. doi:10.1016/j.nbd.2010.12.006.

Mittermeyer, G., C. W. Christine, K. H. Rosenbluth, S. L. Baker, P. Starr, P. Larson, P. L. Kaplan, J. Forsayeth, M. J. Aminoff, and K. S. Bankiewicz. 2012. Long-Term Evaluation of a Phase 1 Study of AADC Gene Therapy for Parkinson's Disease. *Hum Gene Ther.* 23:377-381. doi: 10.1089/hum.2011.220.

Narayanan, K. B., and H. H. Park. 2015. Toll/interleukin-1 receptor (TIR) domain-mediated cellular signaling pathways. *Apoptosis.* 20:196-209. doi:10.1007/s10495-014-1073-1.

O'Keeffe, G. W., and A. M. Sullivan. 2018. Evidence for dopaminergic axonal degeneration as an early pathological process in Parkinson's disease. *Parkinsonism Relat. Disord.* doi:10.1016/j.parkreldis.2018.06.025.

Osterloh, J. M., J. Yang, T. M. Rooney, A. N. Fox, R. Adalbert, E. H. Powell, A. E. Sheehan, M. A. Avery, R. Hackett, M. A. Logan, J. M. MacDonald, J. S. Ziegenfuss, S. Milde, Y.-J. Hou, C. Nathan, A. Ding, R. H. Brown, L. Conforti, M. Coleman, M. Tessier-Lavigne, S. ZUchner, and M. R. Freeman. 2012. dSarm/Sarm1 is required for activation of an injury-induced axon death pathway. *Science.* 337:481-484. doi:10.1126/science.1223899.

Sajadi, A., B. L. Schneider, and P. Aebischer. 2004. Wlds-mediated protection of dopaminergic fibers in an animal model of Parkinson disease. *Curr. Biol.* 14:326-330. doi: 10.1016/j.cub.2004.01.053.

Sasaki, Y., T. Nakagawa, X. Mao, A. DiAntonio, and J. Milbrandt. 2016. NMNAT1 inhibits axon degeneration via blockade of SARM1-mediated NAD+ depletion. *Elife.* 5. doi:10.7554/eLife.19749.

Sasaki, Y., B. P. S. Vohra, F. E. Lund, and J. Milbrandt. 2009. Nicotinamide Mononucleotide Adenylyl Transferase-Mediated Axonal Protection Requires Enzymatic Activity But Not Increased Levels of Neuronal Nicotinamide Adenine Dinucleotide. *J. Neurosci.* 29:5525-5535. doi: 10.1523/JNEUROSCI.5469-08.2009.

Summers, D. W., D. A. Gibson, A. DiAntonio, and J. Milbrandt. 2016. SARM1-specific motifs in the TIR domain enable NAD+ loss and regulate injury-induced SARM1 activation. *Proc. Natl. Acad. Sci. U.S.A.* 113: E6271-E6280. doi:10.1073/pnas.1601506113.

Sumner, C. J., and T. O. Crawford. 2018. Two breakthrough gene-targeted treatments for spinal muscular atrophy: challenges remain. *Journal of Clinical Investigation.* 128: 3219-3227. doi:10.1172/JCI121658.

Szretter, K. J., M. A. Samuel, S. Gilfillan, A. Fuchs, M. Colonna, and M. S. Diamond. 2009. The immune adaptor molecule SARM modulates tumor necrosis factor alpha production and microglia activation in the brainstem and restricts West Nile Virus pathogenesis. *J. Virol.* 83:9329-9338. doi:10.1128/JVI.00836-09.

Tagliaferro, P., and R. E. Burke. 2016. Retrograde Axonal Degeneration in Parkinson Disease. *J Parkinsons Dis.* 6:1-15. doi:10.3233/JPD-150769.

Turkiew, E., D. Falconer, N. Reed, and A. Höke. 2017. Deletion of Sarm1 gene is neuroprotective in two models of peripheral neuropathy. *J. Peripher. Nerv. Syst.* 22:162-171. doi:10.1111/jns.12219.

Wang, M. S., A. A. Davis, D. G. Culver, and J. D. Glass. 2002. WIdS mice are resistant to paclitaxel (taxol) neuropathy. *Ann. Neurol.* 52:442-447. doi:10.1002/ana.10300.

Wang, M. S., G. Fang, D. G. Culver, A. A. Davis, M. M. Rich, and J. D. Glass. 2001. The WIdS protein protects against axonal degeneration: a model of gene therapy for peripheral neuropathy. *Ann. Neurol.* 50:773-779.

Yang, J., Z. Wu, N. Renier, D. J. Simon, K. Uryu, D. S. Park, P. A. Greer, C. Tournier, R. J. Davis, and M. Tessier-Lavigne. 2015. Pathological axonal death through a MAPK cascade that triggers a local energy deficit. *Cell.* 160:161-176. doi:10.1016/j.cell.2014.11.053.

Yin, T. C., J. R. Voorhees, R. M. Genova, K. C. Davis, A. M. Madison, J. K. Britt, C. J. Cintron-Perez, L. McDaniel, M. M. Harper, and A. A. Pieper. 2016. Acute Axonal Degeneration Drives Development of Cognitive, Motor, and Visual Deficits after Blast-Mediated Traumatic Brain Injury in Mice. *eNeuro.* 3. doi:10.1523/ENEURO.0220-16.2016.

Ziogas, N. K., and V. E. Koliatsos. 2018. Primary Traumatic Axonopathy in Mice Subjected to Impact Acceleration: A Reappraisal of Pathology and Mechanisms with High-Resolution Anatomical Methods. *J. Neurosci.* 38:4031-4047. doi:10.1523/JNEUROSCI.2343-17.2018.

What is claimed is:

1. A mutant human sterile alpha and TIR motif containing protein 1 (SARM1) polypeptide, comprising the amino acid sequence of SEQ ID NO:1 and having
an amino acid substitution selected from K193A, K193E, K193M, K193Q, and K193R relative to SEQ ID NO:1;
an amino acid substitution selected from H685Y and H685A relative to SEQ ID NO: 1;
amino acid substitutions K193R and H685A relative to SEQ ID NO:1;
amino acid substitutions K193R, H194A, and H685A relative to SEQ ID NO:1;
an amino acid substitution E189K relative to SEQ ID NO:1; an amino acid substitution R570A relative to SEQ ID NO: 1; or
an amino acid substitution H190A relative to SEQ ID NO:1.

2. The polypeptide of claim 1, having the amino acid substitution selected from K193A, K193E, K193M, K193Q, and K193R.

3. The polypeptide of claim 1, having the amino acid substitution R570A.

4. The polypeptide of claim 1, having the amino acid substitutions K193R and H685A.

5. The polypeptide of claim 1, having the amino acid substitution selected from H685A and H685Y.

6. The polypeptide of claim 1, having the amino acid substitutions K193R, H194A, and H685A.

7. The polypeptide of claim 1, having the amino acid substitution E189K.

8. The polypeptide of claim 1, having the amino acid substitution H190A.

9. A composition comprising the polypeptide of claim 1, and a pharmaceutically acceptable excipient.

* * * * *

SEQUENCE LISTING

```
<160> NUMBER OF SEQ ID NOS: 15

<210> SEQ ID NO 1
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 1

Met Val Leu Thr Leu Leu Leu Ser Ala Tyr Lys Leu Cys Arg Phe Phe
1               5                   10                  15

Ala Met Ser Gly Pro Arg Pro Gly Ala Glu Arg Leu Ala Val Pro Gly
            20                  25                  30

Pro Asp Gly Gly Gly Gly Thr Gly Pro Trp Trp Ala Ala Gly Gly Arg
        35                  40                  45

Gly Pro Arg Glu Val Ser Pro Gly Ala Gly Thr Glu Val Gln Asp Ala
    50                  55                  60

Leu Glu Arg Ala Leu Pro Glu Leu Gln Gln Ala Leu Ser Ala Leu Lys
65                  70                  75                  80

Gln Ala Gly Gly Ala Arg Ala Val Gly Ala Gly Leu Ala Glu Val Phe
                85                  90                  95

Gln Leu Val Glu Glu Ala Trp Leu Leu Pro Ala Val Gly Arg Glu Val
            100                 105                 110

Ala Gln Gly Leu Cys Asp Ala Ile Arg Leu Asp Gly Gly Leu Asp Leu
        115                 120                 125

Leu Leu Arg Leu Leu Gln Ala Pro Glu Leu Glu Thr Arg Val Gln Ala
    130                 135                 140

Ala Arg Leu Leu Glu Gln Ile Leu Val Ala Glu Asn Arg Asp Arg Val
```

-continued

```
                 145                    150                    155                    160

Ala Arg Ile Gly Leu Gly Val Ile Leu Asn Leu Ala Lys Glu Arg Glu
                 165                    170                    175

Pro Val Glu Leu Ala Arg Ser Val Ala Gly Ile Leu Glu His Met Phe
                 180                    185                    190

Lys His Ser Glu Glu Thr Cys Gln Arg Leu Val Ala Ala Gly Gly Leu
                 195                    200                    205

Asp Ala Val Leu Tyr Trp Cys Arg Arg Thr Asp Pro Ala Leu Leu Arg
         210                    215                    220

His Cys Ala Leu Ala Leu Gly Asn Cys Ala Leu His Gly Gly Gln Ala
225                    230                    235                    240

Val Gln Arg Arg Met Val Glu Lys Arg Ala Ala Glu Trp Leu Phe Pro
                 245                    250                    255

Leu Ala Phe Ser Lys Glu Asp Glu Leu Leu Arg Leu His Ala Cys Leu
                 260                    265                    270

Ala Val Ala Val Leu Ala Thr Asn Lys Glu Val Glu Arg Glu Val Glu
                 275                    280                    285

Arg Ser Gly Thr Leu Ala Leu Val Glu Pro Leu Val Ala Ser Leu Asp
         290                    295                    300

Pro Gly Arg Phe Ala Arg Cys Leu Val Asp Ala Ser Asp Thr Ser Gln
305                    310                    315                    320

Gly Arg Gly Pro Asp Asp Leu Gln Arg Leu Val Pro Leu Leu Asp Ser
                 325                    330                    335

Asn Arg Leu Glu Ala Gln Cys Ile Gly Ala Phe Tyr Leu Cys Ala Glu
                 340                    345                    350

Ala Ala Ile Lys Ser Leu Gln Gly Lys Thr Lys Val Phe Ser Asp Ile
         355                    360                    365

Gly Ala Ile Gln Ser Leu Lys Arg Leu Val Ser Tyr Ser Thr Asn Gly
         370                    375                    380

Thr Lys Ser Ala Leu Ala Lys Arg Ala Leu Arg Leu Leu Gly Glu Glu
385                    390                    395                    400

Val Pro Arg Pro Ile Leu Pro Ser Val Pro Ser Trp Lys Glu Ala Glu
                 405                    410                    415

Val Gln Thr Trp Leu Gln Gln Ile Gly Phe Ser Lys Tyr Cys Glu Ser
                 420                    425                    430

Phe Arg Glu Gln Gln Val Asp Gly Asp Leu Leu Leu Arg Leu Thr Glu
                 435                    440                    445

Glu Glu Leu Gln Thr Asp Leu Gly Met Lys Ser Gly Ile Thr Arg Lys
         450                    455                    460

Arg Phe Phe Arg Glu Leu Thr Glu Leu Lys Thr Phe Ala Asn Tyr Ser
465                    470                    475                    480

Thr Cys Asp Arg Ser Asn Leu Ala Asp Trp Leu Gly Ser Leu Asp Pro
                 485                    490                    495

Arg Phe Arg Gln Tyr Thr Tyr Gly Leu Val Ser Cys Gly Leu Asp Arg
                 500                    505                    510

Ser Leu Leu His Arg Val Ser Glu Gln Gln Leu Leu Glu Asp Cys Gly
         515                    520                    525

Ile His Leu Gly Val His Arg Ala Arg Ile Leu Thr Ala Ala Arg Glu
         530                    535                    540

Met Leu His Ser Pro Leu Pro Cys Thr Gly Gly Lys Pro Ser Gly Asp
545                    550                    555                    560

Thr Pro Asp Val Phe Ile Ser Tyr Arg Arg Asn Ser Gly Ser Gln Leu
                 565                    570                    575
```

-continued

```
Ala Ser Leu Leu Lys Val His Leu Gln Leu His Gly Phe Ser Val Phe
        580                 585                 590

Ile Asp Val Glu Lys Leu Glu Ala Gly Lys Phe Glu Asp Lys Leu Ile
        595                 600                 605

Gln Ser Val Met Gly Ala Arg Asn Phe Val Leu Val Leu Ser Pro Gly
        610                 615                 620

Ala Leu Asp Lys Cys Met Gln Asp His Asp Cys Lys Asp Trp Val His
625                 630                 635                 640

Lys Glu Ile Val Thr Ala Leu Ser Cys Gly Lys Asn Ile Val Pro Ile
                645                 650                 655

Ile Asp Gly Phe Glu Trp Pro Glu Pro Gln Val Leu Pro Glu Asp Met
                660                 665                 670

Gln Ala Val Leu Thr Phe Asn Gly Ile Lys Trp Ser His Glu Tyr Gln
        675                 680                 685

Glu Ala Thr Ile Glu Lys Ile Ile Arg Phe Leu Gln Gly Arg Ser Ser
        690                 695                 700

Arg Asp Ser Ser Ala Gly Ser Asp Thr Ser Leu Glu Gly Ala Ala Pro
705                 710                 715                 720

Met Gly Pro Thr

<210> SEQ ID NO 2
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 2

Met Val Leu Thr Leu Leu Leu Ser Ala Tyr Lys Leu Cys Arg Phe Phe
1               5                   10                  15

Ala Met Ser Gly Pro Arg Pro Gly Ala Glu Arg Leu Ala Val Pro Gly
                20                  25                  30

Pro Asp Gly Gly Gly Gly Thr Gly Pro Trp Trp Ala Ala Gly Gly Arg
                35                  40                  45

Gly Pro Arg Glu Val Ser Pro Gly Ala Gly Thr Glu Val Gln Asp Ala
        50                  55                  60

Leu Glu Arg Ala Leu Pro Glu Leu Gln Gln Ala Leu Ser Ala Leu Lys
65                  70                  75                  80

Gln Ala Gly Gly Ala Arg Ala Val Gly Ala Gly Leu Ala Glu Val Phe
                85                  90                  95

Gln Leu Val Glu Glu Ala Trp Leu Leu Pro Ala Val Gly Arg Glu Val
                100                 105                 110

Ala Gln Gly Leu Cys Asp Ala Ile Arg Leu Asp Gly Gly Leu Asp Leu
        115                 120                 125

Leu Leu Arg Leu Leu Gln Ala Pro Glu Leu Glu Thr Arg Val Gln Ala
        130                 135                 140

Ala Arg Leu Leu Glu Gln Ile Leu Val Ala Glu Asn Arg Asp Arg Val
145                 150                 155                 160

Ala Arg Ile Gly Leu Gly Val Ile Leu Asn Leu Ala Lys Glu Arg Glu
                165                 170                 175

Pro Val Glu Leu Ala Arg Ser Val Ala Gly Ile Leu Glu His Met Tyr
                180                 185                 190

Lys His Ser Glu Glu Thr Cys Gln Arg Leu Val Ala Ala Gly Gly Leu
        195                 200                 205
```

-continued

```
Asp Ala Val Leu Tyr Trp Cys Arg Arg Thr Asp Pro Ala Leu Leu Arg
    210                 215                 220

His Cys Ala Leu Ala Leu Gly Asn Cys Ala Leu His Gly Gly Gln Ala
225                 230                 235                 240

Val Gln Arg Arg Met Val Glu Lys Arg Ala Ala Glu Trp Leu Phe Pro
                245                 250                 255

Leu Ala Phe Ser Lys Glu Asp Glu Leu Leu Arg Leu His Ala Cys Leu
                260                 265                 270

Ala Val Ala Val Leu Ala Thr Asn Lys Glu Val Glu Arg Glu Val Glu
                275                 280                 285

Arg Ser Gly Thr Leu Ala Leu Val Glu Pro Leu Val Ala Ser Leu Asp
    290                 295                 300

Pro Gly Arg Phe Ala Arg Cys Leu Val Asp Ala Ser Asp Thr Ser Gln
305                 310                 315                 320

Gly Arg Gly Pro Asp Asp Leu Gln Arg Leu Val Pro Leu Leu Asp Ser
                325                 330                 335

Asn Arg Leu Glu Ala Gln Cys Ile Gly Ala Phe Tyr Leu Cys Ala Glu
                340                 345                 350

Ala Ala Ile Lys Ser Leu Gln Gly Lys Thr Lys Val Phe Ser Asp Ile
                355                 360                 365

Gly Ala Ile Gln Ser Leu Lys Arg Leu Val Ser Tyr Ser Thr Asn Gly
    370                 375                 380

Thr Lys Ser Ala Leu Ala Lys Arg Ala Leu Arg Leu Leu Gly Glu Glu
385                 390                 395                 400

Val Pro Arg Pro Ile Leu Pro Ser Val Pro Ser Trp Lys Glu Ala Glu
                405                 410                 415

Val Gln Thr Trp Leu Gln Gln Ile Gly Phe Ser Lys Tyr Cys Glu Ser
                420                 425                 430

Phe Arg Glu Gln Gln Val Asp Gly Asp Leu Leu Leu Arg Leu Thr Glu
                435                 440                 445

Glu Glu Leu Gln Thr Asp Leu Gly Met Lys Ser Gly Ile Thr Arg Lys
    450                 455                 460

Arg Phe Phe Arg Glu Leu Thr Glu Leu Lys Thr Phe Ala Asn Tyr Ser
465                 470                 475                 480

Thr Cys Asp Arg Ser Asn Leu Ala Asp Trp Leu Gly Ser Leu Asp Pro
                485                 490                 495

Arg Phe Arg Gln Tyr Thr Tyr Gly Leu Val Ser Cys Gly Leu Asp Arg
                500                 505                 510

Ser Leu Leu His Arg Val Ser Glu Gln Gln Leu Leu Glu Asp Cys Gly
    515                 520                 525

Ile His Leu Gly Val His Arg Ala Arg Ile Leu Thr Ala Ala Arg Glu
    530                 535                 540

Met Leu His Ser Pro Leu Pro Cys Thr Gly Gly Lys Pro Ser Gly Asp
545                 550                 555                 560

Thr Pro Asp Val Phe Ile Ser Tyr Arg Arg Asn Ser Gly Ser Gln Leu
                565                 570                 575

Ala Ser Leu Leu Lys Val His Leu Gln Leu His Gly Phe Ser Val Phe
                580                 585                 590

Ile Asp Val Glu Lys Leu Glu Ala Gly Lys Phe Glu Asp Lys Leu Ile
                595                 600                 605

Gln Ser Val Met Gly Ala Arg Asn Phe Val Leu Val Leu Ser Pro Gly
    610                 615                 620

Ala Leu Asp Lys Cys Met Gln Asp His Asp Cys Lys Asp Trp Val His
```

-continued

```
625                630                635                640

Lys Glu Ile Val Thr Ala Leu Ser Cys Gly Lys Asn Ile Val Pro Ile
            645                650                655

Ile Asp Gly Phe Glu Trp Pro Glu Pro Gln Val Leu Pro Glu Asp Met
            660                665                670

Gln Ala Val Leu Thr Phe Asn Gly Ile Lys Trp Ser His Glu Tyr Gln
            675                680                685

Glu Ala Thr Ile Glu Lys Ile Ile Arg Phe Leu Gln Gly Arg Ser Ser
        690                695                700

Arg Asp Ser Ser Ala Gly Ser Asp Thr Ser Leu Glu Gly Ala Ala Pro
705                710                715                720

Met Gly Pro Thr

<210> SEQ ID NO 3
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 3

Met Val Leu Thr Leu Leu Leu Ser Ala Tyr Lys Leu Cys Arg Phe Phe
1               5                   10                  15

Ala Met Ser Gly Pro Arg Pro Gly Ala Glu Arg Leu Ala Val Pro Gly
            20                  25                  30

Pro Asp Gly Gly Gly Gly Thr Gly Pro Trp Trp Ala Ala Gly Gly Arg
            35                  40                  45

Gly Pro Arg Glu Val Ser Pro Gly Ala Gly Thr Glu Val Gln Asp Ala
        50                  55                  60

Leu Glu Arg Ala Leu Pro Glu Leu Gln Gln Ala Leu Ser Ala Leu Lys
65                  70                  75                  80

Gln Ala Gly Gly Ala Arg Ala Val Gly Ala Gly Leu Ala Glu Val Phe
                85                  90                  95

Gln Leu Val Glu Glu Ala Trp Leu Leu Pro Ala Val Gly Arg Glu Val
            100                 105                 110

Ala Gln Gly Leu Cys Asp Ala Ile Arg Leu Asp Gly Gly Leu Asp Leu
            115                 120                 125

Leu Leu Arg Leu Leu Gln Ala Pro Glu Leu Glu Thr Arg Val Gln Ala
        130                 135                 140

Ala Arg Leu Leu Glu Gln Ile Leu Val Ala Glu Asn Arg Asp Arg Val
145                 150                 155                 160

Ala Arg Ile Gly Leu Gly Val Ile Leu Asn Leu Ala Lys Glu Arg Glu
            165                 170                 175

Pro Val Glu Leu Ala Arg Ser Val Ala Gly Ile Leu Glu His Met Phe
            180                 185                 190

Arg His Ser Glu Glu Thr Cys Gln Arg Leu Val Ala Ala Gly Gly Leu
            195                 200                 205

Asp Ala Val Leu Tyr Trp Cys Arg Arg Thr Asp Pro Ala Leu Leu Arg
        210                 215                 220

His Cys Ala Leu Ala Leu Gly Asn Cys Ala Leu His Gly Gly Gln Ala
225                 230                 235                 240

Val Gln Arg Arg Met Val Glu Lys Arg Ala Ala Glu Trp Leu Phe Pro
                245                 250                 255

Leu Ala Phe Ser Lys Glu Asp Glu Leu Leu Arg Leu His Ala Cys Leu
            260                 265                 270
```

-continued

```
Ala Val Ala Val Leu Ala Thr Asn Lys Glu Val Glu Arg Glu Val Glu
        275                 280                 285

Arg Ser Gly Thr Leu Ala Leu Val Glu Pro Leu Val Ala Ser Leu Asp
        290                 295                 300

Pro Gly Arg Phe Ala Arg Cys Leu Val Asp Ala Ser Asp Thr Ser Gln
305                 310                 315                 320

Gly Arg Gly Pro Asp Asp Leu Gln Arg Leu Val Pro Leu Leu Asp Ser
                325                 330                 335

Asn Arg Leu Glu Ala Gln Cys Ile Gly Ala Phe Tyr Leu Cys Ala Glu
            340                 345                 350

Ala Ala Ile Lys Ser Leu Gln Gly Lys Thr Lys Val Phe Ser Asp Ile
            355                 360                 365

Gly Ala Ile Gln Ser Leu Lys Arg Leu Val Ser Tyr Ser Thr Asn Gly
        370                 375                 380

Thr Lys Ser Ala Leu Ala Lys Arg Ala Leu Arg Leu Leu Gly Glu Glu
385                 390                 395                 400

Val Pro Arg Pro Ile Leu Pro Ser Val Pro Ser Trp Lys Glu Ala Glu
                405                 410                 415

Val Gln Thr Trp Leu Gln Gln Ile Gly Phe Ser Lys Tyr Cys Glu Ser
                420                 425                 430

Phe Arg Glu Gln Gln Val Asp Gly Asp Leu Leu Leu Arg Leu Thr Glu
            435                 440                 445

Glu Glu Leu Gln Thr Asp Leu Gly Met Lys Ser Gly Ile Thr Arg Lys
        450                 455                 460

Arg Phe Phe Arg Glu Leu Thr Glu Leu Lys Thr Phe Ala Asn Tyr Ser
465                 470                 475                 480

Thr Cys Asp Arg Ser Asn Leu Ala Asp Trp Leu Gly Ser Leu Asp Pro
                485                 490                 495

Arg Phe Arg Gln Tyr Thr Tyr Gly Leu Val Ser Cys Gly Leu Asp Arg
                500                 505                 510

Ser Leu Leu His Arg Val Ser Glu Gln Gln Leu Leu Glu Asp Cys Gly
            515                 520                 525

Ile His Leu Gly Val His Arg Ala Arg Ile Leu Thr Ala Ala Arg Glu
        530                 535                 540

Met Leu His Ser Pro Leu Pro Cys Thr Gly Gly Lys Pro Ser Gly Asp
545                 550                 555                 560

Thr Pro Asp Val Phe Ile Ser Tyr Arg Arg Asn Ser Gly Ser Gln Leu
                565                 570                 575

Ala Ser Leu Leu Lys Val His Leu Gln Leu His Gly Phe Ser Val Phe
            580                 585                 590

Ile Asp Val Glu Lys Leu Glu Ala Gly Lys Phe Glu Asp Lys Leu Ile
            595                 600                 605

Gln Ser Val Met Gly Ala Arg Asn Phe Val Leu Val Leu Ser Pro Gly
        610                 615                 620

Ala Leu Asp Lys Cys Met Gln Asp His Asp Cys Lys Asp Trp Val His
625                 630                 635                 640

Lys Glu Ile Val Thr Ala Leu Ser Cys Gly Lys Asn Ile Val Pro Ile
                645                 650                 655

Ile Asp Gly Phe Glu Trp Pro Glu Pro Gln Val Leu Pro Glu Asp Met
                660                 665                 670

Gln Ala Val Leu Thr Phe Asn Gly Ile Lys Trp Ser His Glu Tyr Gln
        675                 680                 685
```

-continued

```
Glu Ala Thr Ile Glu Lys Ile Ile Arg Phe Leu Gln Gly Arg Ser Ser
    690             695             700

Arg Asp Ser Ser Ala Gly Ser Asp Thr Ser Leu Glu Gly Ala Ala Pro
705             710             715             720

Met Gly Pro Thr

<210> SEQ ID NO 4
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 4

Met Val Leu Thr Leu Leu Leu Ser Ala Tyr Lys Leu Cys Arg Phe Phe
1               5               10              15

Ala Met Ser Gly Pro Arg Pro Gly Ala Glu Arg Leu Ala Val Pro Gly
                20              25              30

Pro Asp Gly Gly Gly Gly Thr Gly Pro Trp Trp Ala Ala Gly Gly Arg
            35              40              45

Gly Pro Arg Glu Val Ser Pro Gly Ala Gly Thr Glu Val Gln Asp Ala
    50              55              60

Leu Glu Arg Ala Leu Pro Glu Leu Gln Gln Ala Leu Ser Ala Leu Lys
65              70              75              80

Gln Ala Gly Gly Ala Arg Ala Val Gly Ala Gly Leu Ala Glu Val Phe
                85              90              95

Gln Leu Val Glu Glu Ala Trp Leu Leu Pro Ala Val Gly Arg Glu Val
            100             105             110

Ala Gln Gly Leu Cys Asp Ala Ile Arg Leu Asp Gly Gly Leu Asp Leu
            115             120             125

Leu Leu Arg Leu Leu Gln Ala Pro Glu Leu Glu Thr Arg Val Gln Ala
    130             135             140

Ala Arg Leu Leu Glu Gln Ile Leu Val Ala Glu Asn Arg Asp Arg Val
145             150             155             160

Ala Arg Ile Gly Leu Gly Val Ile Leu Asn Leu Ala Lys Glu Arg Glu
                165             170             175

Pro Val Glu Leu Ala Arg Ser Val Ala Gly Ile Leu Glu His Met Phe
            180             185             190

Ala His Ser Glu Glu Thr Cys Gln Arg Leu Val Ala Ala Gly Gly Leu
            195             200             205

Asp Ala Val Leu Tyr Trp Cys Arg Arg Thr Asp Pro Ala Leu Leu Arg
    210             215             220

His Cys Ala Leu Ala Leu Gly Asn Cys Ala Leu His Gly Gly Gln Ala
225             230             235             240

Val Gln Arg Arg Met Val Glu Lys Arg Ala Ala Glu Trp Leu Phe Pro
                245             250             255

Leu Ala Phe Ser Lys Glu Asp Glu Leu Leu Arg Leu His Ala Cys Leu
            260             265             270

Ala Val Ala Val Leu Ala Thr Asn Lys Glu Val Glu Arg Glu Val Glu
            275             280             285

Arg Ser Gly Thr Leu Ala Leu Val Glu Pro Leu Val Ala Ser Leu Asp
    290             295             300

Pro Gly Arg Phe Ala Arg Cys Leu Val Asp Ala Ser Asp Thr Ser Gln
305             310             315             320

Gly Arg Gly Pro Asp Asp Leu Gln Arg Leu Val Pro Leu Leu Asp Ser
```

-continued

```
               325               330               335

Asn Arg Leu Glu Ala Gln Cys Ile Gly Ala Phe Tyr Leu Cys Ala Glu
           340               345               350

Ala Ala Ile Lys Ser Leu Gln Gly Lys Thr Lys Val Phe Ser Asp Ile
           355               360               365

Gly Ala Ile Gln Ser Leu Lys Arg Leu Val Ser Tyr Ser Thr Asn Gly
       370               375               380

Thr Lys Ser Ala Leu Ala Lys Arg Ala Leu Arg Leu Leu Gly Glu Glu
   385               390               395               400

Val Pro Arg Pro Ile Leu Pro Ser Val Pro Ser Trp Lys Glu Ala Glu
               405               410               415

Val Gln Thr Trp Leu Gln Gln Ile Gly Phe Ser Lys Tyr Cys Glu Ser
           420               425               430

Phe Arg Glu Gln Gln Val Asp Gly Asp Leu Leu Leu Arg Leu Thr Glu
           435               440               445

Glu Glu Leu Gln Thr Asp Leu Gly Met Lys Ser Gly Ile Thr Arg Lys
       450               455               460

Arg Phe Phe Arg Glu Leu Thr Glu Leu Lys Thr Phe Ala Asn Tyr Ser
   465               470               475               480

Thr Cys Asp Arg Ser Asn Leu Ala Asp Trp Leu Gly Ser Leu Asp Pro
               485               490               495

Arg Phe Arg Gln Tyr Thr Tyr Gly Leu Val Ser Cys Gly Leu Asp Arg
           500               505               510

Ser Leu Leu His Arg Val Ser Glu Gln Gln Leu Leu Glu Asp Cys Gly
           515               520               525

Ile His Leu Gly Val His Arg Ala Arg Ile Leu Thr Ala Ala Arg Glu
       530               535               540

Met Leu His Ser Pro Leu Pro Cys Thr Gly Gly Lys Pro Ser Gly Asp
   545               550               555               560

Thr Pro Asp Val Phe Ile Ser Tyr Arg Arg Asn Ser Gly Ser Gln Leu
               565               570               575

Ala Ser Leu Leu Lys Val His Leu Gln Leu His Gly Phe Ser Val Phe
           580               585               590

Ile Asp Val Glu Lys Leu Glu Ala Gly Lys Phe Glu Asp Lys Leu Ile
           595               600               605

Gln Ser Val Met Gly Ala Arg Asn Phe Val Leu Val Leu Ser Pro Gly
       610               615               620

Ala Leu Asp Lys Cys Met Gln Asp His Asp Cys Lys Asp Trp Val His
   625               630               635               640

Lys Glu Ile Val Thr Ala Leu Ser Cys Gly Lys Asn Ile Val Pro Ile
               645               650               655

Ile Asp Gly Phe Glu Trp Pro Glu Pro Gln Val Leu Pro Glu Asp Met
           660               665               670

Gln Ala Val Leu Thr Phe Asn Gly Ile Lys Trp Ser His Glu Tyr Gln
           675               680               685

Glu Ala Thr Ile Glu Lys Ile Ile Arg Phe Leu Gln Gly Arg Ser Ser
       690               695               700

Arg Asp Ser Ser Ala Gly Ser Asp Thr Ser Leu Glu Gly Ala Ala Pro
   705               710               715               720

Met Gly Pro Thr
```

<210> SEQ ID NO 5
<211> LENGTH: 724

-continued

```
<212> TYPE: PRT
<213> ORGANISM: Artificial Sequence
<220> FEATURE:
<223> OTHER INFORMATION: SYNTHESIZED

<400> SEQUENCE: 5

Met Val Leu Thr Leu Leu Leu Ser Ala Tyr Lys Leu Cys Arg Phe Phe
1               5                   10                  15

Ala Met Ser Gly Pro Arg Pro Gly Ala Glu Arg Leu Ala Val Pro Gly
                20                  25                  30

Pro Asp Gly Gly Gly Gly Thr Gly Pro Trp Trp Ala Ala Gly Gly Arg
            35                  40                  45

Gly Pro Arg Glu Val Ser Pro Gly Ala Gly Thr Glu Val Gln Asp Ala
        50                  55                  60

Leu Glu Arg Ala Leu Pro Glu Leu Gln Gln Ala Leu Ser Ala Leu Lys
65                  70                  75                  80

Gln Ala Gly Gly Ala Arg Ala Val Gly Ala Gly Leu Ala Glu Val Phe
                85                  90                  95

Gln Leu Val Glu Glu Ala Trp Leu Leu Pro Ala Val Gly Arg Glu Val
            100                 105                 110

Ala Gln Gly Leu Cys Asp Ala Ile Arg Leu Asp Gly Gly Leu Asp Leu
            115                 120                 125

Leu Leu Arg Leu Leu Gln Ala Pro Glu Leu Glu Thr Arg Val Gln Ala
        130                 135                 140

Ala Arg Leu Leu Glu Gln Ile Leu Val Ala Glu Asn Arg Asp Arg Val
145                 150                 155                 160

Ala Arg Ile Gly Leu Gly Val Ile Leu Asn Leu Ala Lys Glu Arg Glu
                165                 170                 175

Pro Val Glu Leu Ala Arg Ser Val Ala Gly Ile Leu Glu His Met Phe
            180                 185                 190

Gln His Ser Glu Glu Thr Cys Gln Arg Leu Val Ala Ala Gly Gly Leu
            195                 200                 205

Asp Ala Val Leu Tyr Trp Cys Arg Arg Thr Asp Pro Ala Leu Leu Arg
        210                 215                 220

His Cys Ala Leu Ala Leu Gly Asn Cys Ala Leu His Gly Gly Gln Ala
225                 230                 235                 240

Val Gln Arg Arg Met Val Glu Lys Arg Ala Ala Glu Trp Leu Phe Pro
                245                 250                 255

Leu Ala Phe Ser Lys Glu Asp Glu Leu Leu Arg Leu His Ala Cys Leu
                260                 265                 270

Ala Val Ala Val Leu Ala Thr Asn Lys Glu Val Glu Arg Glu Val Glu
            275                 280                 285

Arg Ser Gly Thr Leu Ala Leu Val Glu Pro Leu Val Ala Ser Leu Asp
        290                 295                 300

Pro Gly Arg Phe Ala Arg Cys Leu Val Asp Ala Ser Asp Thr Ser Gln
305                 310                 315                 320

Gly Arg Gly Pro Asp Asp Leu Gln Arg Leu Val Pro Leu Leu Asp Ser
                325                 330                 335

Asn Arg Leu Glu Ala Gln Cys Ile Gly Ala Phe Tyr Leu Cys Ala Glu
            340                 345                 350

Ala Ala Ile Lys Ser Leu Gln Gly Lys Thr Lys Val Phe Ser Asp Ile
            355                 360                 365

Gly Ala Ile Gln Ser Leu Lys Arg Leu Val Ser Tyr Ser Thr Asn Gly
        370                 375                 380
```

-continued

```
Thr Lys Ser Ala Leu Ala Lys Arg Ala Leu Arg Leu Leu Gly Glu Glu
385             390             395             400

Val Pro Arg Pro Ile Leu Pro Ser Val Pro Ser Trp Lys Glu Ala Glu
                405             410             415

Val Gln Thr Trp Leu Gln Gln Ile Gly Phe Ser Lys Tyr Cys Glu Ser
            420             425             430

Phe Arg Glu Gln Gln Val Asp Gly Asp Leu Leu Leu Arg Leu Thr Glu
            435             440             445

Glu Glu Leu Gln Thr Asp Leu Gly Met Lys Ser Gly Ile Thr Arg Lys
    450             455             460

Arg Phe Phe Arg Glu Leu Thr Glu Leu Lys Thr Phe Ala Asn Tyr Ser
465             470             475             480

Thr Cys Asp Arg Ser Asn Leu Ala Asp Trp Leu Gly Ser Leu Asp Pro
            485             490             495

Arg Phe Arg Gln Tyr Thr Tyr Gly Leu Val Ser Cys Gly Leu Asp Arg
            500             505             510

Ser Leu Leu His Arg Val Ser Glu Gln Gln Leu Leu Glu Asp Cys Gly
            515             520             525

Ile His Leu Gly Val His Arg Ala Arg Ile Leu Thr Ala Ala Arg Glu
    530             535             540

Met Leu His Ser Pro Leu Pro Cys Thr Gly Gly Lys Pro Ser Gly Asp
545             550             555             560

Thr Pro Asp Val Phe Ile Ser Tyr Arg Arg Asn Ser Gly Ser Gln Leu
            565             570             575

Ala Ser Leu Leu Lys Val His Leu Gln Leu His Gly Phe Ser Val Phe
            580             585             590

Ile Asp Val Glu Lys Leu Glu Ala Gly Lys Phe Glu Asp Lys Leu Ile
            595             600             605

Gln Ser Val Met Gly Ala Arg Asn Phe Val Leu Val Leu Ser Pro Gly
    610             615             620

Ala Leu Asp Lys Cys Met Gln Asp His Asp Cys Lys Asp Trp Val His
625             630             635             640

Lys Glu Ile Val Thr Ala Leu Ser Cys Gly Lys Asn Ile Val Pro Ile
            645             650             655

Ile Asp Gly Phe Glu Trp Pro Glu Pro Gln Val Leu Pro Glu Asp Met
            660             665             670

Gln Ala Val Leu Thr Phe Asn Gly Ile Lys Trp Ser His Glu Tyr Gln
    675             680             685

Glu Ala Thr Ile Glu Lys Ile Ile Arg Phe Leu Gln Gly Arg Ser Ser
    690             695             700

Arg Asp Ser Ser Ala Gly Ser Asp Thr Ser Leu Glu Gly Ala Ala Pro
705             710             715             720

Met Gly Pro Thr
```

```
<210> SEQ ID NO 6
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 6

Met Val Leu Thr Leu Leu Leu Ser Ala Tyr Lys Leu Cys Arg Phe Phe
1               5               10              15

Ala Met Ser Gly Pro Arg Pro Gly Ala Glu Arg Leu Ala Val Pro Gly
```

-continued

```
                20                25                30

Pro Asp Gly Gly Gly Gly Thr Gly Pro Trp Trp Ala Ala Gly Gly Arg
            35                40                45

Gly Pro Arg Glu Val Ser Pro Gly Ala Gly Thr Glu Val Gln Asp Ala
        50                55                60

Leu Glu Arg Ala Leu Pro Glu Leu Gln Gln Ala Leu Ser Ala Leu Lys
65                70                75                80

Gln Ala Gly Gly Ala Arg Ala Val Gly Ala Gly Leu Ala Glu Val Phe
                85                90                95

Gln Leu Val Glu Glu Ala Trp Leu Leu Pro Ala Val Gly Arg Glu Val
            100               105               110

Ala Gln Gly Leu Cys Asp Ala Ile Arg Leu Asp Gly Gly Leu Asp Leu
        115               120               125

Leu Leu Arg Leu Leu Gln Ala Pro Glu Leu Glu Thr Arg Val Gln Ala
        130               135               140

Ala Arg Leu Leu Glu Gln Ile Leu Val Ala Glu Asn Arg Asp Arg Val
145               150               155               160

Ala Arg Ile Gly Leu Gly Val Ile Leu Asn Leu Ala Lys Glu Arg Glu
            165               170               175

Pro Val Glu Leu Ala Arg Ser Val Ala Gly Ile Leu Glu His Met Phe
            180               185               190

Glu His Ser Glu Glu Thr Cys Gln Arg Leu Val Ala Ala Gly Gly Leu
            195               200               205

Asp Ala Val Leu Tyr Trp Cys Arg Arg Thr Asp Pro Ala Leu Leu Arg
        210               215               220

His Cys Ala Leu Ala Leu Gly Asn Cys Ala Leu His Gly Gly Gln Ala
225               230               235               240

Val Gln Arg Arg Met Val Glu Lys Arg Ala Ala Glu Trp Leu Phe Pro
            245               250               255

Leu Ala Phe Ser Lys Glu Asp Glu Leu Leu Arg Leu His Ala Cys Leu
            260               265               270

Ala Val Ala Val Leu Ala Thr Asn Lys Glu Val Glu Arg Glu Val Glu
        275               280               285

Arg Ser Gly Thr Leu Ala Leu Val Glu Pro Leu Val Ala Ser Leu Asp
    290               295               300

Pro Gly Arg Phe Ala Arg Cys Leu Val Asp Ala Ser Asp Thr Ser Gln
305               310               315               320

Gly Arg Gly Pro Asp Asp Leu Gln Arg Leu Val Pro Leu Leu Asp Ser
            325               330               335

Asn Arg Leu Glu Ala Gln Cys Ile Gly Ala Phe Tyr Leu Cys Ala Glu
            340               345               350

Ala Ala Ile Lys Ser Leu Gln Gly Lys Thr Lys Val Phe Ser Asp Ile
        355               360               365

Gly Ala Ile Gln Ser Leu Lys Arg Leu Val Ser Tyr Ser Thr Asn Gly
        370               375               380

Thr Lys Ser Ala Leu Ala Lys Arg Ala Leu Arg Leu Leu Gly Glu Glu
385               390               395               400

Val Pro Arg Pro Ile Leu Pro Ser Val Pro Ser Trp Lys Glu Ala Glu
            405               410               415

Val Gln Thr Trp Leu Gln Gln Ile Gly Phe Ser Lys Tyr Cys Glu Ser
            420               425               430

Phe Arg Glu Gln Gln Val Asp Gly Asp Leu Leu Leu Arg Leu Thr Glu
            435               440               445
```

-continued

```
Glu Glu Leu Gln Thr Asp Leu Gly Met Lys Ser Gly Ile Thr Arg Lys
    450             455             460

Arg Phe Phe Arg Glu Leu Thr Glu Leu Lys Thr Phe Ala Asn Tyr Ser
465             470             475             480

Thr Cys Asp Arg Ser Asn Leu Ala Asp Trp Leu Gly Ser Leu Asp Pro
            485             490             495

Arg Phe Arg Gln Tyr Thr Tyr Gly Leu Val Ser Cys Gly Leu Asp Arg
            500             505             510

Ser Leu Leu His Arg Val Ser Glu Gln Gln Leu Leu Glu Asp Cys Gly
            515             520             525

Ile His Leu Gly Val His Arg Ala Arg Ile Leu Thr Ala Ala Arg Glu
    530             535             540

Met Leu His Ser Pro Leu Pro Cys Thr Gly Gly Lys Pro Ser Gly Asp
545             550             555             560

Thr Pro Asp Val Phe Ile Ser Tyr Arg Arg Asn Ser Gly Ser Gln Leu
            565             570             575

Ala Ser Leu Leu Lys Val His Leu Gln Leu His Gly Phe Ser Val Phe
            580             585             590

Ile Asp Val Glu Lys Leu Glu Ala Gly Lys Phe Glu Asp Lys Leu Ile
            595             600             605

Gln Ser Val Met Gly Ala Arg Asn Phe Val Leu Val Leu Ser Pro Gly
    610             615             620

Ala Leu Asp Lys Cys Met Gln Asp His Asp Cys Lys Asp Trp Val His
625             630             635             640

Lys Glu Ile Val Thr Ala Leu Ser Cys Gly Lys Asn Ile Val Pro Ile
            645             650             655

Ile Asp Gly Phe Glu Trp Pro Glu Pro Gln Val Leu Pro Glu Asp Met
            660             665             670

Gln Ala Val Leu Thr Phe Asn Gly Ile Lys Trp Ser His Glu Tyr Gln
            675             680             685

Glu Ala Thr Ile Glu Lys Ile Ile Arg Phe Leu Gln Gly Arg Ser Ser
    690             695             700

Arg Asp Ser Ser Ala Gly Ser Asp Thr Ser Leu Glu Gly Ala Ala Pro
705             710             715             720

Met Gly Pro Thr

<210> SEQ ID NO 7
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 7

Met Val Leu Thr Leu Leu Leu Ser Ala Tyr Lys Leu Cys Arg Phe Phe
1               5               10              15

Ala Met Ser Gly Pro Arg Pro Gly Ala Glu Arg Leu Ala Val Pro Gly
            20              25              30

Pro Asp Gly Gly Gly Gly Thr Gly Pro Trp Trp Ala Ala Gly Gly Arg
            35              40              45

Gly Pro Arg Glu Val Ser Pro Gly Ala Gly Thr Glu Val Gln Asp Ala
    50              55              60

Leu Glu Arg Ala Leu Pro Glu Leu Gln Gln Ala Leu Ser Ala Leu Lys
65              70              75              80
```

-continued

```
Gln Ala Gly Gly Ala Arg Ala Val Gly Ala Gly Leu Ala Glu Val Phe
             85                  90                  95

Gln Leu Val Glu Glu Ala Trp Leu Leu Pro Ala Val Gly Arg Glu Val
            100                 105                 110

Ala Gln Gly Leu Cys Asp Ala Ile Arg Leu Asp Gly Gly Leu Asp Leu
            115                 120                 125

Leu Leu Arg Leu Leu Gln Ala Pro Glu Leu Glu Thr Arg Val Gln Ala
    130                 135                 140

Ala Arg Leu Leu Glu Gln Ile Leu Val Ala Glu Asn Arg Asp Arg Val
145                 150                 155                 160

Ala Arg Ile Gly Leu Gly Val Ile Leu Asn Leu Ala Lys Glu Arg Glu
                165                 170                 175

Pro Val Glu Leu Ala Arg Ser Val Ala Gly Ile Leu Glu His Met Phe
            180                 185                 190

Met His Ser Glu Glu Thr Cys Gln Arg Leu Val Ala Ala Gly Gly Leu
            195                 200                 205

Asp Ala Val Leu Tyr Trp Cys Arg Arg Thr Asp Pro Ala Leu Leu Arg
    210                 215                 220

His Cys Ala Leu Ala Leu Gly Asn Cys Ala Leu His Gly Gly Gln Ala
225                 230                 235                 240

Val Gln Arg Arg Met Val Glu Lys Arg Ala Ala Glu Trp Leu Phe Pro
                245                 250                 255

Leu Ala Phe Ser Lys Glu Asp Glu Leu Leu Arg Leu His Ala Cys Leu
            260                 265                 270

Ala Val Ala Val Leu Ala Thr Asn Lys Glu Val Glu Arg Glu Val Glu
            275                 280                 285

Arg Ser Gly Thr Leu Ala Leu Val Glu Pro Leu Val Ala Ser Leu Asp
    290                 295                 300

Pro Gly Arg Phe Ala Arg Cys Leu Val Asp Ala Ser Asp Thr Ser Gln
305                 310                 315                 320

Gly Arg Gly Pro Asp Asp Leu Gln Arg Leu Val Pro Leu Leu Asp Ser
                325                 330                 335

Asn Arg Leu Glu Ala Gln Cys Ile Gly Ala Phe Tyr Leu Cys Ala Glu
            340                 345                 350

Ala Ala Ile Lys Ser Leu Gln Gly Lys Thr Lys Val Phe Ser Asp Ile
            355                 360                 365

Gly Ala Ile Gln Ser Leu Lys Arg Leu Val Ser Tyr Ser Thr Asn Gly
    370                 375                 380

Thr Lys Ser Ala Leu Ala Lys Arg Ala Leu Arg Leu Leu Gly Glu Glu
385                 390                 395                 400

Val Pro Arg Pro Ile Leu Pro Ser Val Pro Ser Trp Lys Glu Ala Glu
                405                 410                 415

Val Gln Thr Trp Leu Gln Gln Ile Gly Phe Ser Lys Tyr Cys Glu Ser
            420                 425                 430

Phe Arg Glu Gln Gln Val Asp Gly Asp Leu Leu Leu Arg Leu Thr Glu
            435                 440                 445

Glu Glu Leu Gln Thr Asp Leu Gly Met Lys Ser Gly Ile Thr Arg Lys
    450                 455                 460

Arg Phe Phe Arg Glu Leu Thr Glu Leu Lys Thr Phe Ala Asn Tyr Ser
465                 470                 475                 480

Thr Cys Asp Arg Ser Asn Leu Ala Asp Trp Leu Gly Ser Leu Asp Pro
                485                 490                 495

Arg Phe Arg Gln Tyr Thr Tyr Gly Leu Val Ser Cys Gly Leu Asp Arg
```

```
                500                 505                 510

Ser Leu Leu His Arg Val Ser Glu Gln Gln Leu Leu Glu Asp Cys Gly
        515                 520                 525

Ile His Leu Gly Val His Arg Ala Arg Ile Leu Thr Ala Ala Arg Glu
        530                 535                 540

Met Leu His Ser Pro Leu Pro Cys Thr Gly Gly Lys Pro Ser Gly Asp
545                 550                 555                 560

Thr Pro Asp Val Phe Ile Ser Tyr Arg Arg Asn Ser Gly Ser Gln Leu
                565                 570                 575

Ala Ser Leu Leu Lys Val His Leu Gln Leu His Gly Phe Ser Val Phe
                580                 585                 590

Ile Asp Val Glu Lys Leu Glu Ala Gly Lys Phe Glu Asp Lys Leu Ile
                595                 600                 605

Gln Ser Val Met Gly Ala Arg Asn Phe Val Leu Val Leu Ser Pro Gly
        610                 615                 620

Ala Leu Asp Lys Cys Met Gln Asp His Asp Cys Lys Asp Trp Val His
625                 630                 635                 640

Lys Glu Ile Val Thr Ala Leu Ser Cys Gly Lys Asn Ile Val Pro Ile
                645                 650                 655

Ile Asp Gly Phe Glu Trp Pro Glu Pro Gln Val Leu Pro Glu Asp Met
                660                 665                 670

Gln Ala Val Leu Thr Phe Asn Gly Ile Lys Trp Ser His Glu Tyr Gln
        675                 680                 685

Glu Ala Thr Ile Glu Lys Ile Ile Arg Phe Leu Gln Gly Arg Ser Ser
        690                 695                 700

Arg Asp Ser Ser Ala Gly Ser Asp Thr Ser Leu Glu Gly Ala Ala Pro
705                 710                 715                 720

Met Gly Pro Thr

<210> SEQ ID NO 8
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 8

Met Val Leu Thr Leu Leu Leu Ser Ala Tyr Lys Leu Cys Arg Phe Phe
1               5                   10                  15

Ala Met Ser Gly Pro Arg Pro Gly Ala Glu Arg Leu Ala Val Pro Gly
                20                  25                  30

Pro Asp Gly Gly Gly Gly Thr Gly Pro Trp Trp Ala Ala Gly Gly Arg
            35                  40                  45

Gly Pro Arg Glu Val Ser Pro Gly Ala Gly Thr Glu Val Gln Asp Ala
        50                  55                  60

Leu Glu Arg Ala Leu Pro Glu Leu Gln Gln Ala Leu Ser Ala Leu Lys
65                  70                  75                  80

Gln Ala Gly Gly Ala Arg Ala Val Gly Ala Gly Leu Ala Glu Val Phe
                85                  90                  95

Gln Leu Val Glu Glu Ala Trp Leu Leu Pro Ala Val Gly Arg Glu Val
            100                 105                 110

Ala Gln Gly Leu Cys Asp Ala Ile Arg Leu Asp Gly Gly Leu Asp Leu
        115                 120                 125

Leu Leu Arg Leu Leu Gln Ala Pro Glu Leu Glu Thr Arg Val Gln Ala
        130                 135                 140
```

-continued

```
Ala Arg Leu Leu Glu Gln Ile Leu Val Ala Glu Asn Arg Asp Arg Val
145             150             155             160

Ala Arg Ile Gly Leu Gly Val Ile Leu Asn Leu Ala Lys Glu Arg Glu
            165             170             175

Pro Val Glu Leu Ala Arg Ser Val Ala Gly Ile Leu Glu His Met Phe
            180             185             190

Lys Ala Ser Glu Glu Thr Cys Gln Arg Leu Val Ala Ala Gly Gly Leu
            195             200             205

Asp Ala Val Leu Tyr Trp Cys Arg Arg Thr Asp Pro Ala Leu Leu Arg
            210             215             220

His Cys Ala Leu Ala Leu Gly Asn Cys Ala Leu His Gly Gly Gln Ala
225             230             235             240

Val Gln Arg Arg Met Val Glu Lys Arg Ala Ala Glu Trp Leu Phe Pro
                245             250             255

Leu Ala Phe Ser Lys Glu Asp Glu Leu Leu Arg Leu His Ala Cys Leu
            260             265             270

Ala Val Ala Val Leu Ala Thr Asn Lys Glu Val Glu Arg Glu Val Glu
            275             280             285

Arg Ser Gly Thr Leu Ala Leu Val Glu Pro Leu Val Ala Ser Leu Asp
            290             295             300

Pro Gly Arg Phe Ala Arg Cys Leu Val Asp Ala Ser Asp Thr Ser Gln
305             310             315             320

Gly Arg Gly Pro Asp Asp Leu Gln Arg Leu Val Pro Leu Leu Asp Ser
                325             330             335

Asn Arg Leu Glu Ala Gln Cys Ile Gly Ala Phe Tyr Leu Cys Ala Glu
            340             345             350

Ala Ala Ile Lys Ser Leu Gln Gly Lys Thr Lys Val Phe Ser Asp Ile
            355             360             365

Gly Ala Ile Gln Ser Leu Lys Arg Leu Val Ser Tyr Ser Thr Asn Gly
            370             375             380

Thr Lys Ser Ala Leu Ala Lys Arg Ala Leu Arg Leu Leu Gly Glu Glu
385             390             395             400

Val Pro Arg Pro Ile Leu Pro Ser Val Pro Ser Trp Lys Glu Ala Glu
                405             410             415

Val Gln Thr Trp Leu Gln Gln Ile Gly Phe Ser Lys Tyr Cys Glu Ser
                420             425             430

Phe Arg Glu Gln Gln Val Asp Gly Asp Leu Leu Leu Arg Leu Thr Glu
            435             440             445

Glu Glu Leu Gln Thr Asp Leu Gly Met Lys Ser Gly Ile Thr Arg Lys
            450             455             460

Arg Phe Phe Arg Glu Leu Thr Glu Leu Lys Thr Phe Ala Asn Tyr Ser
465             470             475             480

Thr Cys Asp Arg Ser Asn Leu Ala Asp Trp Leu Gly Ser Leu Asp Pro
                485             490             495

Arg Phe Arg Gln Tyr Thr Tyr Gly Leu Val Ser Cys Gly Leu Asp Arg
            500             505             510

Ser Leu Leu His Arg Val Ser Glu Gln Gln Leu Leu Glu Asp Cys Gly
            515             520             525

Ile His Leu Gly Val His Arg Ala Arg Ile Leu Thr Ala Ala Arg Glu
            530             535             540

Met Leu His Ser Pro Leu Pro Cys Thr Gly Gly Lys Pro Ser Gly Asp
545             550             555             560
```

-continued

```
Thr Pro Asp Val Phe Ile Ser Tyr Arg Arg Asn Ser Gly Ser Gln Leu
             565                 570             575

Ala Ser Leu Leu Lys Val His Leu Gln Leu His Gly Phe Ser Val Phe
             580                 585             590

Ile Asp Val Glu Lys Leu Glu Ala Gly Lys Phe Glu Asp Lys Leu Ile
             595                 600             605

Gln Ser Val Met Gly Ala Arg Asn Phe Val Leu Val Leu Ser Pro Gly
         610                 615             620

Ala Leu Asp Lys Cys Met Gln Asp His Asp Cys Lys Asp Trp Val His
625                 630                 635                 640

Lys Glu Ile Val Thr Ala Leu Ser Cys Gly Lys Asn Ile Val Pro Ile
             645                 650             655

Ile Asp Gly Phe Glu Trp Pro Glu Pro Gln Val Leu Pro Glu Asp Met
             660                 665             670

Gln Ala Val Leu Thr Phe Asn Gly Ile Lys Trp Ser His Glu Tyr Gln
         675                 680             685

Glu Ala Thr Ile Glu Lys Ile Ile Arg Phe Leu Gln Gly Arg Ser Ser
         690                 695             700

Arg Asp Ser Ser Ala Gly Ser Asp Thr Ser Leu Glu Gly Ala Ala Pro
705                 710                 715                 720

Met Gly Pro Thr

<210> SEQ ID NO 9
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 9

Met Val Leu Thr Leu Leu Leu Ser Ala Tyr Lys Leu Cys Arg Phe Phe
1                 5                 10                 15

Ala Met Ser Gly Pro Arg Pro Gly Ala Glu Arg Leu Ala Val Pro Gly
             20                 25                 30

Pro Asp Gly Gly Gly Gly Thr Gly Pro Trp Trp Ala Ala Gly Gly Arg
             35                 40                 45

Gly Pro Arg Glu Val Ser Pro Gly Ala Gly Thr Glu Val Gln Asp Ala
         50                 55                 60

Leu Glu Arg Ala Leu Pro Glu Leu Gln Gln Ala Leu Ser Ala Leu Lys
65                 70                 75                 80

Gln Ala Gly Gly Ala Arg Ala Val Gly Ala Gly Leu Ala Glu Val Phe
             85                 90                 95

Gln Leu Val Glu Glu Ala Trp Leu Leu Pro Ala Val Gly Arg Glu Val
             100                 105             110

Ala Gln Gly Leu Cys Asp Ala Ile Arg Leu Asp Gly Gly Leu Asp Leu
         115                 120             125

Leu Leu Arg Leu Leu Gln Ala Pro Glu Leu Glu Thr Arg Val Gln Ala
         130                 135             140

Ala Arg Leu Leu Glu Gln Ile Leu Val Ala Glu Asn Arg Asp Arg Val
145                 150                 155             160

Ala Arg Ile Gly Leu Gly Val Ile Leu Asn Leu Ala Lys Glu Arg Glu
             165                 170             175

Pro Val Glu Leu Ala Arg Ser Val Ala Gly Ile Leu Glu His Met Phe
             180                 185             190

Lys His Ser Glu Glu Thr Cys Gln Arg Leu Val Ala Ala Gly Gly Leu
```

```
            195                 200                 205

Asp Ala Val Leu Tyr Trp Cys Arg Arg Thr Asp Pro Ala Leu Leu Arg
    210                 215                 220

His Cys Ala Leu Ala Leu Gly Asn Cys Ala Leu His Gly Gly Gln Ala
225                 230                 235                 240

Val Gln Arg Arg Met Val Glu Lys Arg Ala Ala Glu Trp Leu Phe Pro
                245                 250                 255

Leu Ala Phe Ser Lys Glu Asp Glu Leu Leu Arg Leu His Ala Cys Leu
                260                 265                 270

Ala Val Ala Val Leu Ala Thr Asn Lys Glu Val Glu Arg Glu Val Glu
                275                 280                 285

Arg Ser Gly Thr Leu Ala Leu Val Glu Pro Leu Val Ala Ser Leu Asp
    290                 295                 300

Pro Gly Arg Phe Ala Arg Cys Leu Val Asp Ala Ser Asp Thr Ser Gln
305                 310                 315                 320

Gly Arg Gly Pro Asp Asp Leu Gln Arg Leu Val Pro Leu Leu Asp Ser
                325                 330                 335

Asn Arg Leu Glu Ala Gln Cys Ile Gly Ala Phe Tyr Leu Cys Ala Glu
                340                 345                 350

Ala Ala Ile Lys Ser Leu Gln Gly Lys Thr Lys Val Phe Ser Asp Ile
                355                 360                 365

Gly Ala Ile Gln Ser Leu Lys Arg Leu Val Ser Tyr Ser Thr Asn Gly
    370                 375                 380

Thr Lys Ser Ala Leu Ala Lys Arg Ala Leu Arg Leu Leu Gly Glu Glu
385                 390                 395                 400

Val Pro Arg Pro Ile Leu Pro Ser Val Pro Ser Trp Lys Glu Ala Glu
                405                 410                 415

Val Gln Thr Trp Leu Gln Gln Ile Gly Phe Ser Lys Tyr Cys Glu Ser
                420                 425                 430

Phe Arg Glu Gln Gln Val Asp Gly Asp Leu Leu Leu Arg Leu Thr Glu
                435                 440                 445

Glu Glu Leu Gln Thr Asp Leu Gly Met Lys Ser Gly Ile Thr Arg Lys
    450                 455                 460

Arg Phe Phe Arg Glu Leu Thr Glu Leu Lys Thr Phe Ala Asn Tyr Ser
465                 470                 475                 480

Thr Cys Asp Arg Ser Asn Leu Ala Asp Trp Leu Gly Ser Leu Asp Pro
                485                 490                 495

Arg Phe Arg Gln Tyr Thr Tyr Gly Leu Val Ser Cys Gly Leu Asp Arg
                500                 505                 510

Ser Leu Leu His Arg Val Ser Glu Gln Gln Leu Leu Glu Asp Cys Gly
                515                 520                 525

Ile His Leu Gly Val His Arg Ala Arg Ile Leu Thr Ala Ala Arg Glu
    530                 535                 540

Met Leu His Ser Pro Leu Pro Cys Thr Gly Gly Lys Pro Ser Gly Asp
545                 550                 555                 560

Thr Pro Asp Val Phe Ile Ser Tyr Arg Arg Asn Ser Gly Ser Gln Leu
                565                 570                 575

Ala Ser Leu Leu Lys Val His Leu Gln Leu His Gly Phe Ser Val Phe
                580                 585                 590

Ile Asp Val Glu Lys Leu Glu Ala Gly Lys Phe Glu Asp Lys Leu Ile
                595                 600                 605

Gln Ser Val Met Gly Ala Arg Asn Phe Val Leu Val Leu Ser Pro Gly
    610                 615                 620
```

-continued

```
Ala Leu Asp Lys Cys Met Gln Asp His Asp Cys Lys Asp Trp Val His
625                 630             635             640

Lys Ala Ile Val Thr Ala Leu Ser Cys Gly Lys Asn Ile Val Pro Ile
                645             650             655

Ile Asp Gly Phe Glu Trp Pro Glu Pro Gln Val Leu Pro Glu Asp Met
            660             665             670

Gln Ala Val Leu Thr Phe Asn Gly Ile Lys Trp Ser His Glu Tyr Gln
        675             680             685

Glu Ala Thr Ile Glu Lys Ile Ile Arg Phe Leu Gln Gly Arg Ser Ser
    690             695             700

Arg Asp Ser Ser Ala Gly Ser Asp Thr Ser Leu Glu Gly Ala Ala Pro
705             710             715             720

Met Gly Pro Thr

<210> SEQ ID NO 10
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 10

Met Val Leu Thr Leu Leu Leu Ser Ala Tyr Lys Leu Cys Arg Phe Phe
1               5               10              15

Ala Met Ser Gly Pro Arg Pro Gly Ala Glu Arg Leu Ala Val Pro Gly
            20              25              30

Pro Asp Gly Gly Gly Gly Thr Gly Pro Trp Trp Ala Ala Gly Gly Arg
            35              40              45

Gly Pro Arg Glu Val Ser Pro Gly Ala Gly Thr Glu Val Gln Asp Ala
    50              55              60

Leu Glu Arg Ala Leu Pro Glu Leu Gln Gln Ala Leu Ser Ala Leu Lys
65              70              75              80

Gln Ala Gly Gly Ala Arg Ala Val Gly Ala Gly Leu Ala Glu Val Phe
            85              90              95

Gln Leu Val Glu Glu Ala Trp Leu Leu Pro Ala Val Gly Arg Glu Val
            100             105             110

Ala Gln Gly Leu Cys Asp Ala Ile Arg Leu Asp Gly Gly Leu Asp Leu
        115             120             125

Leu Leu Arg Leu Leu Gln Ala Pro Glu Leu Glu Thr Arg Val Gln Ala
    130             135             140

Ala Arg Leu Leu Glu Gln Ile Leu Val Ala Glu Asn Arg Asp Arg Val
145             150             155             160

Ala Arg Ile Gly Leu Gly Val Ile Leu Asn Leu Ala Lys Glu Arg Glu
            165             170             175

Pro Val Glu Leu Ala Arg Ser Val Ala Gly Ile Leu Glu His Met Phe
            180             185             190

Lys His Ser Glu Glu Thr Cys Gln Arg Leu Val Ala Ala Gly Gly Leu
        195             200             205

Asp Ala Val Leu Tyr Trp Cys Arg Arg Thr Asp Pro Ala Leu Leu Arg
    210             215             220

His Cys Ala Leu Ala Leu Gly Asn Cys Ala Leu His Gly Gly Gln Ala
225             230             235             240

Val Gln Arg Arg Met Val Glu Lys Arg Ala Ala Glu Trp Leu Phe Pro
            245             250             255
```

-continued

```
Leu Ala Phe Ser Lys Glu Asp Glu Leu Leu Arg Leu His Ala Cys Leu
             260             265                 270

Ala Val Ala Val Leu Ala Thr Asn Lys Glu Val Glu Arg Glu Val Glu
             275             280             285

Arg Ser Gly Thr Leu Ala Leu Val Glu Pro Leu Val Ala Ser Leu Asp
         290             295             300

Pro Gly Arg Phe Ala Arg Cys Leu Val Asp Ala Ser Asp Thr Ser Gln
305             310             315             320

Gly Arg Gly Pro Asp Asp Leu Gln Arg Leu Val Pro Leu Leu Asp Ser
             325             330             335

Asn Arg Leu Glu Ala Gln Cys Ile Gly Ala Phe Tyr Leu Cys Ala Glu
             340             345             350

Ala Ala Ile Lys Ser Leu Gln Gly Lys Thr Lys Val Phe Ser Asp Ile
             355             360             365

Gly Ala Ile Gln Ser Leu Lys Arg Leu Val Ser Tyr Ser Thr Asn Gly
         370             375             380

Thr Lys Ser Ala Leu Ala Lys Arg Ala Leu Arg Leu Leu Gly Glu Glu
385             390             395             400

Val Pro Arg Pro Ile Leu Pro Ser Val Pro Ser Trp Lys Glu Ala Glu
             405             410             415

Val Gln Thr Trp Leu Gln Gln Ile Gly Phe Ser Lys Tyr Cys Glu Ser
             420             425             430

Phe Arg Glu Gln Gln Val Asp Gly Asp Leu Leu Leu Arg Leu Thr Glu
             435             440             445

Glu Glu Leu Gln Thr Asp Leu Gly Met Lys Ser Gly Ile Thr Arg Lys
         450             455             460

Arg Phe Phe Arg Glu Leu Thr Glu Leu Lys Thr Phe Ala Asn Tyr Ser
465             470             475             480

Thr Cys Asp Arg Ser Asn Leu Ala Asp Trp Leu Gly Ser Leu Asp Pro
             485             490             495

Arg Phe Arg Gln Tyr Thr Tyr Gly Leu Val Ser Cys Gly Leu Asp Arg
             500             505             510

Ser Leu Leu His Arg Val Ser Glu Gln Gln Leu Leu Glu Asp Cys Gly
             515             520             525

Ile His Leu Gly Val His Arg Ala Arg Ile Leu Thr Ala Ala Arg Glu
         530             535             540

Met Leu His Ser Pro Leu Pro Cys Thr Gly Gly Lys Pro Ser Gly Asp
545             550             555             560

Thr Pro Asp Val Phe Ile Ser Tyr Arg Arg Asn Ser Gly Ser Gln Leu
             565             570             575

Ala Ser Leu Leu Lys Val His Leu Gln Leu His Gly Phe Ser Val Phe
             580             585             590

Ile Asp Val Glu Lys Leu Glu Ala Gly Lys Phe Glu Asp Lys Leu Ile
             595             600             605

Gln Ser Val Met Gly Ala Arg Asn Phe Val Leu Val Leu Ser Pro Gly
         610             615             620

Ala Leu Asp Lys Cys Met Gln Asp His Asp Cys Lys Asp Trp Val His
625             630             635             640

Lys Glu Ile Val Thr Ala Leu Ser Cys Gly Lys Asn Ile Val Pro Ile
             645             650             655

Ile Asp Gly Phe Glu Trp Pro Glu Pro Gln Val Leu Pro Glu Asp Met
             660             665             670

Gln Ala Val Leu Thr Phe Asn Gly Ile Lys Trp Ser Ala Glu Tyr Gln
```

-continued

```
            675                 680                 685

Glu Ala Thr Ile Glu Lys Ile Ile Arg Phe Leu Gln Gly Arg Ser Ser
    690                 695                 700

Arg Asp Ser Ser Ala Gly Ser Asp Thr Ser Leu Glu Gly Ala Ala Pro
705                 710                 715                 720

Met Gly Pro Thr

<210> SEQ ID NO 11
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 11

Met Val Leu Thr Leu Leu Leu Ser Ala Tyr Lys Leu Cys Arg Phe Phe
1               5                   10                  15

Ala Met Ser Gly Pro Arg Pro Gly Ala Glu Arg Leu Ala Val Pro Gly
                20                  25                  30

Pro Asp Gly Gly Gly Gly Thr Gly Pro Trp Trp Ala Ala Gly Gly Arg
            35                  40                  45

Gly Pro Arg Glu Val Ser Pro Gly Ala Gly Thr Glu Val Gln Asp Ala
        50                  55                  60

Leu Glu Arg Ala Leu Pro Glu Leu Gln Gln Ala Leu Ser Ala Leu Lys
65                  70                  75                  80

Gln Ala Gly Gly Ala Arg Ala Val Gly Ala Gly Leu Ala Glu Val Phe
                85                  90                  95

Gln Leu Val Glu Glu Ala Trp Leu Leu Pro Ala Val Gly Arg Glu Val
            100                 105                 110

Ala Gln Gly Leu Cys Asp Ala Ile Arg Leu Asp Gly Gly Leu Asp Leu
        115                 120                 125

Leu Leu Arg Leu Leu Gln Ala Pro Glu Leu Glu Thr Arg Val Gln Ala
    130                 135                 140

Ala Arg Leu Leu Glu Gln Ile Leu Val Ala Glu Asn Arg Asp Arg Val
145                 150                 155                 160

Ala Arg Ile Gly Leu Gly Val Ile Leu Asn Leu Ala Lys Glu Arg Glu
                165                 170                 175

Pro Val Glu Leu Ala Arg Ser Val Ala Gly Ile Leu Glu His Met Phe
            180                 185                 190

Arg His Ser Glu Glu Thr Cys Gln Arg Leu Val Ala Ala Gly Gly Leu
        195                 200                 205

Asp Ala Val Leu Tyr Trp Cys Arg Arg Thr Asp Pro Ala Leu Leu Arg
    210                 215                 220

His Cys Ala Leu Ala Leu Gly Asn Cys Ala Leu His Gly Gly Gln Ala
225                 230                 235                 240

Val Gln Arg Arg Met Val Glu Lys Arg Ala Ala Glu Trp Leu Phe Pro
                245                 250                 255

Leu Ala Phe Ser Lys Glu Asp Glu Leu Leu Arg Leu His Ala Cys Leu
            260                 265                 270

Ala Val Ala Val Leu Ala Thr Asn Lys Glu Val Glu Arg Glu Val Glu
        275                 280                 285

Arg Ser Gly Thr Leu Ala Leu Val Glu Pro Leu Val Ala Ser Leu Asp
    290                 295                 300

Pro Gly Arg Phe Ala Arg Cys Leu Val Asp Ala Ser Asp Thr Ser Gln
305                 310                 315                 320
```

-continued

```
Gly Arg Gly Pro Asp Asp Leu Gln Arg Leu Val Pro Leu Leu Asp Ser
            325             330             335

Asn Arg Leu Glu Ala Gln Cys Ile Gly Ala Phe Tyr Leu Cys Ala Glu
            340             345             350

Ala Ala Ile Lys Ser Leu Gln Gly Lys Thr Lys Val Phe Ser Asp Ile
            355             360             365

Gly Ala Ile Gln Ser Leu Lys Arg Leu Val Ser Tyr Ser Thr Asn Gly
    370             375             380

Thr Lys Ser Ala Leu Ala Lys Arg Ala Leu Arg Leu Leu Gly Glu Glu
385             390             395             400

Val Pro Arg Pro Ile Leu Pro Ser Val Pro Ser Trp Lys Glu Ala Glu
            405             410             415

Val Gln Thr Trp Leu Gln Gln Ile Gly Phe Ser Lys Tyr Cys Glu Ser
            420             425             430

Phe Arg Glu Gln Gln Val Asp Gly Asp Leu Leu Leu Arg Leu Thr Glu
            435             440             445

Glu Glu Leu Gln Thr Asp Leu Gly Met Lys Ser Gly Ile Thr Arg Lys
    450             455             460

Arg Phe Phe Arg Glu Leu Thr Glu Leu Lys Thr Phe Ala Asn Tyr Ser
465             470             475             480

Thr Cys Asp Arg Ser Asn Leu Ala Asp Trp Leu Gly Ser Leu Asp Pro
            485             490             495

Arg Phe Arg Gln Tyr Thr Tyr Gly Leu Val Ser Cys Gly Leu Asp Arg
            500             505             510

Ser Leu Leu His Arg Val Ser Glu Gln Gln Leu Leu Glu Asp Cys Gly
            515             520             525

Ile His Leu Gly Val His Arg Ala Arg Ile Leu Thr Ala Ala Arg Glu
    530             535             540

Met Leu His Ser Pro Leu Pro Cys Thr Gly Gly Lys Pro Ser Gly Asp
545             550             555             560

Thr Pro Asp Val Phe Ile Ser Tyr Arg Arg Asn Ser Gly Ser Gln Leu
            565             570             575

Ala Ser Leu Leu Lys Val His Leu Gln Leu His Gly Phe Ser Val Phe
            580             585             590

Ile Asp Val Glu Lys Leu Glu Ala Gly Lys Phe Glu Asp Lys Leu Ile
            595             600             605

Gln Ser Val Met Gly Ala Arg Asn Phe Val Leu Val Leu Ser Pro Gly
    610             615             620

Ala Leu Asp Lys Cys Met Gln Asp His Asp Cys Lys Asp Trp Val His
625             630             635             640

Lys Ala Ile Val Thr Ala Leu Ser Cys Gly Lys Asn Ile Val Pro Ile
            645             650             655

Ile Asp Gly Phe Glu Trp Pro Glu Pro Gln Val Leu Pro Glu Asp Met
            660             665             670

Gln Ala Val Leu Thr Phe Asn Gly Ile Lys Trp Ser His Glu Tyr Gln
            675             680             685

Glu Ala Thr Ile Glu Lys Ile Ile Arg Phe Leu Gln Gly Arg Ser Ser
    690             695             700

Arg Asp Ser Ser Ala Gly Ser Asp Thr Ser Leu Glu Gly Ala Ala Pro
705             710             715             720

Met Gly Pro Thr
```

-continued

```
<210> SEQ ID NO 12
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 12

Met Val Leu Thr Leu Leu Leu Ser Ala Tyr Lys Leu Cys Arg Phe Phe
1               5                   10                  15

Ala Met Ser Gly Pro Arg Pro Gly Ala Glu Arg Leu Ala Val Pro Gly
                20                  25                  30

Pro Asp Gly Gly Gly Gly Thr Gly Pro Trp Trp Ala Ala Gly Gly Arg
            35                  40                  45

Gly Pro Arg Glu Val Ser Pro Gly Ala Gly Thr Glu Val Gln Asp Ala
        50                  55                  60

Leu Glu Arg Ala Leu Pro Glu Leu Gln Gln Ala Leu Ser Ala Leu Lys
65                  70                  75                  80

Gln Ala Gly Gly Ala Arg Ala Val Gly Ala Gly Leu Ala Glu Val Phe
                85                  90                  95

Gln Leu Val Glu Glu Ala Trp Leu Leu Pro Ala Val Gly Arg Glu Val
            100                 105                 110

Ala Gln Gly Leu Cys Asp Ala Ile Arg Leu Asp Gly Gly Leu Asp Leu
        115                 120                 125

Leu Leu Arg Leu Leu Gln Ala Pro Glu Leu Glu Thr Arg Val Gln Ala
        130                 135                 140

Ala Arg Leu Leu Glu Gln Ile Leu Val Ala Glu Asn Arg Asp Arg Val
145                 150                 155                 160

Ala Arg Ile Gly Leu Gly Val Ile Leu Asn Leu Ala Lys Glu Arg Glu
                165                 170                 175

Pro Val Glu Leu Ala Arg Ser Val Ala Gly Ile Leu Glu His Met Phe
            180                 185                 190

Lys His Ser Glu Glu Thr Cys Gln Arg Leu Val Ala Ala Gly Gly Leu
        195                 200                 205

Asp Ala Val Leu Tyr Trp Cys Arg Arg Thr Asp Pro Ala Leu Leu Arg
    210                 215                 220

His Cys Ala Leu Ala Leu Gly Asn Cys Ala Leu His Gly Gly Gln Ala
225                 230                 235                 240

Val Gln Arg Arg Met Val Glu Lys Arg Ala Ala Glu Trp Leu Phe Pro
                245                 250                 255

Leu Ala Phe Ser Lys Glu Asp Glu Leu Leu Arg Leu His Ala Cys Leu
            260                 265                 270

Ala Val Ala Val Leu Ala Thr Asn Lys Glu Val Glu Arg Glu Val Glu
        275                 280                 285

Arg Ser Gly Thr Leu Ala Leu Val Glu Pro Leu Val Ala Ser Leu Asp
    290                 295                 300

Pro Gly Arg Phe Ala Arg Cys Leu Val Asp Ala Ser Asp Thr Ser Gln
305                 310                 315                 320

Gly Arg Gly Pro Asp Asp Leu Gln Arg Leu Val Pro Leu Leu Asp Ser
                325                 330                 335

Asn Arg Leu Glu Ala Gln Cys Ile Gly Ala Phe Tyr Leu Cys Ala Glu
            340                 345                 350

Ala Ala Ile Lys Ser Leu Gln Gly Lys Thr Lys Val Phe Ser Asp Ile
        355                 360                 365

Gly Ala Ile Gln Ser Leu Lys Arg Leu Val Ser Tyr Ser Thr Asn Gly
```

-continued

```
             370             375             380
Thr Lys Ser Ala Leu Ala Lys Arg Ala Leu Arg Leu Leu Gly Glu Glu
385             390             395             400

Val Pro Arg Pro Ile Leu Pro Ser Val Pro Ser Trp Lys Glu Ala Glu
                405             410             415

Val Gln Thr Trp Leu Gln Gln Ile Gly Phe Ser Lys Tyr Cys Glu Ser
                420             425             430

Phe Arg Glu Gln Gln Val Asp Gly Asp Leu Leu Leu Arg Leu Thr Glu
            435             440             445

Glu Glu Leu Gln Thr Asp Leu Gly Met Lys Ser Gly Ile Thr Arg Lys
            450             455             460

Arg Phe Phe Arg Glu Leu Thr Glu Leu Lys Thr Phe Ala Asn Tyr Ser
465             470             475             480

Thr Cys Asp Arg Ser Asn Leu Ala Asp Trp Leu Gly Ser Leu Asp Pro
                485             490             495

Arg Phe Arg Gln Tyr Thr Tyr Gly Leu Val Ser Cys Gly Leu Asp Arg
            500             505             510

Ser Leu Leu His Arg Val Ser Glu Gln Gln Leu Leu Glu Asp Cys Gly
            515             520             525

Ile His Leu Gly Val His Arg Ala Arg Ile Leu Thr Ala Ala Arg Glu
            530             535             540

Met Leu His Ser Pro Leu Pro Cys Thr Gly Gly Lys Pro Ser Gly Asp
545             550             555             560

Thr Pro Asp Val Phe Ile Ser Tyr Arg Arg Asn Ser Gly Ser Gln Leu
                565             570             575

Ala Ser Leu Leu Lys Val His Leu Gln Leu His Gly Phe Ser Val Phe
            580             585             590

Ile Asp Val Glu Lys Leu Glu Ala Gly Lys Phe Glu Asp Lys Leu Ile
            595             600             605

Gln Ser Val Met Gly Ala Arg Asn Phe Val Leu Val Leu Ser Pro Gly
            610             615             620

Ala Leu Asp Lys Cys Met Gln Asp His Asp Cys Lys Asp Trp Val His
625             630             635             640

Lys Ala Ile Val Thr Ala Leu Ser Cys Gly Lys Asn Ile Val Pro Ile
                645             650             655

Ile Asp Gly Phe Glu Trp Pro Glu Pro Gln Val Leu Pro Glu Asp Met
                660             665             670

Gln Ala Val Leu Thr Phe Asn Gly Ile Lys Trp Ser Ala Glu Tyr Gln
            675             680             685

Glu Ala Thr Ile Glu Lys Ile Ile Arg Phe Leu Gln Gly Arg Ser Ser
            690             695             700

Arg Asp Ser Ser Ala Gly Ser Asp Thr Ser Leu Glu Gly Ala Ala Pro
705             710             715             720

Met Gly Pro Thr
```

```
<210> SEQ ID NO 13
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 13

Met Val Leu Thr Leu Leu Leu Ser Ala Tyr Lys Leu Cys Arg Phe Phe
1               5               10              15
```

-continued

```
Ala Met Ser Gly Pro Arg Pro Gly Ala Glu Arg Leu Ala Val Pro Gly
            20                  25                  30

Pro Asp Gly Gly Gly Gly Thr Gly Pro Trp Trp Ala Ala Gly Gly Arg
            35                  40                  45

Gly Pro Arg Glu Val Ser Pro Gly Ala Gly Thr Glu Val Gln Asp Ala
    50                  55                  60

Leu Glu Arg Ala Leu Pro Glu Leu Gln Gln Ala Leu Ser Ala Leu Lys
65                  70                  75                  80

Gln Ala Gly Gly Ala Arg Ala Val Gly Ala Gly Leu Ala Glu Val Phe
                85                  90                  95

Gln Leu Val Glu Glu Ala Trp Leu Leu Pro Ala Val Gly Arg Glu Val
            100                 105                 110

Ala Gln Gly Leu Cys Asp Ala Ile Arg Leu Asp Gly Gly Leu Asp Leu
            115                 120                 125

Leu Leu Arg Leu Leu Gln Ala Pro Glu Leu Glu Thr Arg Val Gln Ala
    130                 135                 140

Ala Arg Leu Leu Glu Gln Ile Leu Val Ala Glu Asn Arg Asp Arg Val
145                 150                 155                 160

Ala Arg Ile Gly Leu Gly Val Ile Leu Asn Leu Ala Lys Glu Arg Glu
                165                 170                 175

Pro Val Glu Leu Ala Arg Ser Val Ala Gly Ile Leu Glu His Met Phe
            180                 185                 190

Arg His Ser Glu Glu Thr Cys Gln Arg Leu Val Ala Ala Gly Gly Leu
            195                 200                 205

Asp Ala Val Leu Tyr Trp Cys Arg Arg Thr Asp Pro Ala Leu Leu Arg
    210                 215                 220

His Cys Ala Leu Ala Leu Gly Asn Cys Ala Leu His Gly Gly Gln Ala
225                 230                 235                 240

Val Gln Arg Arg Met Val Glu Lys Arg Ala Ala Glu Trp Leu Phe Pro
                245                 250                 255

Leu Ala Phe Ser Lys Glu Asp Glu Leu Leu Arg Leu His Ala Cys Leu
            260                 265                 270

Ala Val Ala Val Leu Ala Thr Asn Lys Glu Val Glu Arg Glu Val Glu
            275                 280                 285

Arg Ser Gly Thr Leu Ala Leu Val Glu Pro Leu Val Ala Ser Leu Asp
    290                 295                 300

Pro Gly Arg Phe Ala Arg Cys Leu Val Asp Ala Ser Asp Thr Ser Gln
305                 310                 315                 320

Gly Arg Gly Pro Asp Asp Leu Gln Arg Leu Val Pro Leu Leu Asp Ser
                325                 330                 335

Asn Arg Leu Glu Ala Gln Cys Ile Gly Ala Phe Tyr Leu Cys Ala Glu
            340                 345                 350

Ala Ala Ile Lys Ser Leu Gln Gly Lys Thr Lys Val Phe Ser Asp Ile
            355                 360                 365

Gly Ala Ile Gln Ser Leu Lys Arg Leu Val Ser Tyr Ser Thr Asn Gly
    370                 375                 380

Thr Lys Ser Ala Leu Ala Lys Arg Ala Leu Arg Leu Leu Gly Glu Glu
385                 390                 395                 400

Val Pro Arg Pro Ile Leu Pro Ser Val Pro Ser Trp Lys Glu Ala Glu
                405                 410                 415

Val Gln Thr Trp Leu Gln Gln Ile Gly Phe Ser Lys Tyr Cys Glu Ser
            420                 425                 430
```

-continued

```
Phe Arg Glu Gln Gln Val Asp Gly Asp Leu Leu Leu Arg Leu Thr Glu
        435             440             445

Glu Glu Leu Gln Thr Asp Leu Gly Met Lys Ser Gly Ile Thr Arg Lys
        450             455             460

Arg Phe Phe Arg Glu Leu Thr Glu Leu Lys Thr Phe Ala Asn Tyr Ser
465             470             475             480

Thr Cys Asp Arg Ser Asn Leu Ala Asp Trp Leu Gly Ser Leu Asp Pro
                485             490             495

Arg Phe Arg Gln Tyr Thr Tyr Gly Leu Val Ser Cys Gly Leu Asp Arg
                500             505             510

Ser Leu Leu His Arg Val Ser Glu Gln Gln Leu Leu Glu Asp Cys Gly
                515             520             525

Ile His Leu Gly Val His Arg Ala Arg Ile Leu Thr Ala Ala Arg Glu
        530             535             540

Met Leu His Ser Pro Leu Pro Cys Thr Gly Gly Lys Pro Ser Gly Asp
545             550             555             560

Thr Pro Asp Val Phe Ile Ser Tyr Arg Arg Asn Ser Gly Ser Gln Leu
                565             570             575

Ala Ser Leu Leu Lys Val His Leu Gln Leu His Gly Phe Ser Val Phe
                580             585             590

Ile Asp Val Glu Lys Leu Glu Ala Gly Lys Phe Glu Asp Lys Leu Ile
                595             600             605

Gln Ser Val Met Gly Ala Arg Asn Phe Val Leu Val Leu Ser Pro Gly
        610             615             620

Ala Leu Asp Lys Cys Met Gln Asp His Asp Cys Lys Asp Trp Val His
625             630             635             640

Lys Glu Ile Val Thr Ala Leu Ser Cys Gly Lys Asn Ile Val Pro Ile
                645             650             655

Ile Asp Gly Phe Glu Trp Pro Glu Pro Gln Val Leu Pro Glu Asp Met
                660             665             670

Gln Ala Val Leu Thr Phe Asn Gly Ile Lys Trp Ser Ala Glu Tyr Gln
                675             680             685

Glu Ala Thr Ile Glu Lys Ile Ile Arg Phe Leu Gln Gly Arg Ser Ser
        690             695             700

Arg Asp Ser Ser Ala Gly Ser Asp Thr Ser Leu Glu Gly Ala Ala Pro
705             710             715             720

Met Gly Pro Thr

<210> SEQ ID NO 14
<211> LENGTH: 724
<212> TYPE: PRT
<213> ORGANISM: Artificial Sequence
<220> FEATURE:
<223> OTHER INFORMATION: SYNTHESIZED

<400> SEQUENCE: 14

Met Val Leu Thr Leu Leu Leu Ser Ala Tyr Lys Leu Cys Arg Phe Phe
1               5               10              15

Ala Met Ser Gly Pro Arg Pro Gly Ala Glu Arg Leu Ala Val Pro Gly
                20              25              30

Pro Asp Gly Gly Gly Gly Thr Gly Pro Trp Trp Ala Ala Gly Gly Arg
                35              40              45

Gly Pro Arg Glu Val Ser Pro Gly Ala Gly Thr Glu Val Gln Asp Ala
        50              55              60

Leu Glu Arg Ala Leu Pro Glu Leu Gln Gln Ala Leu Ser Ala Leu Lys
```

-continued

```
65                    70                    75                    80

Gln Ala Gly Gly Ala Arg Ala Val Gly Ala Gly Leu Ala Glu Val Phe
                85                    90                    95

Gln Leu Val Glu Glu Ala Trp Leu Leu Pro Ala Val Gly Arg Glu Val
                100                   105                   110

Ala Gln Gly Leu Cys Asp Ala Ile Arg Leu Asp Gly Gly Leu Asp Leu
                115                   120                   125

Leu Leu Arg Leu Leu Gln Ala Pro Glu Leu Glu Thr Arg Val Gln Ala
                130                   135                   140

Ala Arg Leu Leu Glu Gln Ile Leu Val Ala Glu Asn Arg Asp Arg Val
145                   150                   155                   160

Ala Arg Ile Gly Leu Gly Val Ile Leu Asn Leu Ala Lys Glu Arg Glu
                165                   170                   175

Pro Val Glu Leu Ala Arg Ser Val Ala Gly Ile Leu Glu His Met Phe
                180                   185                   190

Arg His Ser Glu Glu Thr Cys Gln Arg Leu Val Ala Ala Gly Gly Leu
                195                   200                   205

Asp Ala Val Leu Tyr Trp Cys Arg Arg Thr Asp Pro Ala Leu Leu Arg
        210                   215                   220

His Cys Ala Leu Ala Leu Gly Asn Cys Ala Leu His Gly Gly Gln Ala
225                   230                   235                   240

Val Gln Arg Arg Met Val Glu Lys Arg Ala Ala Glu Trp Leu Phe Pro
                245                   250                   255

Leu Ala Phe Ser Lys Glu Asp Glu Leu Leu Arg Leu His Ala Cys Leu
                260                   265                   270

Ala Val Ala Val Leu Ala Thr Asn Lys Glu Val Glu Arg Glu Val Glu
                275                   280                   285

Arg Ser Gly Thr Leu Ala Leu Val Glu Pro Leu Val Ala Ser Leu Asp
        290                   295                   300

Pro Gly Arg Phe Ala Arg Cys Leu Val Asp Ala Ser Asp Thr Ser Gln
305                   310                   315                   320

Gly Arg Gly Pro Asp Asp Leu Gln Arg Leu Val Pro Leu Leu Asp Ser
                325                   330                   335

Asn Arg Leu Glu Ala Gln Cys Ile Gly Ala Phe Tyr Leu Cys Ala Glu
                340                   345                   350

Ala Ala Ile Lys Ser Leu Gln Gly Lys Thr Lys Val Phe Ser Asp Ile
        355                   360                   365

Gly Ala Ile Gln Ser Leu Lys Arg Leu Val Ser Tyr Ser Thr Asn Gly
        370                   375                   380

Thr Lys Ser Ala Leu Ala Lys Arg Ala Leu Arg Leu Leu Gly Glu Glu
385                   390                   395                   400

Val Pro Arg Pro Ile Leu Pro Ser Val Pro Ser Trp Lys Glu Ala Glu
                405                   410                   415

Val Gln Thr Trp Leu Gln Gln Ile Gly Phe Ser Lys Tyr Cys Glu Ser
                420                   425                   430

Phe Arg Glu Gln Gln Val Asp Gly Asp Leu Leu Leu Arg Leu Thr Glu
                435                   440                   445

Glu Glu Leu Gln Thr Asp Leu Gly Met Lys Ser Gly Ile Thr Arg Lys
        450                   455                   460

Arg Phe Phe Arg Glu Leu Thr Glu Leu Lys Thr Phe Ala Asn Tyr Ser
465                   470                   475                   480

Thr Cys Asp Arg Ser Asn Leu Ala Asp Trp Leu Gly Ser Leu Asp Pro
                485                   490                   495
```

-continued

```
Arg Phe Arg Gln Tyr Thr Tyr Gly Leu Val Ser Cys Gly Leu Asp Arg
            500                 505                 510

Ser Leu Leu His Arg Val Ser Glu Gln Gln Leu Leu Glu Asp Cys Gly
            515                 520                 525

Ile His Leu Gly Val His Arg Ala Arg Ile Leu Thr Ala Ala Arg Glu
            530                 535                 540

Met Leu His Ser Pro Leu Pro Cys Thr Gly Gly Lys Pro Ser Gly Asp
545                 550                 555                 560

Thr Pro Asp Val Phe Ile Ser Tyr Arg Arg Asn Ser Gly Ser Gln Leu
                565                 570                 575

Ala Ser Leu Leu Lys Val His Leu Gln Leu His Gly Phe Ser Val Phe
            580                 585                 590

Ile Asp Val Glu Lys Leu Glu Ala Gly Lys Phe Glu Asp Lys Leu Ile
            595                 600                 605

Gln Ser Val Met Gly Ala Arg Asn Phe Val Leu Val Leu Ser Pro Gly
            610                 615                 620

Ala Leu Asp Lys Cys Met Gln Asp His Asp Cys Lys Asp Trp Val His
625                 630                 635                 640

Lys Ala Ile Val Thr Ala Leu Ser Cys Gly Lys Asn Ile Val Pro Ile
                645                 650                 655

Ile Asp Gly Phe Glu Trp Pro Glu Pro Gln Val Leu Pro Glu Asp Met
                660                 665                 670

Gln Ala Val Leu Thr Phe Asn Gly Ile Lys Trp Ser Ala Glu Tyr Gln
                675                 680                 685

Glu Ala Thr Ile Glu Lys Ile Ile Arg Phe Leu Gln Gly Arg Ser Ser
            690                 695                 700

Arg Asp Ser Ser Ala Gly Ser Asp Thr Ser Leu Glu Gly Ala Ala Pro
705                 710                 715                 720

Met Gly Pro Thr
```

<210> SEQ ID NO 15
<211> LENGTH: 2172
<212> TYPE: DNA
<213> ORGANISM: Artificial Sequence
<220> FEATURE:
<223> OTHER INFORMATION: SYNTHESIZED

<400> SEQUENCE: 15

```
atggtcctga cgctgcttct ctccgcctac aagctgtgtc gcttcttcgc catgtcgggc      60
ccacggccgg gcgccgagcg gctggcggtg cctgggccag atgggggcgg tggcacgggc     120
ccatggtggg ctgcgggtgg ccgcgggccc cgcgaagtgt cgccgggggc aggcaccgag     180
gtgcaggacg ccctggagcg cgcgctgccg gagctgcagc aggccttgtc cgcgctgaag     240
caggcgggcg gcgcgcgggc cgtgggcgcc ggcctggccg aggtcttcca actggtggag     300
gaggcctggc tgctgccggc cgtgggccgc gaggtagccc agggtctgtg cgacgccatc     360
cgcctcgatg gcggcctcga cctgctgttg cggctgctgc aggcgccgga gttggagacg     420
cgtgtgcagg ccgcgcgcct gctggagcag atcctggtgg ctgagaaccg agaccgcgtg     480
gcgcgcattg ggctgggcgt gatcctgaac ctggcgaagg aacgcgaacc cgtagagctg     540
gcgcggagcg tggcaggcat cttggagcac atgttccggc attcggagga gacatgccag     600
aggctggtgg cggccggcgg cctggacgcg gtgctgtatt ggtgccgccg cacggacccc     660
gcgctgctgc gccactgcgc gctggcgctg ggcaactgcg cgctgcacgg gggccaggcg     720
```

-continued

```
gtgcagcgac gcatggtaga gaagcgcgca gccgagtggc tcttcccgct cgccttctcc     780
aaggaggacg agctgcttcg gctgcacgcc tgcctcgcag tagcggtgtt ggcgactaac     840
aaggaggtgg agcgcgaggt ggagcgctcg ggcacgctgg cgctcgtgga gccgcttgtg     900
gcctcgctgg accctggccg cttcgcccgc tgtctggtgg acgccagcga cacaagccag     960
ggccgcgggc ccgacgacct gcagcgcctc gtgccgttgc tcgactctaa ccgcttggag    1020
gcgcagtgca tcggggcttt ctacctctgc gccgaggctg ccatcaagag cctgcaaggc    1080
aagaccaagg tgttcagcga catcggcgcc atccagagcc tgaaacgcct ggtttcctac    1140
tctaccaatg gcactaagtc ggcgctggcc aagcgcgcgc tgcgcctgct gggcgaggag    1200
gtgccacggc ccatcctgcc ctccgtgccc agctggaagg aggccgaggt tcagacgtgg    1260
ctgcagcaga tcggtttctc caagtactgc gagagcttcc gggagcagca ggtggatggc    1320
gacctgcttc tgcggctcac ggaggaggaa ctccagaccg acctgggcat gaaatcgggc    1380
atcacccgca agaggttctt tagggagctc acggagctca agaccttcgc caactattct    1440
acgtgcgacc gcagcaacct ggcggactgg ctgggcagcc tggacccgcg cttccgccag    1500
tacacctacg gcctggtcag ctgcggcctg gaccgctccc tgctgcaccg cgtgtctgag    1560
cagcagctgc tggaagactg cggcatccac ctgggcgtgc accgcgcccg catcctcacg    1620
gcggccagag aaatgctaca ctccccgctg ccctgtactg gtggcaaacc cagtggggac    1680
actccagatg tcttcatcag ctaccgccgg aactcaggtt cccagctggc cagtctcctg    1740
aaggtgcacc tgcagctgca tggcttcagt gtcttcattg atgtggagaa gctggaagca    1800
ggcaagttcg aggacaaact catccagagt gtcatgggtg cccgcaactt tgtgttggtg    1860
ctatcacctg gagcactgga caagtgcatg caagaccatg actgcaagga ttgggtgcat    1920
aaggagattg tgactgcttt aagctgcggc aagaacattg tgcccatcat tgatggcttc    1980
gagtggcctg agcccaggt cctgcctgag gacatgcagg ctgtgcttac tttcaacggt    2040
atcaagtggt ccgccgaata ccaggaggcc accattgaga agatcatccg cttcctgcag    2100
ggccgctcct cccgggactc atctgcaggc tctgacacca gtttggaggg tgctgcaccc    2160
atgggtccaa cc                                                        2172
```